US010172894B2

United States Patent

(12) United States Patent
Ungerechts et al.

(10) Patent No.: US 10,172,894 B2
(45) Date of Patent: Jan. 8, 2019

(54) RNA VIRUSES FOR IMMUNOVIROTHERAPY

(71) Applicants: Deutsches Krebforschungszentrum, Heidelberg (DE); RUPRECHT-KARLS-UNIVERSITAET HEIDELBERG, Heidelberg (DE)

(72) Inventors: Guy Ungerechts, Heidelberg (DE); Tobias Speck, Bretten (DE); Christine Engeland, Heidelberg (DE); Sascha Bossow, Heidelberg (DE)

(73) Assignees: DEUTSCHES KREBSFORSCHUNGSZENTRUM (DE); RUPRECHT-KARLS-UNIVERSITAET HEIDELBERG (DE)

( * ) Notice: Subject to any disclaimer, the term of this patent is extended or adjusted under 35 U.S.C. 154(b) by 0 days.

(21) Appl. No.: 15/247,426

(22) Filed: Aug. 25, 2016

(65) Prior Publication Data

US 2017/0128505 A1 May 11, 2017

(30) Foreign Application Priority Data

Aug. 26, 2015 (JP) ................................ 2015-166899

(51) Int. Cl.

*A61K 35/768* (2015.01)
*C07K 16/28* (2006.01)
*C07K 16/30* (2006.01)
*C12N 5/0783* (2010.01)
*C12N 7/00* (2006.01)
*A61K 48/00* (2006.01)

(52) U.S. Cl.

CPC ........ *A61K 35/768* (2013.01); *C07K 16/2809* (2013.01); *C07K 16/2887* (2013.01); *C07K 16/3007* (2013.01); *C12N 5/0636* (2013.01); *C12N 7/00* (2013.01); *A61K 48/00* (2013.01); *C07K 2317/31* (2013.01); *C07K 2317/622* (2013.01); *C12N 2501/998* (2013.01); *C12N 2760/18421* (2013.01); *C12N 2760/18432* (2013.01)

(58) Field of Classification Search

None

See application file for complete search history.

(56) References Cited

U.S. PATENT DOCUMENTS 5,591,828 A 1/1997 Bosslet et al.

FOREIGN PATENT DOCUMENTS

EP 0404097 A2 12/1990
WO 93/01161 A1 1/1993

OTHER PUBLICATIONS

Yu et al. T-cell engager-armed oncolytic vaccinia virus significantly enhances antitumor therapy. Mol Ther. Jan. 2014;22(1):102-11. Epub Oct. 17, 2017.*

Grossardt et al. Granulocyte-Macrophage Colony-Stimulating Factor-Armed Oncolytic Measles Virus Is an Effective Therapeutic Cancer Vaccine. Human Gene Therapy 24:644-654 ( Jul. 2013).*

Anker et al., "Severe Liver and Skin Toxicity After Radiation and Vemurafenib in Metastatic Melanoma," J. Clin. Oncol., vol. 31, No. 17, Jun. 10, 2013, pp. 283-287.

G. Galfre and C. Milstein, "[1] Preparation of Monoclonal Antibodies: Strategies and Procedures," Methods in Enzymology, vol. 73,1981, pp. 3-46.

Grossardt et al., "Granulocyte-Macrophage Colony-Stimulating Factor-Armed Oncolytic Measles Virus Is an Effective Therapeutic Cancer Vaccine," Human Gene Therapy, 24, Jul. 2013, pp. 644-654.

Heo et al., "Randomized dose-finding clinical trial of oncolytic immunotherapeutic vaccinia JX-594 in liver cancer," NIH Public Access Author Manuscript, Dec. 17, 2014, pp 1-17.

Holliger et al., "Diabodies: Small bivalent and bispecitic antibody fragments," Proc. Natl. Acad. Sci., vol. 90, Jul. 1993, pp. 6444-6448.

P. J. Hudson and C. Souriau, "Engineered antibodies," Nature Medicine, vol. 9, No. 1, Jan. 2003, pp. 129-134.

Klevenz et al., "Peptide aptamers: exchange of the thioredoxin-A scaffold by alternative platform proteins and its influence on target protein binding," Cell. Mol. Life Sci., 59, 2002, pp. 1993-1998.

G. Kohler and C. Milstein, "Continuous cultures of fused cells secreting antibody of predefined specificity," Nature, vol. 256, Aug. 7, 1975, pp. 495-497.

Melcher et al., "Thunder and Lightning: Immunotherapy and Oncolytic Viruses Collide," Mol. Ther. vol. 19, No. 6, Jun. 2011, pp. 1008-1016.

Russell et al., "Oncolytic Virotherapy," HHS Public Access Author Manuscript, Nat. Bioctechnol., Jan. 10, 2014, pp. 1-31.

Steven M. Albeda and Steve H. Thorne "Giving Oncolytic Vaccinia Virus More BiTE", Molecular Therapy, 2014, vol. 22, No. 1, pp. 6-8.

Zuniga et al., "Attenuated Measles Virus as a Vaccine Vector", Vaccine, 2007, 25(16): 2974-2983.

(Continued)

*Primary Examiner* — Nianxiang Zou

(74) *Attorney, Agent, or Firm* — J.A. Lindeman & Co., PLLC

(57) ABSTRACT

The present invention relates to a recombinant virus of the family Paramyxoviridae, comprising at least one expressible polynucleotide encoding a multispecific binding polypeptide, said multispecific binding polypeptide comprising a first binding domain binding to a surface molecule of an immune cell with antitumor activity, preferably a lymphocyte, more preferably a T cell or a dendritic cell, and a second binding domain binding to a tumor-associated antigen; to a polynucleotide encoding the same, and to a kit comprising the same. Moreover, the present invention relates to a method for treating cancer in a subject afflicted with cancer, comprising contacting said subject with a recombinant virus of the family Paramyxoviridae of the invention, and thereby, treating cancer in a subject afflicted with cancer.

8 Claims, 6 Drawing Sheets

Specification includes a Sequence Listing.

(56) References Cited

OTHER PUBLICATIONS

Speck et al., “Engineering BiTE-armed oncolytic measles viruses for cancer immunovirotherapy”, Feb. 26, 2015, Abstract from Annual meeting of the Deutsche Gessellschaft fur Gentherapie e.V.
Speck et al., “Engineering BiTE-armed oncolytic measles viruses for cancer immunovirotherapy”, Feb. 26, 2015, Poster from Annual meeting of the Deutsche Gessellschaft fur Gentherapie e.V.
Dingli et al., “Image-guided radiovirotherapy for multiple myeloma using a recombinant measles virus expressing the thyroidal sodium iodide symporter”, Blood, 2004, vol. 103, No. 5, pp. 1641-1646.

* cited by examiner

RNA VIRUSES FOR IMMUNOVIROTHERAPY

The present invention relates to a recombinant virus of the family Paramyxoviridae, comprising at least one expressible polynucleotide encoding a multispecific binding polypeptide, said multispecific binding polypeptide comprising a first binding domain binding to a surface molecule of an immune cell with antitumor activity, preferably a lymphocyte, more preferably a T cell or a dendritic cell, and a second binding domain binding to a tumor-associated antigen; to a polynucleotide encoding the same, and to a kit comprising the same. Moreover, the present invention relates to a method for treating cancer in a subject afflicted with cancer, comprising contacting said subject with a recombinant virus of the family Paramyxoviridae of the invention, and thereby, treating cancer in a subject afflicted with cancer.

BACKGROUND

Oncolytic viruses (OV) which replicate selectively in tumor cells are an emerging modality of cancer treatment. Aside from direct cytopathic effects and lysis of tumor cells, interactions of OV with the immune system can trigger systemic anti-tumor immunity. OV have been modified to express immunomodulatory transgenes to further enhance these effects (Melcher et al., Mol Ther. 2011, 19: 1008-1016). The vaccinia virus JX-594 and herpesvirus talimogene laherpavec (TVEC), both harboring GM-CSF, have shown promising results in clinical phase II and III trials (Heo et al., Nat Med. 2013, 19: 329-336 and Andtbacka et al. J Clin Oncol. 2013, 31, suppl; abstr LBA9008).

RNA viruses, in particular members of the family Paramyxoviridae like, e.g. measles virus, have also shown potential use in oncolysis. Viruses of the family Paramyxoviridae are negative-sense single-stranded RNA viruses and include human pathogens like, e.g. human parainfluenza viruses, mumps virus, human respiratory syncytial virus, and measles virus. From wild type measles virus, several non-pathogenic strains, including a vaccine strain, have been derived, which have been shown to remain oncolytic. The measles virus vaccine strain has been developed as a vector platform to target multiple tumor entities and several clinical trials are ongoing (Russell et al., Nat Biotechnol. 2012, 30: 658-670). Recently, the capacity of oncolytic MV encoding GM-CSF to support the induction of a specific anti-tumor immune response in terms of a tumor vaccination effect was demonstrated (Grossardt et al. Hum Gene Ther. 2013, 24: 644-654.).

In general, immune response via T cell activation involves the integration of numerous signals. In order to improve cellular immunity to tumor cells, a variety of immunomodulatory molecules were developed, e.g. “bispecific T cell-engagers” (“BiTEs”). BiTEs are bispecific antibodies, structurally based on two single-chain variable fragments (scFv) with one binding domain targeting the T cell receptor-associated molecule CD3 on T cells and the other domain targeting cell surface molecules on tumor cells. Such cross-linking of even resting T cells to target cells induces an artificial immunological synapse and triggers T cell-mediated target cell lysis. Hence, the BiTE-directed killing is independent of TCR specificity, costimulation and antigen presentation.

There is, however, still a need in the art for improved cancer therapies, in particular for improved oncolytic viruses.

DETAILED DESCRIPTION OF THE INVENTION

Accordingly, the present invention relates to a recombinant virus of the family Paramyxoviridae, comprising at least one expressible polynucleotide encoding a multispecific binding polypeptide, said multispecific binding polypeptide comprising a) a first binding domain binding to a surface molecule of an immune cell with antitumor activity, and b) a second binding domain binding to a tumor-associated antigen.

The terms “virus” and “virus of the family Paramyxoviridae” are known to the skilled person. Preferably, the virus of the family Paramyxoviridae is a member of the genus Morbillivirus. More preferably, the virus of the family Paramyxoviridae is a measles virus (MV), still more preferably an MV strain Edmonston A or B, or, most preferably, vaccine strain Edmonston B.

The term “recombinant virus”, as used herein, relates to a virus comprising a genome modified by biotechnological means as compared to known, naturally occurring, virus genomes. Preferably, the recombinant virus is a virus comprising a genome modified as compared naturally occurring virus genomes. Preferred biotechnological means for modifying a viral genome are known to the skilled person and include any of the methods of molecular cloning, in particular recombinant DNA techniques including, without limitation, cleavage of DNA by restriction enzymes, ligation of DNA, polymerase chain reaction (PCR), cloning of viral genomes, and the like. It is understood by the skilled person that viruses of the family Paramyxoviridae have a single-stranded (−)-RNA as a genome. Accordingly, the genome of the recombinant virus of the present invention, preferably, is obtained by cloning an expression vector as described herein below comprising an expressible nucleotide sequence encoding said recombinant virus genome, followed by expressing said expressible nucleotide sequence encoding said recombinant virus in a permissive host cell. Alternatively, the recombinant virus genome may also be expressed in non-permissive host cells, e.g., preferably, from rodents or other higher eukaryotes.

As used herein, the term “multispecific binding polypeptide” relates to a polypeptide binding, preferably specifically binding, to at least two non-identical epitopes, wherein said epitopes, preferably, are epitopes of non-identical molecules of interest. Preferably, the multispecific binding polypeptide is a polypeptide binding, preferably specifically binding, to two non-identical epitopes, wherein said epitopes, preferably, are epitopes of two non-identical molecules of interest; i.e., the multispecific binding polypeptide, preferably, is a bispecific binding polypeptide. The multispecific binding polypeptide comprises at least a first binding domain binding to a surface molecule of an immune cell with antitumor activity. The term “immune cell with antitumor activity”, as used herein, preferably, relates to a lymphocyte, more preferably a lymphocyte with the capacity to inactivate cancer cells and/or to activate cells inactivating cancer cells. More preferably, an immune cell with antitumor activity is a T cell, a dendritic cell or a natural killer cell. Thus, preferably, the multispecific binding polypeptide comprises a first binding domain binding, more preferably specifically binding, to a surface molecule of a T cell, to a surface molecule of a dendritic cell, and/or to a surface molecule of a natural killer cell, and a second binding domain binding to a tumor-associated antigen. Preferably, the multispecific binding polypeptide further comprises a transport signal, in particular a peptide export signal. Preferably, the constituent parts of the multispecific binding polypeptide, i.e. in particular the first binding domain and the second binding domain, are contiguous in amino acid sequence; thus, the multispecific binding polypeptide is, preferably, expressed from a single open reading frame comprised in a polynucleotide. Thus, preferably, the multispecific binding polypeptide as described herein above is a polypeptide expressible from a single transcription unit. Accordingly, preferably, the multispecific binding polypeptide is a polypeptide or a fusion polypeptide. More preferably, the multispecific binding polypeptide comprises at least one, more preferably two, single-chain antibodies, single-chain Fab polypeptides, or nanobodies. Also preferably, the multispecific binding polypeptide is a secreted polypeptide.

The term "binding domain" is known to the skilled person and, preferably, relates to a, contiguous or non-contiguous, subpart of a polypeptide having the activity of binding, preferably specifically binding, to a molecule of interest (cognate antigen). Preferably, the binding domain binds to its cognate antigen with sufficient affinity to allow detection of a binding domain/antigen complex. Preferably, the dissociation constant ($K_d$) of the binding domain/antigen complex is at most $10^{-6}$ mol/L, more preferably at most $10^{-7}$ mol/L, even more preferably, at most $10^{-8}$ mol/1, most preferably, at most $10^{-9}$ mol/L. The term "specifically binding" is understood by the skilled person. Preferably, specific binding relates to a binding in which the affinity of the binding domain to the cognate antigen is at least threefold, more preferably at least fivefold, still more preferably at least tenfold, even more preferably at least 100 fold, most preferably at least 1000 fold higher than for any non-cognate antigen present in a sample. Accordingly, the dissociation constant (Kd) of any binding domain/non-cognate antigen complex is at least $10^{-6}$ mol/L, more preferably, at least $10^{-5}$ mol/l, most preferably, at least $10^{4}$ mol/L.

Preferably, the binding domains of the multispecific binding polypeptide are independently selected from the list of molecule types consisting of a peptide aptamer, an anticalin, a Designed Ankyrin Repeat Protein (DARPin), and an antibody. Preferably, at least one, more preferably two binding domains are antibodies or parts thereof as specified herein below, more preferably, are single-chain antibodies or nanobodies.

In the context of this invention, a "peptide aptamer" is a peptide specifically binding a molecule of interest. Peptide aptamers, preferably, are peptides comprising 8-80 amino acids, more preferably 10-50 amino acids, and most preferably 15-30 amino acids. They can e.g. be isolated from randomized peptide expression libraries in a suitable host system like baker's yeast (see, for example, Klevenz et al., Cell Mol Life Sci. 2002, 59: 1993-1998). The peptide aptamer, preferably, is present as a binding domain of the multispecific binding polypeptide. As used herein, the term "anticalin" relates to an artificial polypeptide derived from a lipocalin specifically binding to a molecule of interest. Similarly, a "Designed Ankyrin Repeat Protein" or "DARPin", as used herein, is an artificial polypeptide comprising several ankyrin repeat motifs and specifically binding a molecule of interest.

As used herein, the term "antibody" relates to a soluble immunoglobulin from any of the classes IgA, IgD, IgE, IgG, or IgM, having the activity of specifically binding a molecule of interest. Antibodies against antigens can be prepared by well known methods using, e.g., a purified molecule of interest or a suitable fragment derived therefrom as an antigen. A fragment which is suitable as an antigen may be identified by antigenicity determining algorithms well known in the art. Such fragments may be obtained either from one of the molecules of interest by proteolytic digestion, may be a synthetic peptide, or may be obtained by recombinant expression. Preferably, a peptide of a molecule of interest used as an antigen is located at the exterior of a cell expressing the molecule of interest; i.e. preferably, the epitope the binding domain interacts with, preferably, is an extracellular domain. Suitability of an antibody generated as a binding domain can be tested by the assay as described herein in the Examples. Preferably, the antibody of the present invention is a monoclonal antibody, a human or humanized antibody or primatized, chimerized or fragment thereof so long as they exhibit the desired binding activity as specified elsewhere herein. Also comprised as antibodies of the present invention are a bispecific antibody, a synthetic antibody, or a chemically modified derivative of any of these. Preferably, the antibody of the present invention shall specifically bind (i.e. does not cross react with other polypeptides or peptides) to a molecule of interest as specified above. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Kohler and Milstein, Nature. 1975. 256: 495; and Galfré, Meth. Enzymol. 1981, 73: 3, which comprise the fusion of mouse myeloma cells to spleen cells derived from immunized mammals.

"Antibody fragments" comprise a portion of an intact antibody, in an embodiment, comprising the antigen-binding region thereof. Examples of antibody fragments and fusion proteins of variable regions include Fab, Fab', F(ab')2, and Fv fragments; diabodies; linear antibodies; single-chain antibody molecules; single-domain-antibodies (VHH), also known as nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. Preferably, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs, also referred to as complementarity determining regions (CDRs)) of each variable domain interact to define an antigen-binding site. Collectively, the six HVRs of one scFv confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH)

connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

Preferably, the multispecific binding polypeptide comprises further amino acids which may serve e.g. as immunogenic antigens, as a tag for purification or detection or as a linker. In another preferred embodiment of the multispecific binding polypeptide of the present invention, said multispecific binding polypeptide further comprises a detectable tag. The term "detectable tag" refers to a stretch of amino acids which are added to or introduced into the multispecific binding polypeptide of the invention. Preferably, the tag shall be added C- or N-terminally to the multispecific binding polypeptide of the present invention. The said stretch of amino acids shall allow for detection of the multispecific binding polypeptide by an antibody which specifically recognizes the tag or it shall allow for forming a functional conformation, such as a chelator or it shall allow for visualization by fluorescent tags. Preferred tags are the Myc-tag, FLAG-tag, poly-His-tag, HA-tag, GST-tag or GFP-tag. These tags are all well known in the art. More preferably, the multispecific binding polypeptide further comprises a cytokine as specified elsewhere herein.

Preferably, the multispecific binding polypeptide as described herein above is a polypeptide expressible from a single transcription unit. Accordingly, preferably, the multispecific binding polypeptide is a polypeptide or a fusion polypeptide. More preferably, the multispecific binding polypeptide comprises at least one, more preferably two, single-chain antibodies, single-chain Fab polypeptides, or nanobodies.

Preferably, the first binding domain of the multispecific binding polypeptide binds to a surface molecule of a T cell. Preferably, the surface molecule of a T cell is selected from the group consisting of CD3, CD2, CD5, CD6, CD9, CD11A, CD25 (IL-2 receptor alpha-chain), CD26, CD28, CD29, CD40L, CD43, CD44, CD45RO, CD45RA, CD45RB, CD47, CD58 (LFA-3), CD69, CD70, CXCR4, CD107a, CD122 (IL-2 receptor beta-chain), CD132 (IL-2 receptor gamma-chain), CD134, CD137 and CD247. More preferably, the surface molecule of a T cell is CD3. More preferably, the first binding domain comprises a single-chain antibody against CD3. Most preferably, the first binding domain comprises the amino acid sequence of SEQ ID NO:1 or SEQ ID NO:2.

Also preferably, the first binding domain of the multispecific binding polypeptide binds to a surface molecule of a dendritic cell. Preferably, the surface molecule of a dendritic cell is selected from the group consisting of CD1a/b, CD11c, CD16a, CD40, CD68, CD80, CD83, CD86, IFNAR1 (interferon-alpha/beta receptor), CD119 (interferon-gamma receptor 1), CDB197 (CCR7), CD205 (DEL-205), CD209 (DC-SIGN) and CD227 (MUC1).

0019 Also preferably, the first binding domain of the multispecific binding polypeptide binds to a surface molecule of a natural killer cell (NK cell). Preferably, the surface molecule of a natural killer cell is selected from the group consisting of CD16a, NKG2D, and NCRs such as NKp30, NKp44 and NKp46.

Also preferably, the second binding domain of the multispecific binding polypeptide binds to a tumor-associated antigen. Preferably, the tumor-associated antigen is a tumor-associated antigen exposed on the surface of a tumor cell. More preferably, the tumor-associated antigen is selected from the group consisting of androgen receptor (AR), BCL-1, calprotectin, carcinoembryonic antigen (CEA), EGFRs, epithelial cell adhesion molecule (Ep-CAM), epithelial sialomucin, membrane estrogen receptor (mERs), FAP, HER2/neu, human high molecular weight-melanoma-associated antigen (HMW-MAA), IL-6, MOC-1, MOC-21, MOC-52, melan-A/MART-1, melanoma-associated antigen, mucin, OKT9, progesterone receptor (PGR), prostate specific antigen (PSA), prostate stem cell antigen (PSCA), prostate-specific membrane antigen (PSMA), symaptophysin, VEGFRs, CD19, CD20, CD22, CD30 and CD33. Most preferably, the tumor-associated antigen is carcinoembryonic antigen (CEA) or CD20. Preferably, the second binding domain comprises a single-chain antibody against CEA. More preferably, the second binding domain comprises the amino acid sequence of SEQ ID NO:3. Also preferably, the second binding domain comprises a single-chain antibody against CD20. More preferably, the second binding domain comprises the amino acid sequence of SEQ ID NO:4. Also preferably, the tumor-associated antigen is a glycoprotein of an oncotropic and/or oncolytic virus.

The term "secreted", as used herein, relates to a compound being transferred from the interior of a host cell to the exterior of said host cell by a mechanism intrinsic to said host cell. Preferably, in case the multispecific binding polypeptide is a peptide or polypeptide, said secretion is mediated by a, preferably eukaryotic, signal peptide mediating import of said peptide or polypeptide into the lumen of the endoplasmic reticulum and, more preferably, by the absence of retention signals. Signal peptides causing secretion of peptides or polypeptides are known in the art. Preferably, the signal peptide is or comprises an Ig leader sequence. More preferably, the signal peptide is or comprises a human Ig leader sequence. More preferably, the signal peptide is or comprises a matching leader sequence, i.e. a leader sequence selected from the same Ig kappa subgroup as the variable light chain of the antibody, preferably, of the single-chain antibody.

The term "cytokine" is known to the skilled person and relates to any one of a group of peptides released by cells and affecting the state or behaviour of other or the same cells. Preferably, the cytokine is a chemokine, an interferon, an interleukin, a lymphokine, or a tumor necrosis factor. More preferably, the cytokine is GM-CSF (Genbank Acc NO: AAA52121.1 GI:181146, preferably encoded by Genbank Acc NO: M10663.1 GI:181145) or Interleukin-12 (p35 subunit, Genbank Acc NO: AAD16432.1 GI:4323579; p40 subunit, Genbank Acc NO: AAG32620.1 GI:11192035.)

Moreover, also encompassed are variants of the aforementioned multispecific binding polypeptides. Such variants have at least the same essential biological activity as the specific multispecific binding polypeptides. Moreover, it is to be understood that a variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino sequence of the specific inhibitory peptides. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining, preferably over the whole length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific multispecific binding polypeptides or the aforementioned types of variants as long as these fragments and/or variants have the essential biological activity as referred to above. Such fragments may be or be derived from, e.g., degradation products or splice variants of the multispecific binding polypeptides. Further included are variants which differ due to posttranslational modifications such as phosphorylation, glycosylation, ubiquitinylation, sumoylation or myristylation.

The term "expressible polynucleotide", as used herein, relates to a polynucleotide operatively linked to at least one expression control sequence causing transcription of the nucleic acid sequence comprised in said polynucleotide to occur, preferably in eukaryotic cells or isolated fractions thereof, preferably into a translatable mRNA or into a viral genome. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Preferably, the aforesaid at least one expression control sequence is an expression control sequence of a (−)strand RNA virus, more preferably of a Paramyxovirus as described herein above, most preferably of an MV. Thus, preferably, at least one expression control sequence comprises a (−)strand RNA viral regulatory sequence ensuring initiation of transcription (consensus "gene start signal", preferably consensus MV "gene start signal") and termination signals (consensus "gene stop signal", preferably, consensus MV "gene stop signal") ensuring termination of transcription and stabilization of the transcript. It is known in the art that production of viral particles in permissive host cells can be initiated by transfecting into said permissive host cells one or more expressible DNA constructs encoding (i) a recombinant viral anti-genome, (ii) the viral L gene, (iii) the viral P gene and (iv) the viral N gene. It is also understood by the skilled person that, once a viral genome and the aforesaid viral genes were expressed in said host cell, replication and assembly of viral particles occurs in the cytoplasm of the host cell and is, therefore, solely dependent on viral regulatory signals. Preferably, the expressible polynucleotide comprises the nucleic acid sequence of SEQ ID NO:5.

The term "polynucleotide", as used in accordance with the present invention, encompasses variants of the aforementioned specific polynucleotides. Moreover, it is to be understood that the polypeptides having amino acid sequences of the polypeptides of the present invention may also be encoded due to the degenerate genetic code by more than one species of polynucleotide. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a peptide or polypeptide having the activity as specified herein. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above. Alternatively, polynucleotide variants are obtainable by PCR-based techniques such as mixed oligonucleotide primer-based amplification of DNA, i.e. using degenerate primers against conserved domains of the polypeptides or peptides of the present invention. Conserved domains of the polypeptides or peptides of the present invention may be identified by a sequence comparison of the nucleic acid sequence of the polynucleotide or of the amino acid sequence of the polypeptides as specified above. Suitable PCR conditions are well known in the art. As a template, DNA or cDNA from appropriate cells may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences detailed above. The percent identity values are, preferably, calculated over the entire amino acid or nucleic acid sequence region. A series of programs based on a variety of algorithms is available to the skilled worker for comparing different sequences as described herein above. A polynucleotide comprising a fragment of any of the aforementioned nucleic acid sequences and encoding a polypeptide or peptide comprising or consisting of the domains conferring the biological activities of a polypeptide of the present invention is also encompassed as a polynucleotide of the present invention. The polynucleotide of the present invention shall be provided, preferably, either as an isolated polynucleotide (i.e. isolated from its natural context) or in genetically modified form. The polynucleotide, preferably, is DNA including cDNA, or RNA. The term encompasses single as well as double stranded polynucleotides. Also included by the term polynucleotide, preferably, are chemically modified polynucleotides including naturally occurring modified polynucleotides such as glycosylated or methylated polynucleotides or artificially modified ones such as biotinylated polynucleotides. The polynucleotides of the present invention either essentially consist of the aforementioned nucleic acid sequences or comprise the aforementioned nucleic acid sequences. Thus, they may contain further nucleic acid sequences as well.

The term "polynucleotide encoding a recombinant virus", as used herein, relates to a polynucleotide comprising a nucleic acid sequence or nucleic acid sequences required for generating a virus particle or a virus-like particle in a host cell. It is understood by the skilled person that a virus is constituted by a polynucleotide genome and at least one kind of capsid polypeptide. Accordingly, the polynucleotide encoding a recombinant virus of the present invention, preferably, comprises a recombinant virus genome. As will be understood by the skilled person, in case the polynucleotide encoding a recombinant virus is comprised in a virus according to the present invention, the polynucleotide is (−)strand RNA. It is also understood by the skilled person that in case the polynucleotide is DNA comprised in a host cell, at least an RNA-dependent RNA polymerase activity will additionally be required to produce viral particles from said DNA polynucleotide. Preferably, the polynucleotide encoding a recombinant virus comprises or consists of the nucleic acid sequence of SEQ ID NO:6-9. As annotated herein, the sequence of the DNA copy of negative-strand (−)RNA viruses is annotated in the usual 5'→3'-orientation; this corresponds to the viral sequence in antigenomic (+)RNA orientation with respect to the natural 3'→5'-orientation of negative-strand (−)RNA viruses.

As used herein, the term "host cell" relates to a vertebrate cell. Preferably, the cell is a mammalian cell, more preferably, a mouse, rat, cat, dog, hamster, guinea pig, sheep, goat, pig, cattle, or horse cell. Still more preferably, the host cell is a primate cell. Most preferably, the host cell is a human cell. Preferably, the host cell is a tumor cell, more preferably a cancer cell.

Advantageously, it was found in the work underlying the present invention that measles virus can be engineered to express multispecific binding polypeptides destined for secretion and that these polypeptides are efficiently secreted during viral replication in the cell. Moreover, it was found that by administering measles virus expressing a multispecific binding polypeptide according to the invention, T cells can be effectively tethered to tumor cells. In contrast to methods of the prior art, no systemic treatment with the multispecific binding polypeptide is required.

The definitions made above apply mutatis mutandis to the following. Additional definitions and explanations made further below also apply for all embodiments described in this specification mutatis mutandis.

The present invention further relates to a polynucleotide encoding the recombinant virus of the family Paramyxoviridae according to the present invention.

The present invention also relates to a medicament comprising the recombinant virus of the family Paramyxoviridae of the present invention and at least one pharmacologically acceptable excipient.

The terms "medicament" and "pharmaceutical composition", as used herein, relate to the compounds of the present invention and optionally one or more pharmaceutically acceptable carrier, i.e. excipient. The compounds of the present invention can be formulated as pharmaceutically acceptable salts. Acceptable salts comprise acetate, methyl ester, HCl, sulfate, chloride and the like. The pharmaceutical compositions are, preferably, administered locally, topically or systemically. Suitable routes of administration conventionally used for drug administration are oral, intravenous, or parenteral administration as well as inhalation. A preferred route of administration is intra-tumoral administration. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The excipient(s) must be acceptable in the sense of being compatible with the other ingredients of the formulation and being not deleterious to the recipient thereof. The excipient employed may be, for example, a solid, a gel or a liquid carrier. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 μg for a polypeptide or polynucleotide, or $10^4$-$10^8$ viral particles for a virus or a virus-like particle; however, doses below or above this exemplary range are envisioned, especially considering the aforementioned factors. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The present invention also relates to a combined preparation for simultaneous, separate or sequential use comprising at least one virus of the family Paramyxoviridae and at least one multispecific binding polypeptide.

A "combined preparation" as referred to in this application preferably comprises all pharmaceutically active compounds in one preparation so that all compounds are administered simultaneously and in the same way.

Also preferably, the combined preparation comprises at least two physically separated preparations for separate administration, wherein each preparation contains at least one pharmaceutically active compound. The latter alternative is preferred in cases where the pharmaceutically active compounds of the combined preparation are administered by different routes, e.g. parenterally and intra-tumorally, e.g. due to their chemical or physiological properties, or e.g. in cases where the paramyxovirus is administered intra-tumorally and the multispecific binding polypeptide is administered parenterally.

Preferably, the at least two separated preparations are administered simultaneously. This means that the time frames of the administration of the preparations overlap.

Also preferred is the sequential administration of the at least two preparations, wherein the administration of the single preparations shall occur in time frames which do not overlap, but are selected so that the at least two pharmaceutically active compounds of the preparation are present in the body of a subject at least in overlapping time intervals. Preferably, the at least two preparations are administered in a time interval of 1 minute, 5 minutes, 15 minutes, 30 minutes, 1 hour, 2 hours, 4 hours, 8 hours, 16 hours, 1 day or 2 days.

Accordingly, the present invention also relates to a method of treating inappropriate cell proliferation in a subject comprising a) contacting said subject with a virus of the family Paramyxoviridae and with a multispecific binding polypeptide according to the present invention, and b) thereby, treating inappropriate cell proliferation in a subject.

Preferably, the inappropriate cell proliferation is cancer. Moreover, as will be understood by the skilled person, contacting a subject may be simultaneous or sequential contacting as specified herein above. As will be also understood by the skilled person, a subject with a virus of the family Paramyxoviridae and with a multispecific binding polypeptide may be accomplished by contacting said subject with a recombinant virus of the family Paramyxoviridae according to the present invention.

Accordingly, the present invention further relates to a method for treating cancer in a subject afflicted with cancer, comprising a) contacting said subject with a recombinant virus of the family Paramyxoviridae according to the present invention, and b) thereby, treating cancer in a subject afflicted with cancer.

The methods of treatment of the present invention, preferably, may comprise steps in addition to those explicitly mentioned above. For example, further steps may relate, e.g., to localizing a tumor and/or diagnosing cancer for step a), or administration of additional medication for step b). Moreover, one or more of said steps may be performed by automated equipment. The method of the present invention, preferably, is an in vivo method of treatment.

The term "treatment" refers to an amelioration of the diseases or disorders referred to herein or the symptoms accompanied therewith to a significant extent. Said treating as used herein also includes an entire restoration of the health with respect to the diseases or disorders referred to herein. It is to be understood that treating as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20% at least 50% at least 60%, at least 70%, at least 80%, or at least 90% of the subjects of a given cohort or population. Preferably, treating cancer is reducing tumor burden in a subject.

As will be understood by the skilled person, effectiveness of treatment of e.g. cancer is dependent on a variety of factors including, e.g. cancer stage and cancer type.

As used herein, the term “subject” relates to a vertebrate. Preferably, the subject is a mammal, more preferably, a mouse, rat, cat, dog, hamster, guinea pig, sheep, goat, pig, cattle, or horse. Still more preferably, the subject is a primate. Most preferably, the subject is a human. Preferably, the subject is afflicted with a disease caused or aggravated by an insufficient response of the immune response of said subject, more preferably, the subject is afflicted with cancer.

The term “cancer”, as used herein, relates to a disease of an animal, including man, characterized by uncontrolled growth by a group of body cells (“cancer cells”). This uncontrolled growth may be accompanied by intrusion into and destruction of surrounding tissue and possibly spread of cancer cells to other locations in the body. Preferably, also included by the term cancer is a relapse.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, fibrosarcoma, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenström macroglobulinemia, and wilms tumor. More preferably, the cancer is a solid cancer, a metastasis, or a relapse thereof. Most preferably, the cancer is a tumor derived from malignant melanoma, head and neck cancer, hepatocellular carcinoma, pancreatic carcinoma, prostate cancer, renal cell carcinoma, gastric carcinoma, colorectal carcinoma, lymphomas or leukemias.

The present invention further relates to an in vitro method for activating immune cells with antitumor activity in a sample comprising cancer cells and immune cells, comprising a) contacting said sample comprising cancer cells and immune cells with a recombinant virus of the family Paramyxoviridae according to the present invention, and b) thereby, activating immune cells with antitumor activity comprised in said sample.

The method for activating immune cells with antitumor activity may comprise steps in addition to those explicitly mentioned above. For example, further steps may relate, e.g., to providing the recombinant virus of the family Paramyxoviridae for step a), administering further activating compounds, e.g. cytokines, to the immune cells in step b), or separating immune cells from cancer cells after step b). Moreover, one or more of said steps may be performed by automated equipment.

The present invention also relates to a recombinant virus of the family Paramyxoviridae according to the present invention for use in medical treatment.

Moreover, the present invention relates to a recombinant virus of the family Paramyxoviridae for use in treatment of inappropriate cell proliferation.

The term “inappropriate cell proliferation” relates to any proliferation of cells of a subject which is not appropriate to the physiological state of said subject and/or to the tissue context of said cells. Preferably, inappropriate cell proliferation is caused or aggravated by an inhibition or insufficient activation of the immune system, more preferably inhibition or insufficient activation of T cells. Also preferably, inappropriate cell proliferation is cancer.

The present invention further relates to a kit comprising at least the recombinant virus of the family Paramyxoviridae housed in a container.

The term “kit”, as used herein, refers to a collection of the aforementioned components. Preferably, said components are combined with additional components, preferably within an outer container. The outer container, also preferably, comprises instructions for carrying out a method of the present invention. Examples for such the components of the kit as well as methods for their use have been given in this specification. The kit, preferably, contains the aforementioned components in a ready-to-use formulation. Preferably, the kit may additionally comprise instructions, e.g., a user's manual for applying the recombinant virus of the family Paramyxoviridae with respect to the applications provided by the methods of the present invention. Details are to be found elsewhere in this specification. Additionally, such user's manual may provide instructions about correctly using the components of the kit. A user's manual may be provided in paper or electronic form, e.g., stored on CD or CD ROM. The present invention also relates to the use of said kit in any of the methods according to the present invention.

Summarizing the findings of the present invention, the following embodiments are preferred:

Embodiment 1

A recombinant virus of the family Paramyxoviridae, comprising at least one expressible polynucleotide encoding a multispecific binding polypeptide, said multispecific binding polypeptide comprising a) a first binding domain binding to a surface molecule of an immune cell with antitumor activity, preferably a lymphocyte, more preferably a T cell or a dendritic cell, and b) a second binding domain binding to a tumor-associated antigen.

Embodiment 2

The recombinant virus of the family Paramyxoviridae of embodiment 1, wherein said surface molecule of a T cell is selected from the group consisting of CD3, CD2, CD5, CD6, CD9, CD11A, CD25 (IL-2 receptor alpha-chain), CD26, CD28, CD29, CD40L, CD43, CD44, CD45RO, CD45RA, CD45RB, CD47, CD58 (LFA-3), CD69, CD70, CXCR4, CD107a, CD122 (IL-2 receptor beta-chain), CD132 (IL-2 receptor gamma-chain), CD134, CD137 and CD247, preferably is CD3.

Embodiment 3

The recombinant virus of the family Paramyxoviridae of embodiment 1 or 2, wherein said surface molecule of a dendritic cell is selected from the group consisting of CD1a/b, CD11c, CD16a, CD40, CD68, CD80, CD83, CD86, IFNAR1 (interferon-alpha/beta receptor), CD119 (interferon-gamma receptor 1), CDB197 (CCR7), CD205 (DEL-205), CD209 (DC-SIGN), and CD227 (MUC1).

Embodiment 4

The recombinant virus of the family Paramyxoviridae of embodiment 1 to 3, wherein said surface molecule of a natural killer cell is selected from the group consisting of CD16a, NKG2D and NCRs such as NKp30, NKp44 and NKp46.

Embodiment 5

The recombinant virus of the family Paramyxoviridae of any one of embodiments 1 to 4, wherein said tumor-associated antigen is a tumor-associated antigen exposed on the surface of a tumor cell.

Embodiment 6

The recombinant virus of the family Paramyxoviridae of any one of embodiments 1 to 5, wherein said tumor-associated antigen is selected from the group consisting of androgen receptor (AR), BCL-1, calprotectin, carcinoembryonic antigen (CEA), EGFRs, epithelial cell adhesion molecule (Ep-CAM), epithelial sialomucin, membrane estrogen receptors (mER), FAP HER2/neu, human high molecular weight melanoma-associated antigen (HMW-MAA), IL-6, MOC-1, MOC-21, MOC-52, melan-A/MART-1, melanoma-associated antigen, mucin, OKT9, progesterone receptor (PGR), prostate specific antigen (PSA), prostate stem cell antigen (PSCA), prostate-specific membrane antigen (PSMA), symaptophysin, VEGFRs, CD19, CD20, CD22, CD30 and CD33, preferably is carcinoembryonic antigen (CEA) or CD20.

Embodiment 7

The recombinant virus of the family Paramyxoviridae of any one of embodiments 1 to 6, wherein said first binding domain is a binding domain binding to a surface molecule of a T cell, preferably to CD3.

Embodiment 8

The recombinant virus of the family Paramyxoviridae of any one of embodiments 1 to 7, wherein said multispecific binding polypeptide is a bispecific binding polypeptide.

Embodiment 9

The recombinant virus of the family Paramyxoviridae of any one of embodiments 1 to 8, wherein said multispecific binding polypeptide is a secreted multispecific binding polypeptide.

Embodiment 10

The recombinant virus of the family Paramyxoviridae of any one of embodiments 1 to 9, wherein said recombinant virus is a recombinant Morbillivirus, preferably, a recombinant measles virus (MV).

Embodiment 11

The recombinant MV of embodiment 10, wherein said recombinant MV is derived from MV strain Edmonston A or B, preferably vaccine strain Edmonston B.

Embodiment 12

The recombinant virus of the family Paramyxoviridae of any one of embodiments 1 to 11, wherein said first binding domain comprises a single-chain antibody against CD3.

Embodiment 13

The recombinant virus of the family Paramyxoviridae of embodiment 12, wherein said single-chain antibody against CD3 comprises the amino acid sequence of SEQ ID NO:1 or SEQ ID NO:2.

Embodiment 14

The recombinant virus of the family Paramyxoviridae of any one of embodiments 1 to 13, wherein said second binding domain comprises a single-chain antibody against CEA.

Embodiment 15

The recombinant virus of the family Paramyxoviridae of embodiment 14, wherein said single-chain antibody against CEA comprises the amino acid sequence of SEQ ID NO:3.

Embodiment 16

The recombinant virus of the family Paramyxoviridae of any one of embodiments 1 to 13, wherein said second binding domain comprises a single-chain antibody against CD20.

Embodiment 17

The recombinant virus of the family Paramyxoviridae of embodiment 16, wherein said single-chain antibody against CD20 comprises the amino acid sequence of SEQ ID NO:4.

Embodiment 18

The recombinant virus of the family Paramyxoviridae of any one of embodiments 1 to 17, wherein the at least one expressible polynucleotide encoding a multispecific binding polypeptide is comprised in a polynucleotide encoding the recombinant virus of the family Paramyxoviridae.

Embodiment 19

The recombinant virus of the family Paramyxoviridae of any one of embodiments 1 to 18, wherein said multispecific binding polypeptide further comprises a cytokine.

Embodiment 20

The recombinant virus of the family Paramyxoviridae of embodiment 19, wherein said cytokine is a cytokine, preferably selected from the list consisting of interleukin 2 (IL-2), interleukin 4 (IL-4), interleukin 6 (IL-6), interleukin 12 (IL-12), interleukin 15 (IL-15), granulocyte colony stimulating factor (G-CSF), granulocyte and macrophage colony stimulating factor (GM-CSF), interferon alpha, interferon beta interferon gamma, and tumor necrosis factor (TNF).

Embodiment 21

A polynucleotide encoding the recombinant virus of the family Paramyxoviridae according to any one of embodiments 1 to 20.

Embodiment 22

The polynucleotide of embodiment 21, wherein said polynucleotide comprises the nucleic acid sequence of SEQ ID NO:6-9.

Embodiment 23

A medicament comprising the recombinant virus of the family Paramyxoviridae of any one of embodiments 1 to 20 and/or the polynucleotide of embodiment 21 or 22, and at least one pharmacologically acceptable excipient.

Embodiment 24

A method for treating cancer in a subject afflicted with cancer, comprising a) contacting said subject with a recombinant virus of the family Paramyxoviridae according of any one of embodiments 1 to 20 and/or with a polynucleotide according to embodiment 21 or 22, and b) thereby, treating cancer in a subject afflicted with cancer.

Embodiment 25

The method of embodiment 24, wherein said cancer is a solid cancer, a metastasis, or a relapse thereof Embodiment 26

The method of embodiment 24 or 25, wherein treating cancer is reducing tumor burden.

Embodiment 27

The method of any one of embodiments 24 to 26, wherein said cancer is malignant melanoma, head and neck cancer, hepatocellular carcinoma, pancreatic carcinoma, prostate cancer, renal cell carcinoma, gastric carcinoma, colorectal carcinoma, lymphomas or leukemias.

Embodiment 28

An in vitro method for activating immune cells with antitumor activity in a sample comprising cancer cells and immune cells, comprising a) contacting said sample comprising cancer cells and immune cells with a recombinant virus of the family Paramyxoviridae of any one of embodiments 1 to 20 and/or with a polynucleotide according to embodiment 21 or 22, and b) thereby, activating immune cells with antitumor activity comprised in said sample.

Embodiment 29

A recombinant virus of the family Paramyxoviridae according to any one of embodiments 1 to 20 and/or a polynucleotide according to embodiment 21 or 22 for use in medical treatment.

Embodiment 30

A recombinant virus of the family Paramyxoviridae according to any one of embodiments 1 to 20 and/or a polynucleotide according to embodiment 21 or 22 for use in treatment of inappropriate cell proliferation.

Embodiment 31

The recombinant virus of the family Paramyxoviridae for use of embodiment 30, wherein treatment of inappropriate cell proliferation is cancer treatment.

Embodiment 32

Kit comprising at least the recombinant virus of the family Paramyxoviridae according to any one of embodiments 1 to 20 and/or a polynucleotide according to embodiment 21 or 22 housed in a container.

Embodiment 33

A method of treating inappropriate cell proliferation in a subject comprising a) contacting said subject with a virus of the family Paramyxoviridae and with a multispecific binding polypeptide according to the present invention, and b) thereby, treating inappropriate cell proliferation in a subject.

Embodiment 34

A combined preparation for simultaneous, separate or sequential use comprising at least one virus of the family Paramyxoviridae and at least one multispecific binding polypeptide.

Embodiment 35

Use of a virus of the family Paramyxoviridae according of any one of embodiments 1 to 20, of a polynucleotide according to embodiment 21 or 22, of a kit according to embodiment 32, and/or of a combined preparation according to embodiment 34, for the manufacture of a medicament for treating disease, preferably for treating inappropriate cell proliferation, more preferably for treating cancer.

All references cited in this specification are herewith incorporated by reference with respect to their entire disclosure content and the disclosure content specifically mentioned in this specification.

BRIEF DESCRIPTION OF THE DRAWINGS

FIG. 2*a* shows specific binding of the indicated multispecific binding polypeptides to their respective TAA targets in terms of recombinant human protein in a sandwich ELISA format. Polypeptides with the second binding domain directed to CEA bind the recombinant CEA full length protein (rCEA). The negative controls mock and non-relevant protein (NRP) (recombinant PD-L1 protein) indicate a specific binding to rCEA. Polypeptides with the second binding domain directed to CD20 show a similar binding specificity to rCD20. Multispecific binding polypeptides were detected via anti-HA-tag antibodies.

FIG. 2*b* shows FACS analyses demonstrating specific binding of the indicated multispecific binding polypeptides with the first binding domain directed to human CD3 (hCD3) to peripheral blood mononuclear cells (PBMC) isolated from donor blood.

FIG. 2*c* shows FACS analyses demonstrating specific binding of the indicated multispecific binding polypeptides with the first binding domain directed to murine CD3 (mCD3) on murine splenocytes. Polypeptides with the first binding domain directed to mCD3 were not found to recognize hCD3 on PBMCs and vice versa, polypeptides with the first binding domain directed to hCD3 were not found to recognize mCD3 on murine splenocytes.

FIG. 3*a* shows specific killing of MC38 cells expressing the TAA-target CEA in the presence of PBMCs and multispecific binding polypeptides with the first binding domain directed to hCD3 and the second binding domain directed to CEA. Controls with a non-target cell line or a multispecific binding polypeptide with the second binding domain directed to an irrelevant TAA show no specific tumor cell lysis.

FIG. 3*b* shows cytotoxicity for multispecific binding polypeptides with the second binding domain directed to CD20 in a PBMC concentration-dependent manner.

FIG. 3*c* shows cytotoxicity for multispecific binding polypeptides with the second binding domain directed to CD20 in a MBP concentration-dependent manner.

EXAMPLES

The following Examples shall merely illustrate the invention. They shall not be construed, whatsoever, to limit the scope of the invention.

Figure 1:
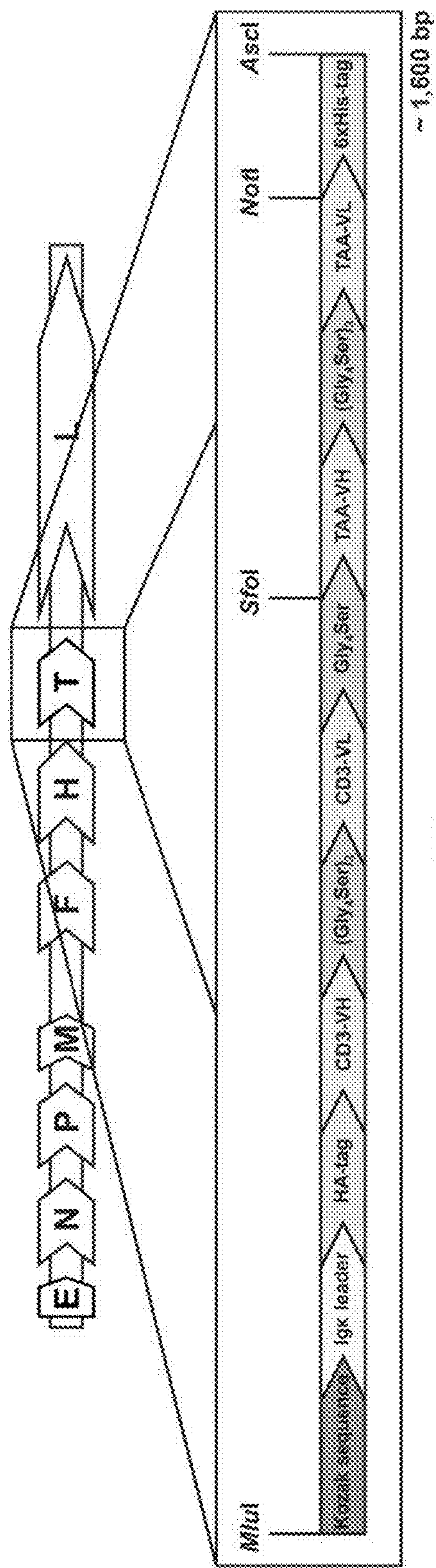
FIG. 1: Schematic of a viral genome of a multispecific binding polypeptide-encoding measles virus (MV-MBP). The 16 kb genomic RNA comprises 6 genes, encoding 8 proteins. This MeV-MBP additionally encodes eGFP upstream of N open reading frame (ORF). The transgene encoding the multispecific binding polypeptide was inserted downstream of the H ORF. The construct comprises approximately 1,600 bp. The exact number of nucleotides is a multiple of six, which is a requirement for measles viruses. Convenient restriction sites were introduced at the indicated positions to easily transfer the construct to different vectors and to exchange the TAA-targeting domain. Both, the variable domains and the scFvs were connected via glycine-serine peptide linkers. The N-terminal HA-tag and C-terminal 6×His-tag are useful for detection and purification purposes. The actual multispecific binding polypeptide sequence is preceded by a Kozak sequence to enhance translation of the transgene RNA transcript. In addition, an Igκ-chain leader sequence is fused to the N-terminus of the multispecific binding polypeptide, directing its expression to the secretory pathway.

Example 1: Production of Virus Encoded Recombinant Multispecific Binding Polypeptides The amplification of the said pcpNSe-multispecific-binding-polypeptide (pcpNSe-MBP) MV (Edmonston B vaccine strain anti-genome with multispecific binding polypeptide gene downstream of H open reading frame (ORF) FIG. 1) was performed in NEB 10-beta bacteria, grown in LB medium (Carl Roth) containing 100 μg/ml ampicillin (Carl Roth). Viral particles were rescued from pcpNSe plasmids and subsequently propagated three times on Vero cells to maximize viral titers. The term rescue of negative-strand RNA viruses is known to the skilled person. Transfection of the plasmids into Vero cells was carried out with FuGENE HD (Promega) according to a standard protocol and cells were incubated at 37° C. for approximately 65 h. When syncytia had formed, virus particles were harvested according to the standard procedure. In brief: supernatant was discarded and cells were scraped into fresh medium. Medium was frozen in liquid nitrogen and thawed once, vortexed and centrifuged. Supernatant containing the viral particles was aliquoted and stored at −80° C. For the production of the multispecific binding polypeptides, $5\times10^6$ Vero cells were seeded in 15 cm dishes and infected with an MOI of 0.03 in 10 ml OptiPRO SFM serum-free medium (Gibco, Invitrogen). Cells were kept at 37° C. for approximately 40 h and then transferred to 32° C. for additional 20 to 25 h. Supernatants were transferred to 50 ml tubes and centrifuged at 2,000×g, 4° C. for 10 min. Supernatants were passed through a 0.22 μm filter (Merck) and multispecific binding polypeptides were purified via the C-terminal 6×His-tag by affinity chromatography according to standard protocol (Qiagen). His-tagged multispecific binding polypeptides were eluted with 500 mM imidazole and subsequently desalted using centrifugal filters (Amicon, Merck).

Example 2: Characterization of Binding Specificity of Recombinant Multispecific Binding Polypeptides Specific binding of the multispecific binding polypeptide to human and murine CD3 and their respective TAA-targets was assessed via FACS analysis and sandwich ELISA, respectively.

(A) ELISA: 96-well plates (Nunc Maxisorp, Thermo Fisher) were coated with 100 μl recombinant human full length CEA (AbD Serotec) or CD20 (Abnova) in PBS [1 μg/ml] and kept at 4° C. for at least 16 h. Wells were washed twice with 200 μl PBS and blocked with 200 μL blocking buffer (PBS supplemented with 5% FCS and 0.05% Tween20 (Biotium)) for 2 h at room temperature. Subsequently wells were washed three times with PBS and incubated with 100 μl sample per well for 2 h at room temperature. Wells were washed four times with PBS-T (PBS supplemented with 0.05% Tween20) and twice with PBS. High affinity anti-HA-biotin antibody (clone BMG-3F10, Roche) was diluted in blocking buffer (1:500). 100 μL antibody solution was added to each well and incubated for 45 min at room temperature. Wells were washed five times with PBS-T and twice with PBS. Streptavidin-horseradish peroxidase (Dianova) was diluted in blocking buffer (1:500) and 100 μL streptavidin solution was added to each well and incubated for 10 min at room temperature. Wells were washed seven times with PBS-T and twice with PBS. 100 μl substrate (1-Step Ultra TMB-ELISA, Thermo Fisher) was added to each well and incubated for 3 to 30 min at room temperature. The reaction was stopped with 100 μl 2N sulfuric acid per well. Absorbance was measured at 450 nm using a microplate reader (Infinite M200 Pro).

Figure 2A:
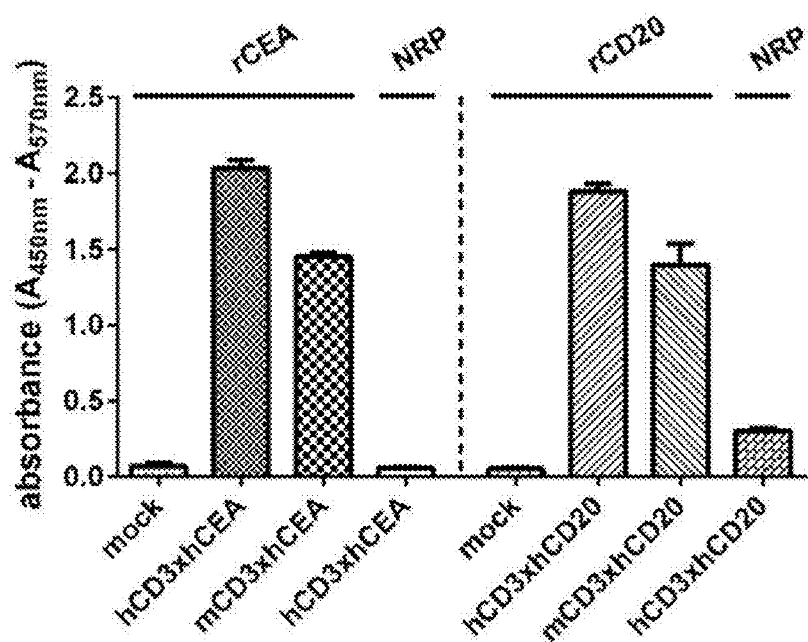
FIGS. 2*a*-2*c* show specific binding of the indicated multispecific binding polypeptides to their respective binding domain targets.

With the described ELISA procedure, said multispecific binding polypeptides with the second binding domain directed to either CEA or CD20 showed specific binding to their respective antigens (FIG. 2*a*). The negative controls mock and non-relevant protein (NRP) (recombinant PD-L1 protein) indicate that binding to the respective antigens occurs in a specific manner.

(B) FACS: Using flow cytometry, cells were discriminated based on their size, structure and surface-expression of particular molecules. We detected cell-bound multispecific binding polypeptides via the C-terminal 6×His-tag and anti-His-tag-FITC antibody (DIA920, Dianova, 10% in 50 μl). Therefore, we labeled $5\times10^5$ human PBMCs from donor blood or murine splenocytes with multispecific binding polypeptides in FACS buffer (PBS supplemented with 1 FCS and 0.05% sodium azide, 10% in 50 μl, 30 min on ice). To reduce unspecific antibody binding during the following staining procedure, Fc receptors present on cells were blocked using Kiovig (Baxter) (for human cells) or mouse BD Fc Block (for mouse CD16/CD32) (5% in 50 μl FACS buffer, 5 min on ice). Cells were washed and resuspended in FACS buffer containing antibodies specific for His-tag, CD3, CD4 and CD8 (BD Biosciences, 5% in 50 μl). After 30 min on ice, cells were washed with FACS buffer and resuspended in 500 μl DAPI [0.2 μg/ml]. Cells were washed and resuspended in 200 to 300 μl FACS buffer and analyzed using an LSR II system (BD Biosciences).

Figure 2B:
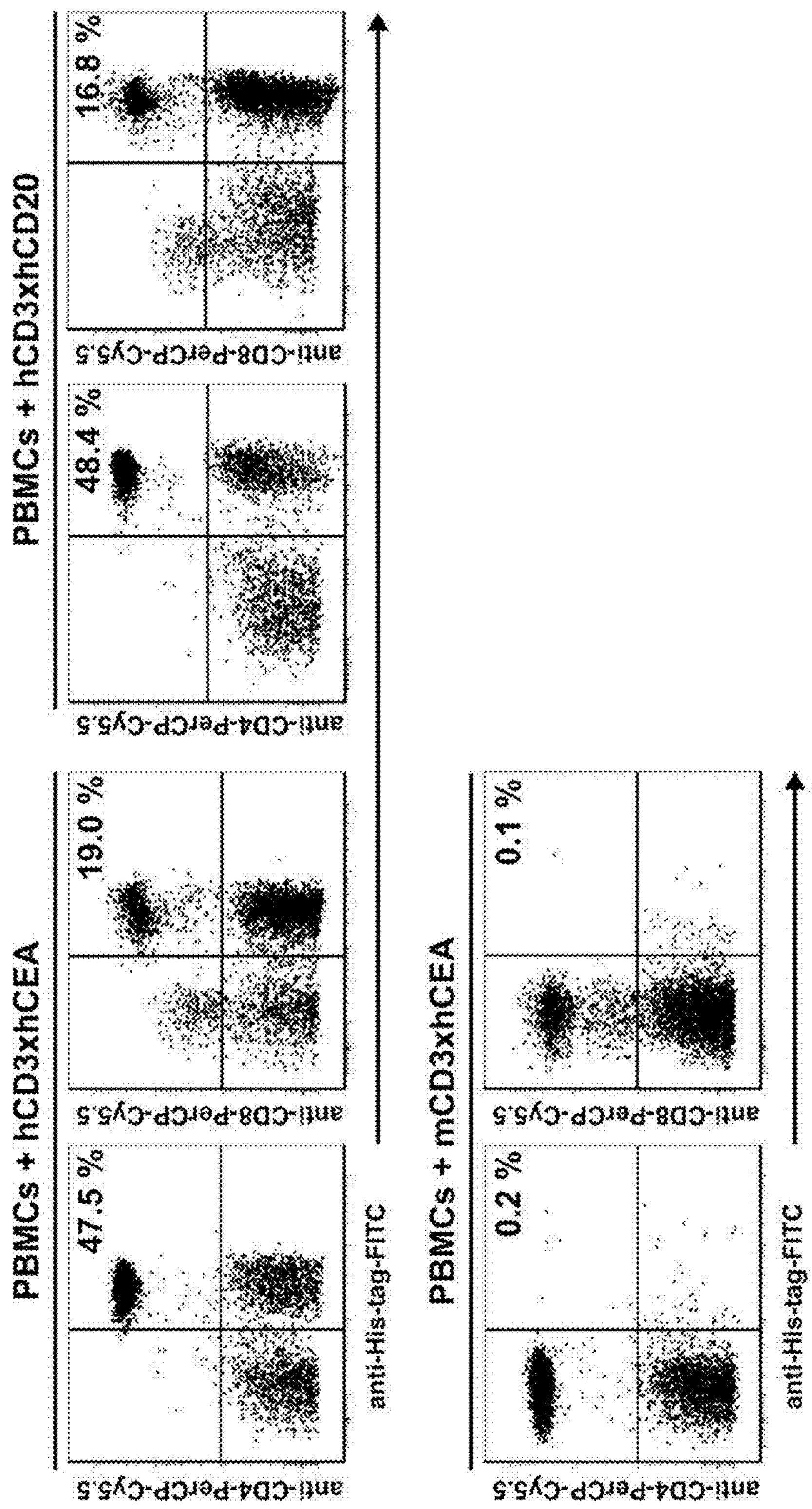
Figure 2C:
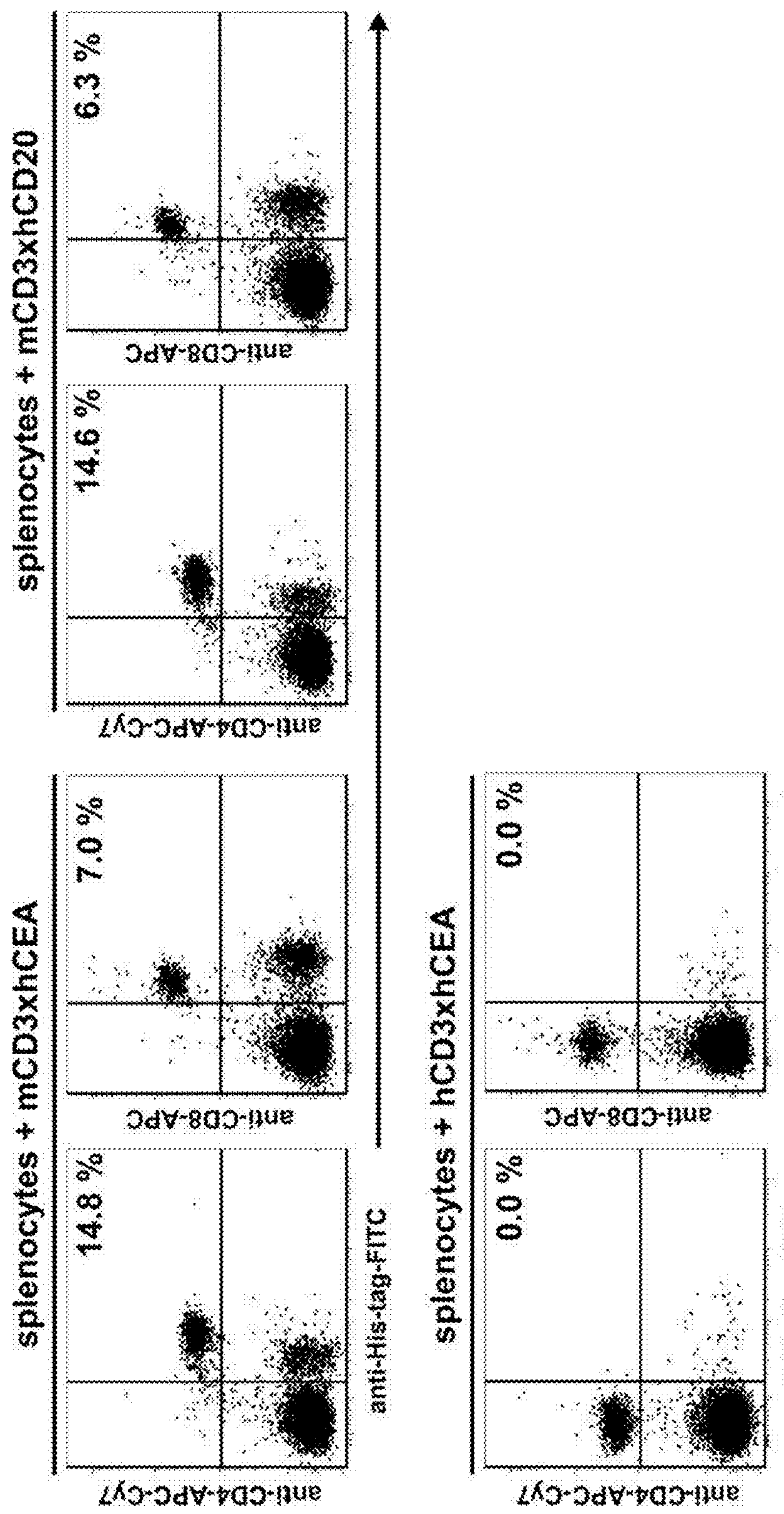

FACS analyses demonstrated specific binding of the multispecific binding polypeptides with the first binding domain directed to human CD3 (hCD3) to peripheral blood mononuclear cells (PBMC) isolated from donor blood (FIG. 2*b*) and to murine CD3 (mCD3) on murine splenocytes (FIG. 2*c*). Polypeptides with the first binding domain directed to mCD3 were not found to recognize hCD3 on PBMCs and vice versa, polypeptides with the first binding domain directed to hCD3 were not found to recognize mCD3 on murine splenocytes.

Example 3: Induction of T Cell Effector Function in Resting Human and Murine T Cells by Recombinant Multispecific Binding Polypeptides We performed lactate dehydrogenase (LDH) release assays to assess the potential of the multispecific binding polypeptides to induce T cell effector functions, directed to specific tumor cells. $5\times10^3$ target cells were cocultured with effector T cells at an effector to target cell ratio (E:T ratio) of 50:1 or various E:T ratios of 50:1, 25:1, 12:1, 6:1, 3:1 and 1:1 on 96-well round-bottom plates in 100 μl RPMI/well in triplicates. Multispecific binding polypeptides were added to each well at a final concentration of 100 ng/ml or at various concentrations of 100 ng/ml, 10 ng/ml, 1 ng/ml, 100 pg/ml, 10 pg/ml and 0 pg/ml. Spontaneous release of LDH from target and effector cells were measured separately, as well as maximum LDH release from target cells only using the provided lysis solution. Cells were cocultured for 24 h at 37° C. Subsequently plates were centrifuged for 4 min at 250×g and 50 μl supernatant was transferred to a 96-well flat-bottom plate. LDH concentration was measured according to the manufacturer's protocol. Tumor-specific T cell-mediated lysis in percent was calculated as:

(experimental release−spontaneous release target cells−spontaneous release effector cells)/(maximum release target cells−spontaneous release target cells)×100

Figure 3A:
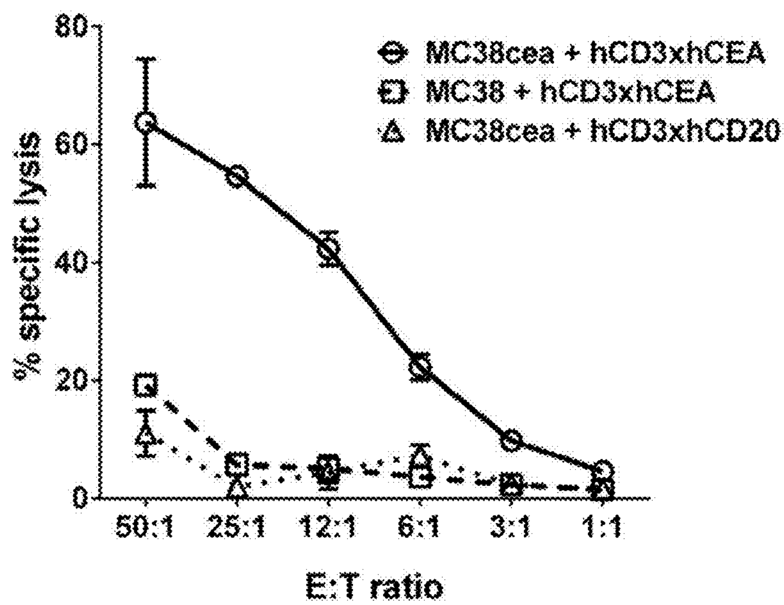
FIGS. 3*a*-3*c* show multispecific binding polypeptides-directed cytotoxicity to target cells mediated by PBMCs.
Figure 3B:
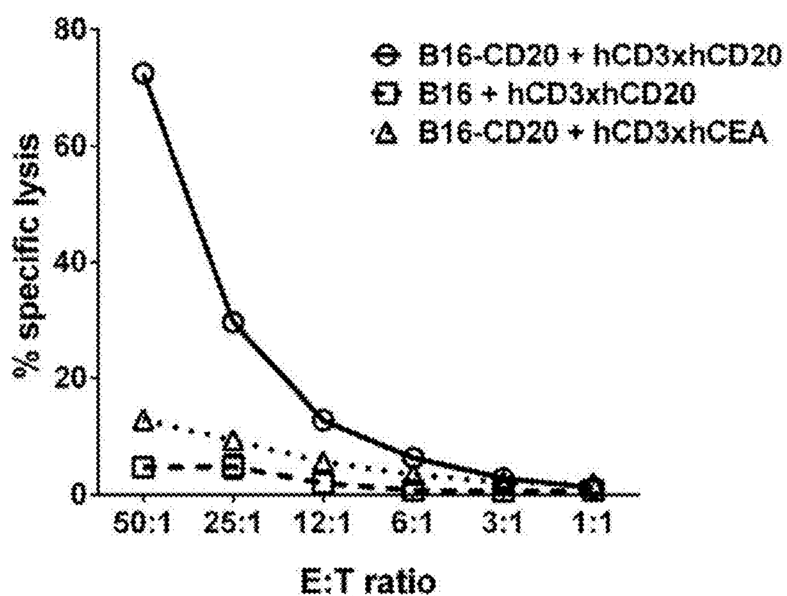
Figure 3C:
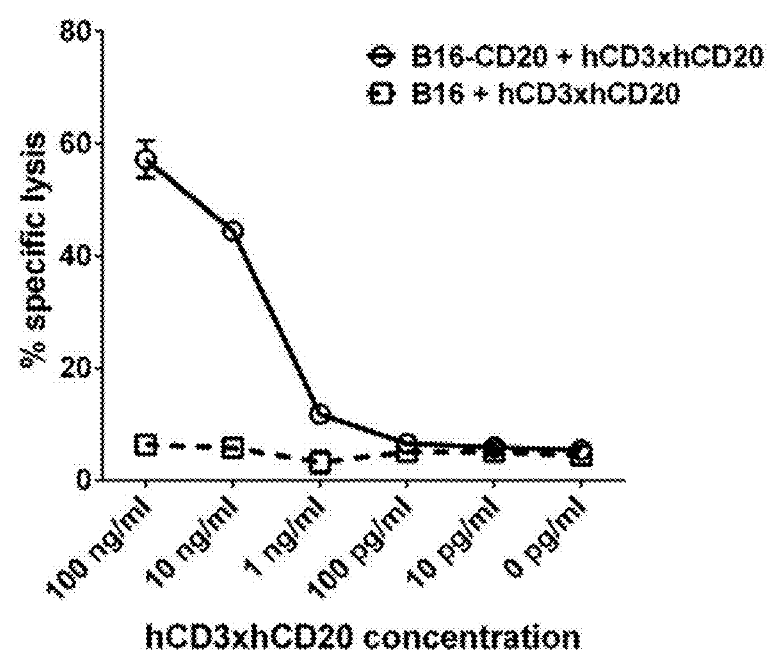

FIGS. 3*a* to *c* demonstrate increased target cell-specific T cell effector function in the presence of the respective multispecific binding polypeptides. Tumor cell killing occurred in a T cell- and multispecific binding polypeptide concentration-dependent manner. The specificity controls in FIGS. 3*a* and 3*b* demonstrate that neither the binding of the multispecific binding polypeptides to the effector cell alone, nor the coculture with the respective target cell line in the presence of a CD3 binding multispecific binding polypeptide were sufficient to induce T cell effector functions.

What is claimed is:

1. A recombinant virus of the family Paramyxoviridae, comprising at least one expressible polynucleotide encoding a multispecific binding polypeptide, said multispecific binding polypeptide comprising:

a) a first binding domain binding to a surface molecule of an immune cell with antitumor activity, and b) a second binding domain binding to a tumor-associated antigen, wherein said recombinant virus is encoded by a polynucleotide comprising the nucleic acid sequence of any one of SEQ ID NO:6-9.

2. The recombinant virus of the family Paramyxoviridae of claim 1, wherein said immune cell with antitumor activity is selected from the group consisting of lymphocyte, T cell and dendritic cell.

3. The recombinant virus of the family Paramyxoviridae of claim 1, wherein said multispecific binding polypeptide further comprises a cytokine.

4. A polynucleotide encoding the recombinant virus of the family Paramyxoviridae according to claim 1.

5. An in vitro method for activating immune cells with antitumor activity in a sample comprising cancer cells and immune cells, comprising a) contacting said sample comprising cancer cells and immune cells with a recombinant virus of the family Paramyxoviridae of claim 1, and b) thereby, activating immune cells with antitumor activity comprised in said sample.

6. A method for treating cancer in a subject afflicted with cancer, comprising a) contacting said subject with a recombinant virus of the family Paramyxoviridae according to claim 1, and b) thereby, treating cancer in a subject afflicted with cancer.

7. The method of claim 6, wherein step a further comprises contacting said subject with a multispecific binding polypeptide.

8. A kit comprising at least the recombinant virus of the family Paramyxoviridae according to claim 1 housed in a container.

* * * * *

SEQUENCE LISTING

```
<160> NUMBER OF SEQ ID NOS: 9

<210> SEQ ID NO 1
<211> LENGTH: 240
<212> TYPE: PRT
<213> ORGANISM: Artificial
<220> FEATURE:
<223> OTHER INFORMATION: artificial construct

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

```
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240


<210> SEQ ID NO 2
<211> LENGTH: 238
<212> TYPE: PRT
<213> ORGANISM: Artificial
<220> FEATURE:
<223> OTHER INFORMATION: artificial construct

<400> SEQUENCE: 2

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser Gly Gly Gly Gly Ser Gly Gly Gly Gly Ser Gly Gly
        115                 120                 125

Gly Gly Ser Asp Ile Gln Met Thr Gln Ser Pro Ser Ser Leu Pro Ala
    130                 135                 140

Ser Leu Gly Asp Arg Val Thr Ile Asn Cys Gln Ala Ser Gln Asp Ile
145                 150                 155                 160

Ser Asn Tyr Leu Asn Trp Tyr Gln Gln Lys Pro Gly Lys Ala Pro Lys
                165                 170                 175

Leu Leu Ile Tyr Tyr Thr Asn Lys Leu Ala Asp Gly Val Pro Ser Arg
```

```
            180                 185                 190

Phe Ser Gly Ser Gly Ser Gly Arg Asp Ser Ser Phe Thr Ile Ser Ser
        195                 200                 205

Leu Glu Ser Glu Asp Ile Gly Ser Tyr Tyr Cys Gln Gln Tyr Tyr Asn
    210                 215                 220

Tyr Pro Trp Thr Phe Gly Pro Gly Thr Lys Leu Glu Ile Lys
225                 230                 235


<210> SEQ ID NO 3
<211> LENGTH: 242
<212> TYPE: PRT
<213> ORGANISM: Artificial
<220> FEATURE:
<223> OTHER INFORMATION: artificial construct

<400> SEQUENCE: 3

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Cys Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Asn Val Leu Thr Gln Ser Pro Ala
    130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Leu Trp Ile Tyr Ser Thr Ser Asn Leu Ala Ser Gly Val
            180                 185                 190

Pro Ala Arg Phe Ser Gly Ser Gly Ser Gly Thr Ser Tyr Ser Leu Thr
        195                 200                 205

Ile Ser Arg Met Glu Ala Glu Asp Ala Ala Thr Tyr Tyr Cys Gln Gln
    210                 215                 220

Arg Ser Ser Tyr Pro Leu Thr Phe Gly Cys Gly Thr Lys Leu Glu Leu
225                 230                 235                 240

Lys Arg


<210> SEQ ID NO 4
<211> LENGTH: 248
<212> TYPE: PRT
<213> ORGANISM: Artificial
<220> FEATURE:
<223> OTHER INFORMATION: artificial construct

<400> SEQUENCE: 4

Gln Val Gln Leu Val Gln Ser Gly Ala Glu Leu Val Lys Pro Gly Ala
```

```
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ala Gln Leu Arg Pro Asn Tyr Trp Tyr Phe Asp Val Trp Gly
            100                 105                 110

Ala Gly Thr Thr Val Thr Val Ser Lys Ile Ser Gly Gly Gly Gly Ser
        115                 120                 125

Gly Gly Gly Gly Ser Gly Gly Gly Gly Ser Gly Gly Ser Ser Asp Ile
    130                 135                 140

Val Leu Ser Gln Ser Pro Ala Ile Leu Ser Ala Ser Pro Gly Glu Lys
145                 150                 155                 160

Val Thr Met Thr Cys Arg Ala Ser Ser Ser Val Ser Tyr Met His Trp
                165                 170                 175

Tyr Gln Gln Lys Pro Gly Ser Ser Pro Lys Pro Trp Ile Tyr Ala Thr
            180                 185                 190

Ser Asn Leu Ala Ser Gly Val Pro Ala Arg Phe Ser Gly Ser Gly Ser
        195                 200                 205

Gly Thr Ser Tyr Ser Leu Thr Ile Ser Arg Val Glu Ala Glu Asp Ala
    210                 215                 220

Ala Thr Tyr Tyr Cys Gln Gln Trp Ile Ser Asn Pro Pro Thr Phe Gly
225                 230                 235                 240

Ala Gly Thr Lys Leu Glu Leu Lys
                245
```

<210> SEQ ID NO 5
<211> LENGTH: 1596
<212> TYPE: DNA
<213> ORGANISM: Artificial
<220> FEATURE:
<223> OTHER INFORMATION: artificial construct

<400> SEQUENCE: 5

```
atggagacag acacactcct gctatgggta ctgctgctct gggttccagg ttccactggt     60

gactatccat atgatgttcc agattatgct caggtgcagc ttcagcaatc cggggcagaa    120

ctggctagac ctggggctag cgtcaagatg tcctgcaaag cctccggata tactttcaca    180

cgctatacca tgcattgggt caaacaacga ccaggtcaag gcctcgaatg gatcggctat    240

atcaatccga gtaggggata caccaactac aaccagaagt tcaaggataa ggctacactg    300

acaaccgaca agtcatcttc aacggcctat atgcagcttt ccagcctgac aagcgaggat    360

tctgccgttt actactgtgc gcggtactat gacgatcact actgcttgga ctattggggc    420

caaggtacca ctttgaccgt atctagcgga ggcggcggga gtggcggagg tgggagtggc    480

ggtggtggga gccagattgt gctcactcag tcccctgcaa tcatgtcagc aagtcctggg    540

gagaaagtga ctatgacttg ttccgctagc agcagtgtga gctacatgaa ctggtaccag    600

cagaagtctg gaacctcacc caaacggtgg atctacgaca catcaaaact ggccagtggg    660
```

```
gttccagcgc attttcgtgg gtctggcagc ggaacaagct attccctgac gatttccggg    720
atggaagccg aggatgcagc cacctattac tgccagcagt ggagctcaaa tccctttacc    780
ttcggatctg gcactaagct ggagataaat ggtggcggag gctctggcgc ccaggtgaaa    840
ctgcagcagt ctggggcaga acttgtgagg tcagggacct cagtcaagtt gtcctgcaca    900
gcttctggct tcaacattaa agactcctat atgcactggt tgaggcaggg gcctgaacag    960
tgcctcgagt ggattggatg gattgatcct gagaatggtg atactgaata tgccccgaag   1020
ttccagggca aggccacttt tactacagac acatcctcca acacagccta cctgcagctc   1080
agcagcctga catctgagga cactgccgtc tattattgta atgaggggac tccgactggg   1140
ccgtactact ttgactactg gggccaaggg accacggtca ccgtctcctc aggtggaggc   1200
ggttcaggcg gaggtggctc tggcggtggc ggatcagaaa atgtgctcac ccagtctcca   1260
gcaatcatgt ctgcatctcc aggggagaag gtcaccataa cctgcagtgc cagctcaagt   1320
gtaagttaca tgcactggtt ccagcagaag ccaggcactt ctcccaaact ctggatttat   1380
agcacatcca acctggcttc tggagtccct gctcgcttca gtggcagtgg atctgggacc   1440
tcttactctc tcacaatcag ccgaatggag gctgaagatg ctgccactta ttactgccag   1500
caaaggagta gttacccact cacgttcggt tgtggcacca agctcgagct gaaacgggcg   1560
gccgccagag gctctcacca ccatcatcac cactag                             1596
```

<210> SEQ ID NO 6
<211> LENGTH: 21315
<212> TYPE: DNA
<213> ORGANISM: Artificial
<220> FEATURE:
<223> OTHER INFORMATION: artificial construct

<400> SEQUENCE: 6

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggacatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
```

```
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagcagatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat cccccaaga   2100
aatctccagg catcaagcac tgggctacag tgtcattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc ttcattgaca ggtggtgcaa cccaatgtgc tcgaaagtca   2580
ccctcggaac catcagggcc aggtgcacct gcggggaacg tccccgagtg tgtgagcaat   2640
gccgcactga tacaggagtg gacacccgaa tctggcacca caatctcccc gagatcccag   2700
aataatgaag aagggggaga ccattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctgg tgaagataat aatgaagtag ctacagctca acttacctgc caaccccatg   3360
ccagtcgacc caactagcgt acgatgacgt cctagtacaa cctaaatcca ttataaaaaa   3420
cttaggagca aagtgattgc ctcccaagtt ccacaatgac agagatctac gacttcgaca   3480
```

-continued

```
agtcggcatg ggacatcaaa gggtcgatcg ctccgataca acccaccacc tacagtgatg   3540
gcaggctggt gccccaggtc agagtcatag atcctggtct aggcgacagg aaggatgaat   3600
gctttatgta catgtttctg ctggggggttg ttgaggacag cgattcccta gggcctccaa   3660
tcgggcgagc atttgggtcc ctgcccttag gtgttggcag atccacagca aagcccgaaa   3720
aactcctcaa agaggccact gagcttgaca tagttgttag acgtacagca gggctcaatg   3780
aaaaactggt gttctacaac aacaccccac taactctcct cacaccttgg agaaaggtcc   3840
taacaacagg gagtgtcttc aacgcaaacc aagtgtgcaa tgcggttaat ctgataccgc   3900
tcgatacccc gcagaggttc cgtgttgttt atatgagcat cacccgtctt tcggataacg   3960
ggtattacac cgttcctgga agaatgctgg aattcagatc ggtcaatgca gtggccttca   4020
acctgctggt gaccctagg attgacaagg cgataggccc tgggaagatc atcgacaata   4080
cagagcaact tcctgaggca acatttatgg tccacatcgg gaacttcagg agaaagaaga   4140
gtgaagtcta ctctgccgat tattgcaaaa tgaaaatcga aaagatgggc ctggtttttg   4200
cacttggtgg gatagggggc accagtcttc acattagaag cacaggcaaa atgagcaaga   4260
ctctccatgc acaactcggg ttcaagaaga ccttatgtta cccgctgatg gatatcaatg   4320
aagaccttaa tcgattactc tggaggagca gatgcaagat agtaagaatc caggcagttt   4380
tgcagccatc agttcctcaa gaattccgca tttacgacga cgtgatcata aatgatgacc   4440
aaggactatt caaagttctg tagaccgtag tgcccagcaa tgcccgaaaa cgacccccct   4500
cacaatgaca gccagaaggc ccggacaaaa aagccccctc cgaaagactc cacggaccaa   4560
gcgagaggcc agccagcagc cgacggcaag cgcgaacacc aggcggcccc agcacagaac   4620
agccctgaca caaggccacc accagccacc ccaatctgca tcctcctcgt gggacccccg   4680
aggaccaacc cccaaggctg cccccgatcc aaaccaccaa ccgcatcccc accacccccg   4740
ggaaagaaac ccccagcaat tggaaggccc ctccccctct tcctcaacac aagaactcca   4800
caaccgaacc gcacaagcga ccgaggtgac ccaaccgcag gcatccgact ccctagacag   4860
atcctctctc cccggcaaac taaacaaaac ttagggccaa ggaacataca cacccaacag   4920
aacccagacc ccggcccacg gcgccgcgcc cccaaccccc gacaaccaga gggagccccc   4980
aaccaatccc gccggctccc ccggtgccca caggcaggga caccaacccc cgaacagacc   5040
cagcacccaa ccatcgacaa tccaagacgg gggggccccc ccaaaaaaag gcccccaggg   5100
gccgacagcc agcaccgcga ggaagcccac ccaccccaca cacgaccacg gcaaccaaac   5160
cagaacccag accaccctgg gccaccagct cccagactcg gccatcaccc cgcagaaagg   5220
aaaggccaca acccgcgcac cccagccccg atccggcggg gagccaccca acccgaacca   5280
gcacccaaga gcgatccccg aaggaccccc gaaccgcaaa ggacatcagt atcccacagc   5340
ctctccaagt cccccggtct cctcctcttc tcgaagggac caaaagatca atccaccaca   5400
cccgacgaca ctcaactccc caccccctaaa ggagacaccg ggaatcccag aatcaagact   5460
catccaatgt ccatcatggg tctcaaggtg aacgtctctg ccatattcat ggcagtactg   5520
ttaactctcc aaacacccac cggtcaaatc cattggggca atctctctaa gatagggggtg   5580
gtaggaatag gaagtgcaag ctacaaagtt atgactcgtt ccagccatca atcattagtc   5640
ataaaattaa tgcccaatat aactctcctc aataactgca cgagggtaga gattgcagaa   5700
tacaggagac tactgagaac agttttggaa ccaattagag atgcacttaa tgcagtgacc   5760
cagaatataa gaccggttca gagtgtagct tcaagtagga gacacaagag atttgcggga   5820
gtagtcctgg caggtgcggc cctaggcgtt gccacagctg ctcagataac agccggcatt   5880
```

```
gcacttcacc agtccatgct gaactctcaa gccatcgaca atctgagagc gagcctggaa   5940
actactaatc aggcaattga ggcaatcaga caagcagggc aggagatgat attggctgtt   6000
cagggtgtcc aagactacat caataatgag ctgataccgt ctatgaacca actatcttgt   6060
gatttaatcg gccagaagct cgggctcaaa ttgctcagat actatacaga aatcctgtca   6120
ttatttggcc ccagcttacg ggaccccata tctgcggaga tatctatcca ggctttgagc   6180
tatgcgcttg gaggagacat caataaggtg ttagaaaagc tcggatacag tggaggtgat   6240
ttactgggca tcttagagag cagaggaata aaggcccgga taactcacgt cgacacagag   6300
tcctacttca ttgtcctcag tatagcctat ccgacgctgt ccgagattaa gggggtgatt   6360
gtccaccggc tagagggggt ctcgtacaac ataggctctc aagagtggta taccactgtg   6420
cccaagtatg ttgcaaccca agggtacctt atctcgaatt ttgatgagtc atcgtgtact   6480
ttcatgccag aggggactgt gtgcagccaa aatgccttgt acccgatgag tcctctgctc   6540
caagaatgcc tccgggggtc caccaagtcc tgtgctcgta cactcgtatc cgggtctttt   6600
gggaaccggt tcattttatc acaagggaac ctaatagcca attgtgcatc aatcctttgc   6660
aagtgttaca caacaggaac gatcattaat caagaccctg acaagatcct aacatacatt   6720
gctgccgatc actgcccggt agtcgaggtg aacggcgtga ccatccaagt cgggagcagg   6780
aggtatccag acgctgtgta cttgcacaga attgacctcg gtcctcccat atcattggag   6840
aggttggacg tagggacaaa tctggggaat gcaattgcta agttggagga tgccaaggaa   6900
ttgttggagt catcggacca gatattgagg agtatgaaag gtttatcgag cactagcata   6960
gtctacatcc tgattgcagt gtgtcttgga gggttgatag ggatccccgc tttaatatgt   7020
tgctgcaggg ggcgttgtaa caaaaaggga gaacaagttg gtatgtcaag accaggccta   7080
aagcctgatc ttacgggaac atcaaaatcc tatgtaaggt cgctctgatc ctctacaact   7140
cttgaaacac aaatgtccca caagtctcct cttcgtcatc aagcaaccac cgcacccagc   7200
atcaagccca cctgaaatta tctccggttt ccctctggcc gaacaatatc ggtagttaat   7260
taaaacttag ggtgcaagat catccacaat gtcaccacaa cgagaccgga taaatgcctt   7320
ctacaaagat aacccccatc ccaagggaag taggatagtc attaacagag aacatcttat   7380
gattgataga ccttatgttt tgctggctgt tctgtttgtc atgtttctga gcttgatcgg   7440
gttgctagcc attgcaggca ttagacttca tcgggcagcc atctacaccg cagagatcca   7500
taaaagcctc agcaccaatc tagatgtaac taactcaatc gagcatcagg tcaaggacgt   7560
gctgacacca ctcttcaaaa tcatcggtga tgaagtgggc ctgaggacac ctcagagatt   7620
cactgaccta gtgaaattca tctctgacaa gattaaattc cttaatccgg atagggagta   7680
cgacttcaga gatctcactt ggtgtatcaa cccgccagag agaatcaaat tggattatga   7740
tcaatactgt gcagatgtgg ctgctgaaga gctcatgaat gcattggtga actcaactct   7800
actggagacc agaacaacca atcagttcct agctgtctca aagggaaact gctcagggcc   7860
cactacaatc agaggtcaat tctcaaacat gtcgctgtcc ctgttagact tgtatttagg   7920
tcgaggttac aatgtgtcat ctatagtcac tatgacatcc cagggaatgt atgggggaac   7980
ttacctagtg gaaaagccta atctgagcag caaaaggtca gagttgtcac aactgagcat   8040
gtaccgagtg tttgaagtag gtgttatcag aaatccgggt ttgggggctc cggtgttcca   8100
tatgacaaac tatcttgagc aaccagtcag taatgatctc agcaactgta tggtggcttt   8160
gggggagctc aaactcgcag ccctttgtca cggggaagat tctatcacaa ttccctatca   8220
```

-continued

```
gggatcaggg aaaggtgtca gcttccagct cgtcaagcta ggtgtctgga aatccccaac   8280
cgacatgcaa tcctgggtcc ccttatcaac ggatgatcca gtgatagaca ggctttacct   8340
ctcatctcac agaggtgtta tcgctgacaa ccaagcaaaa tgggctgtcc cgacaacacg   8400
aacagatgac aagttgcgaa tggagacatg cttccaacag gcgtgtaagg gtaaaatcca   8460
agcactctgc gagaatcccg agtgggcacc attgaaggat aacaggattc cttcatacgg   8520
ggtcttgtct gttgatctga gtctgacagt tgagcttaaa atcaaaattg cttcgggatt   8580
cgggccattg atcacacacg gttcagggat ggacctatac aaatccaacc acaacaatgt   8640
gtattggctg actatcccgc caatgaagaa cctagcctta ggtgtaatca acacattgga   8700
gtggataccg agattcaagg ttagtcccta cctcttcact gtcccaatta aggaagcagg   8760
cggagactgc catgccccaa catacctacc tgcggaggtg gatggtgatg tcaaactcag   8820
ttccaatctg gtgattctac ctggtcaaga tctccaatat gttttggcaa cctacgatac   8880
ttccagggtt gaacatgctg tggtttatta cgtttacagc ccaagccgct cattttctta   8940
cttttatcct tttaggttgc ctataaaggg ggtccccatc gaattacaag tggaatgctt   9000
cacatgggac caaaaactct ggtgccgtca cttctgtgtg cttgcggact cagaatctgg   9060
tggacatatc actcactctg ggatggtggg catgggagtc agctgcacag tcacccggga   9120
agatggaacc aatcgcagat agggctgcta gtgaaccaat cacatgatgt cacccagaca   9180
tcaggcatac ccactagtcc tccatcattg ttataaaaaa cttaggaacc aggtccacac   9240
agctcgagtc gcgcgtgcca ccatggagac agacacactc ctgctatggg tactgctgct   9300
ctgggttcca ggttccactg gtgactatcc atatgatgtt ccagattatg ctcaggtgca   9360
gcttcagcaa tccggggcag aactggctag acctggggct agcgtcaaga tgtcctgcaa   9420
agcctccgga tatactttca cacgctatac catgcattgg gtcaaacaac gaccaggtca   9480
aggcctcgaa tggatcggct atatcaatcc gagtagggga tacaccaact acaaccagaa   9540
gttcaaggat aaggctacac tgacaaccga caagtcatct tcaacggcct atatgcagct   9600
ttccagcctg acaagcgagg attctgccgt ttactactgt gcgcggtact atgacgatca   9660
ctactgcttg gactattggg gccaaggtac cactttgacc gtatctagcg gaggcggcgg   9720
gagtggcgga ggtgggagtg gcggtggtgg gagccagatt gtgctcactc agtcccctgc   9780
aatcatgtca gcaagtcctg gggagaaagt gactatgact tgttccgcta gcagcagtgt   9840
gagctacatg aactggtacc agcagaagtc tggaacctca cccaaacggt ggatctacga   9900
cacatcaaaa ctggccagtg ggttccagc gcattttcgt gggtctggca gcggaacaag   9960
ctattccctg acgatttccg ggatggaagc cgaggatgca gccacctatt actgccagca  10020
gtggagctca aatcccttta ccttcggatc tggcactaag ctggagataa atggtggcgg  10080
aggctctggc gcccaggtga aactgcagca gtctggggca gaacttgtga ggtcagggac  10140
ctcagtcaag ttgtcctgca cagcttctgg cttcaacatt aaagactcct atatgcactg  10200
gttgaggcag gggcctgaac agtgcctcga gtggattgga tggattgatc ctgagaatgg  10260
tgatactgaa tatgccccga agttccaggg caaggccact tttactacag acacatcctc  10320
caacacagcc tacctgcagc tcagcagcct gacatctgag gacactgccg tctattattg  10380
taatgagggg actccgactg ggccgtacta ctttgactac tggggccaag ggaccacggt  10440
caccgtctcc tcaggtggag gcggttcagg cggaggtggc tctggcggtg gcggatcaga  10500
aaatgtgctc acccagtctc cagcaatcat gtctgcatct ccaggggaga aagtcaccat  10560
aacctgcagt gccagctcaa gtgtaagtta catgcactgg ttccagcaga agccaggcac  10620
```

```
ttctcccaaa ctctggattt atagcacatc caacctggct tctggagtcc ctgctcgctt  10680
cagtggcagt ggatctggga cctcttactc tctcacaatc agccgaatgg aggctgaaga  10740
tgctgccact tattactgcc agcaaaggag tagttaccca ctcacgttcg gttgtggcac  10800
caagctcgag ctgaaacggg cggccgccag aggctctcac caccatcatc accactaggc  10860
gcgcgttcta gtgtgaaata gacatcagaa ttaagaaaaa cgtagggtcc aagtggttcc  10920
ccgttatgga ctcgctatct gtcaaccaga tcttataccc tgaagttcac ctagatagcc  10980
cgatagttac caataagata gtagccatcc tggagtatgc tcgagtccct cacgcttaca  11040
gcctggagga ccctacactg tgtcagaaca tcaagcaccg cctaaaaaac ggattttcca  11100
accaaatgat tataaacaat gtggaagttg ggaatgtcat caagtccaag cttaggagtt  11160
atccggccca ctctcatatt ccatatccaa attgtaatca ggatttattt aacatagaag  11220
acaaagagtc aacgaggaag atccgtgaac tcctcaaaaa ggggaattcg ctgtactcca  11280
aagtcagtga taaggttttc caatgcttaa gggacactaa ctcacggctt ggcctaggct  11340
ccgaattgag ggaggacatc aaggagaaag ttattaactt gggagtttac atgcacagct  11400
cccagtggtt tgagcccttt ctgttttggt ttacagtcaa gactgagatg aggtcagtga  11460
ttaaatcaca aacccatact tgccatagga ggagacacac acctgtattc ttcactggta  11520
gttcagttga gttgctaatc tctcgtgacc ttgttgctat aatcagtaaa gagtctcaac  11580
atgtatatta cctgacattt gaactggttt tgatgtattg tgatgtcata gaggggaggt  11640
taatgacaga gaccgctatg actattgatg ctaggtatac agagcttcta ggaagagtca  11700
gatacatgtg gaaactgata gatggtttct tccctgcact cgggaatcca acttatcaaa  11760
ttgtagccat gctggagcct ctttcacttg cttacctgca gctgagggat ataacagtag  11820
aactcagagg tgctttcctt aaccactgct ttactgaaat acatgatgtt cttgaccaaa  11880
acgggttttc tgatgaaggt acttatcatg agttaattga agctctagat tacattttca  11940
taactgatga catacatctg acaggggaga ttttctcatt tttcagaagt ttcggccacc  12000
ccagacttga agcagtaacg gctgctgaaa atgttaggaa atacatgaat cagcctaaag  12060
tcattgtgta tgagactctg atgaaaggtc atgccatatt ttgtggaatc ataatcaacg  12120
gctatcgtga caggcacgga ggcagttggc caccgctgac cctcccccctg catgctgcag  12180
acacaatccg gaatgctcaa gcttcaggtg atgggttaac acatgagcag tgcgttgata  12240
actggaaatc ttttgctgga gtgaaatttg gctgctttat gcctcttagc ctggatagtg  12300
atctgacaat gtacctaaag gacaaggcac ttgctgctct ccaaagggaa tgggattcag  12360
tttacccgaa agagttcctg cgttacgacc ctcccaaggg aaccgggtca cggaggcttg  12420
tagatgtttt ccttaatgat tcgagctttg acccatatga tgtgataatg tatgttgtaa  12480
gtggagctta cctccatgac cctgagttca acctgtctta cagcctgaaa gaaaaggaga  12540
tcaaggaaac aggtagactt tttgctaaaa tgacttacaa aatgagggca tgccaagtga  12600
ttgctgaaaa tctaatctca aacgggattg gcaaatattt taaggacaat gggatggcca  12660
aggatgagca cgatttgact aaggcactcc acactctagc tgtctcagga gtccccaaag  12720
atctcaaaga aagtcacagg ggggggccag tcttaaaaac ctactcccga agcccagtcc  12780
acacaagtac caggaacgtg agagcagcaa aagggtttat agggttccct caagtaattc  12840
ggcaggacca agacactgat catccggaga atatggaagc ttacgagaca gtcagtgcat  12900
ttatcacgac tgatctcaag aagtactgcc ttaattggag atatgagacc atcagcttgt  12960
```

```
ttgcacagag gctaaatgag atttacggat tgccctcatt tttccagtgg ctgcataaga  13020
ggcttgagac ctctgtcctg tatgtaagtg accctcattg cccccccgac cttgacgccc  13080
atatcccgtt atataaagtc cccaatgatc aaatcttcat taagtaccct atgggaggta  13140
tagaagggta ttgtcagaag ctgtggacca tcagcaccat tccctatcta tacctggctg  13200
cttatgagag cggagtaagg attgcttcgt tagtgcaagg ggacaatcag accatagccg  13260
taacaaaaag ggtacccagc acatggccct acaaccttaa gaaacgggaa gctgctagag  13320
taactagaga ttactttgta attcttaggc aaaggctaca tgatattggc catcacctca  13380
aggcaaatga gacaattgtt tcatcacatt tttttgtcta ttcaaaagga atatattatg  13440
atgggctact tgtgtcccaa tcactcaaga gcatcgcaag atgtgtattc tggtcagaga  13500
ctatagttga tgaaacaagg gcagcatgca gtaatattgc tacaacaatg gctaaaagca  13560
tcgagagagg ttatgaccgt taccttgcat attccctgaa cgtcctaaaa gtgatacagc  13620
aaattctgat ctctcttggc ttcacaatca attcaaccat gacccgggat gtagtcatac  13680
ccctcctcac aaacaacgac ctcttaataa ggatggcact gttgcccgct cctattgggg  13740
ggatgaatta tctgaatatg agcaggctgt ttgtcagaaa catcggtgat ccagtaacat  13800
catcaattgc tgatctcaag agaatgattc tcgcctcact aatgcctgaa gagaccctcc  13860
atcaggtaat gacacaacaa ccgggggact cttcattcct agactgggct agcgacccctt  13920
actcagcaaa tcttgtatgt gtccagagca tcactagact cctcaagaac ataactgcaa  13980
ggtttgtcct gatccatagt ccaaacccaa tgttaaaagg attattccat gatgacagta  14040
aagaagagga cgagggactg gcggcattcc tcatggacag gcatattata gtacctaggg  14100
cagctcatga aatcctggat catagtgtca caggggcaag agagtctatt gcaggcatgc  14160
tggataccac aaaaggcttg attcgagcca gcatgaggaa gggggggttta acctctcgag  14220
tgataaccag attgtccaat tatgactatg aacaattcag agcagggatg gtgctattga  14280
caggaagaaa gagaaatgtc ctcattgaca aagagtcatg ttcagtgcag ctggcgagag  14340
ctctaagaag ccatatgtgg gcgaggctag ctcgaggacg gcctatttac ggccttgagg  14400
tccctgatgt actagaatct atgcgaggcc accttattcg gcgtcatgag acatgtgtca  14460
tctgcgagtg tggatcagtc aactacggat ggtttttgt cccctcgggt tgccaactgg  14520
atgatattga caaggaaaca tcatccttga gagtcccata tattggttct accactgatg  14580
agagaacaga catgaagctt gccttcgtaa gagccccaag tcgatccttg cgatctgctg  14640
ttagaatagc aacagtgtac tcatgggctt acggtgatga tgatagctct tggaacgaag  14700
cctggttgtt ggctaggcaa agggccaatg tgagcctgga ggagctaagg gtgatcactc  14760
ccatctcaac ttcgactaat ttagcgcata ggttgaggga tcgtagcact caagtgaaat  14820
actcaggtac atcccttgtc cgagtggcga ggtataccac aatctccaac gacaatctct  14880
catttgtcat atcagataag aaggttgata ctaactttat ataccaacaa ggaatgcttc  14940
tagggttggg tgttttagaa acattgtttc gactcgagaa agataccgga tcatctaaca  15000
cggtattaca tcttcacgtc gaaacagatt gttgcgtgat cccgatgata gatcatccca  15060
ggatacccag ctcccgcaag ctagagctga gggcagagct atgtaccaac ccattgatat  15120
atgataatgc acctttaatt gacagagatg caacaaggct atacacccag agccatagga  15180
ggcaccttgt ggaatttgtt acatggtcca caccccaact atatcacatt ttagctaagt  15240
ccacagcact atctatgatt gacctggtaa caaaatttga gaaggaccat atgaatgaaa  15300
tttcagctct catagggat gacgatatca atagtttcat aactgagttt ctgctcatag  15360
```

```
agccaagatt attcactatc tacttgggcc agtgtgcggc catcaattgg gcatttgatg  15420
tacattatca tagaccatca gggaaatatc agatgggtga gctgttgtca tcgttccttt  15480
ctagaatgag caaaggagtg tttaaggtgc ttgtcaatgc tctaagccac ccaaagatct  15540
acaagaaatt ctggcattgt ggtattatag agcctatcca tggtccttca cttgatgctc  15600
aaaacttgca cacaactgtg tgcaacatgg tttacacatg ctatatgacc tacctcgacc  15660
tgttgttgaa tgaagagtta gaagagttca catttctctt gtgtgaaagc gacgaggatg  15720
tagtaccgga cagattcgac aacatccagg caaaacactt atgtgttctg gcagatttgt  15780
actgtcaacc agggacctgc ccaccaattc aaggtctaag accggtagag aaatgtgcag  15840
ttctaaccga ccatatcaag gcagaggcta tgttatctcc agcaggatct tcgtggaaca  15900
taaatccaat tattgtagac cattactcat gctccctgac ttatctccgg cgaggatcga  15960
tcaaacagat aagattgaga gttgatccag gattcatttt cgacgccctc gctgaggtaa  16020
atgtcagtca gccaaagatc ggcagcaaca acatctcaaa tatgagcatc aaggctttca  16080
gacccccaca cgatgatgtt gcaaaattgc tcaaagatat caacacaagc aagcacaatc  16140
ttcccatttc agggggcaat ctcgccaatt atgaaatcca tgctttccgc agaatcgggt  16200
tgaactcatc tgcttgctac aaagctgttg agatatcaac attaattagg agatgccttg  16260
agccagggga ggacggcttg ttcttgggtg agggatcggg ttctatgttg atcacttata  16320
aggagatact taaactaagc aagtgcttct ataatagtgg ggtttccgcc aattctagat  16380
ctggtcaaag ggaattagca ccctatccct ccgaagttgg ccttgtcgaa cacagaatgg  16440
gagtaggtaa tattgtcaaa gtgctcttta acgggaggcc cgaagtcacg tgggtaggca  16500
gtgtagattg cttcaatttc atagttagta atatccctac ctctagtgtg gggtttatcc  16560
attcagatat agagaccttg cctgacaaag atactataga gaagctagag gaattggcag  16620
ccatcttatc gatggctctg ctcctgggca aaataggatc aatactggtg attaagctta  16680
tgcctttcag cggggatttt gttcagggat ttataagtta tgtagggtct cattatagag  16740
aagtgaacct tgtataccct agatacagca acttcatctc tactgaatct tatttggtta  16800
tgacagatct caaggctaac cggctaatga atcctgaaaa gattaagcag cagataattg  16860
aatcatctgt gaggacttca cctggactta taggtcacat cctatccatt aagcaactaa  16920
gctgcataca agcaattgtg ggagacgcag ttagtagagg tgatatcaat cctactctga  16980
aaaaacttac acctatagag caggtgctga tcaattgcgg gttggcaatt aacggaccta  17040
agctgtgcaa agaattgatc caccatgatg ttgcctcagg gcaagatgga ttgcttaatt  17100
ctatactcat cctctacagg gagttggcaa gattcaaaga caaccaaaga agtcaacaag  17160
ggatgttcca cgcttacccc gtattggtaa gtagcaggca acgagaactt atatctagga  17220
tcacccgcaa attctggggg cacattcttc tttactccgg gaacaaaaag ttgataaata  17280
agtttatcca gaatctcaag tccggctatc tgatactaga cttacaccag aatatcttcg  17340
ttaagaatct atccaagtca gagaaacaga ttattatgac ggggggtttg aaacgtgagt  17400
gggtttttaa ggtaacagtc aaggagacca aagaatggta taagttagtc ggatacagtg  17460
ccctgattaa ggactaattg gttgaactcc ggaaccctaa tcctgcccta ggtggttagg  17520
cattatttgc aatatattaa agaaaacttt gaaaatacga agtttctatt cccagctttg  17580
tctggtggcc ggcatggtcc cagcctcctc gctggcgccg gctgggcaac attccgaggg  17640
gaccgtcccc tcggtaatgg cgaatgggac gcggccggtc gatcgacgat ccggctgcta  17700
```

```
acaaagcccg aaaggaagct gagttggctg ctgccaccgc tgagcaataa ctagcataac  17760
cccttggggc ctctaaacgg gtcttgaggg gttttttgct gaaaggagga actatatccg  17820
gatcgagatc aattctgtga gcgtatggca aacgaaggaa aaatagttat agtagccgca  17880
ctcgatggga catttcaacg taaaccgttt aataatattt tgaatcttat tccattatct  17940
gaaatggtgg taaaactaac tgctgtgtgt atgaaatgct ttaaggaggc ttccttttct  18000
aaacgattgg gtgaggaaac cgagatagaa ataataggag gtaatgatat gtatcaatcg  18060
gtgtgtagaa agtgttacat cgactcataa tattatattt tttatctaaa aaactaaaaa  18120
taaacattga ttaaatttta atataatact taaaaatgga tgttgtgtcg ttagataaac  18180
cgtttatgta ttttgaggaa attgataatg agttagatta cgaaccagaa agtgcaaatg  18240
aggtcgcaaa aaaactgccg tatcaaggac agttaaaact attactagga gaattatttt  18300
ttcttagtaa gttacagcga cacggtatat tagatggtgc caccgtagtg tatataggat  18360
ctgctcccgg tacacatata cgttatttga gagatcattt ctataattta ggagtgatcc  18420
cgaaaggaag ctgagttggc tgctgccacc gctgagcaat aactagcata accccttggg  18480
gcctctaaac gggtcttgag gggttttttg ctgaaaggag gaacgcgcct gatgcggtat  18540
tttctcctta cgcatctgtg cggtatttca caccgcatat atggtgcact ctcagtacaa  18600
tctgctctga tgccgcatag ttaagccagc cccgacaccc gccaacaccc gctgacgcgc  18660
cctgacgggc ttgtctgctc ccggcatccg cttacagaca agctgtgacc gtctccggga  18720
gctgcatgtg tcagaggttt tcaccgtcat caccgaaacg cgcgagacga aagggcctcg  18780
tgatacgcct atttttatag gttaatgtca tgataataat ggtttcttag acgtcaggtg  18840
gcacttttcg gggaaatgtg cgcggaaccc ctatttgttt atttttctaa atacattcaa  18900
atatgtatcc gctcatgaga caataaccct gataaatgct tcaataatat tgaaaaagga  18960
agagtatgag tattcaacat ttccgtgtcg cccttattcc cttttttgcg gcattttgcc  19020
ttcctgtttt tgctcaccca gaaacgctgg tgaaagtaaa agatgctgaa gatcagttgg  19080
gtgcacgagt gggttacatc gaactggatc tcaacagcgg taagatcctt gagagttttc  19140
gccccgaaga acgttttcca atgatgagca cttttaaagt tctgctatgt ggcgcggtat  19200
tatcccgtat tgacgccggg caagagcaac tcggtcgccg catacactat tctcagaatg  19260
acttggttga gtactcacca gtcacagaaa agcatcttac ggatggcatg acagtaagag  19320
aattatgcag tgctgccata accatgagtg ataacactgc ggccaactta cttctgacaa  19380
cgatcggagg accgaaggag ctaaccgctt ttttgcacaa catgggggat catgtaactc  19440
gccttgatcg ttgggaaccg gagctgaatg aagccatacc aaacgacgag cgtgacacca  19500
cgatgcctgt agcaatggca acaacgttgc gcaaactatt aactggcgaa ctacttactc  19560
tagcttcccg gcaacaatta atagactgga tggaggcgga taaagttgca ggaccacttc  19620
tgcgctcggc ccttccggct ggctggttta ttgctgataa atctggagcc ggtgagcgtg  19680
ggtctcgcgg tatcattgca gcactggggc cagatggtaa gccctcccgt atcgtagtta  19740
tctacacgac ggggagtcag gcaactatgg atgaacgaaa tagacagatc gctgagatag  19800
gtgcctcact gattaagcat tggtaactgt cagaccaagt ttactcatat atactttaga  19860
ttgatttaaa acttcatttt taatttaaaa ggatctaggt gaagatcctt tttgataatc  19920
tcatgaccaa aatcccttaa cgtgagtttt cgttccactg agcgtcagac cccgtagaaa  19980
agatcaaagg atcttcttga gatccttttt ttctgcgcgt aatctgctgc ttgcaaacaa  20040
aaaaaccacc gctaccagcg gtggtttgtt tgccggatca agagctacca actctttttc  20100
```

```
cgaaggtaac tggcttcagc agagcgcaga taccaaatac tgtccttcta gtgtagccgt  20160

agttaggcca ccacttcaag aactctgtag caccgcctac atacctcgct ctgctaatcc  20220

tgttaccagt ggctgctgcc agtggcgata agtcgtgtct taccgggttg gactcaagac  20280

gatagttacc ggataaggcg cagcggtcgg gctgaacggg gggttcgtgc acacagccca  20340

gcttggagcg aacgacctac accgaactga gatacctaca gcgtgagcat tgagaaagcg  20400

ccacgcttcc cgaagggaga aaggcggaca ggtatccggt aagcggcagg gtcggaacag  20460

gagagcgcac gagggagctt ccagggggaa acgcctggta tctttatagt cctgtcgggt  20520

ttcgccacct ctgacttgag cgtcgatttt tgtgatgctc gtcagggggg cggagcctat  20580

ggaaaaacgc cagcaacgcg gcctttttac ggttcctggc cttttgctgg ccttttgctc  20640

acatgttctt tcctgcgtta tcccctgatt ctgtggataa ccgtattacc gcctttgagt  20700

gagctgatac cgctcgccgc agccgaacga ccgagcgcag cgagtcagtg agcgaggaag  20760

cggaagagcg cccaatacgc aaaccgcctc tccccgcgcg ttggccgatt cattaatgca  20820

gctggcacga caggtttccc gactggaaag cgggcagtga gcgcaacgca attaatgtga  20880

gttagctcac tcattaggca ccccaggctt tacactttat gcttccggct cgtatgttgt  20940

gtggaattgt gagcggataa caatttcaca caggaaacag ctatgaccat gattacgcca  21000

agcttacgcg tcctggcatt atgcccagta catgacctta tgggactttc ctacttggca  21060

gtacatctac gtattagtca tcgctattac catggtgatg cggttttggc agtacatcaa  21120

tgggcgtgga tagcggtttg actcacgggg atttccaagt ctccacccca ttgacgtcaa  21180

tgggagtttg ttttggcacc aaaatcaacg ggactttcca aaatgtcgta acaactccgc  21240

cccattgacg caaatgggcg gtaggcgtgt acggtgggag gtctatataa gcagagctcg  21300

tttagtgaac cgtgg                                                   21315
```

<210> SEQ ID NO 7
<211> LENGTH: 21309
<212> TYPE: DNA
<213> ORGANISM: Artificial
<220> FEATURE:
<223> OTHER INFORMATION: artificial construct

<400> SEQUENCE: 7

```
accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcga gaacaaggaa atctcagata ttgaagtgca agaccctgag ggattcaaca    600

tgattctggg taccatccta gcccaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780
```

```
aggacctctc cttacgccga ttcatggtcg ctctaatcct ggacatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggcga aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagcagatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggctacag tgtcattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc ttcattgaca ggtggtgcaa cccaatgtgc tcgaaagtca   2580
ccctcggaac catcagggcc aggtgcacct gcggggaacg tccccgagtg tgtgagcaat   2640
gccgcactga tacaggagtg gacacccgaa tctggcacca caatctcccc gagatcccag   2700
aataatgaag aagggggaga ccattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
```

```
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctgg tgaagataat aatgaagtag ctacagctca acttacctgc caaccccatg   3360
ccagtcgacc caactagcgt acgatgacgt cctagtacaa cctaaatcca ttataaaaaa   3420
cttaggagca aagtgattgc ctcccaagtt ccacaatgac agagatctac gacttcgaca   3480
agtcggcatg ggacatcaaa gggtcgatcg ctccgataca acccaccacc tacagtgatg   3540
gcaggctggt gccccaggtc agagtcatag atcctggtct aggcgacagg aaggatgaat   3600
gctttatgta catgtttctg ctgggggttg ttgaggacag cgattcccta gggcctccaa   3660
tcgggcgagc atttgggtcc ctgcccttag gtgttggcag atccacagca aagcccgaaa   3720
aactcctcaa agaggccact gagcttgaca tagttgttag acgtacagca gggctcaatg   3780
aaaaactggt gttctacaac aacaccccac taactctcct cacaccttgg agaaaggtcc   3840
taacaacagg gagtgtcttc aacgcaaacc aagtgtgcaa tgcggttaat ctgataccgc   3900
tcgatacccc gcagaggttc cgtgttgttt atatgagcat cacccgtctt tcggataacg   3960
ggtattacac cgttcctgga agaatgctgg aattcagatc ggtcaatgca gtggccttca   4020
acctgctggt gacccttagg attgacaagg cgataggccc tgggaagatc atcgacaata   4080
cagagcaact tcctgaggca acatttatgg tccacatcgg gaacttcagg agaaagaaga   4140
gtgaagtcta ctctgccgat tattgcaaaa tgaaaatcga aaagatgggc ctggtttttg   4200
cacttggtgg gatagggggc accagtcttc acattagaag cacaggcaaa atgagcaaga   4260
ctctccatgc acaactcggg ttcaagaaga ccttatgtta cccgctgatg gatatcaatg   4320
aagaccttaa tcgattactc tggaggagca gatgcaagat agtaagaatc caggcagttt   4380
tgcagccatc agttcctcaa gaattccgca tttacgacga cgtgatcata aatgatgacc   4440
aaggactatt caaagttctg tagaccgtag tgcccagcaa tgcccgaaaa cgacccccct   4500
cacaatgaca gccagaaggc ccggacaaaa aagccccctc cgaaagactc cacggaccaa   4560
gcgagaggcc agccagcagc cgacggcaag cgcgaacacc aggcggcccc agcacagaac   4620
agccctgaca caaggccacc accagccacc ccaatctgca tcctcctcgt gggacccccg   4680
aggaccaacc cccaaggctg cccccgatcc aaaccaccaa ccgcatcccc accacccccg   4740
ggaaagaaac ccccagcaat tggaaggccc ctccccctct tcctcaacac aagaactcca   4800
caaccgaacc gcacaagcga ccgaggtgac ccaaccgcag gcatccgact ccctagacag   4860
atcctctctc cccggcaaac taaacaaaac ttagggccaa ggaacataca cacccaacag   4920
aacccagacc ccggcccacg gcgccgcgcc cccaaccccc gacaaccaga gggagccccc   4980
aaccaatccc gccggctccc ccggtgccca caggcaggga caccaacccc cgaacagacc   5040
cagcacccaa ccatcgacaa tccaagacgg gggggccccc ccaaaaaaag gcccccaggg   5100
gccgacagcc agcaccgcga ggaagcccac ccaccccaca cacgaccacg gcaaccaaac   5160
cagaacccag accaccctgg gccaccagct cccagactcg gccatcaccc cgcagaaagg   5220
aaaggccaca acccgcgcac cccagccccg atccggcggg gagccaccca acccgaacca   5280
gcacccaaga gcgatccccg aaggaccccc gaaccgcaaa ggacatcagt atcccacagc   5340
ctctccaagt cccccggtct cctcctcttc tcgaagggac caaaagatca atccaccaca   5400
cccgacgaca ctcaactccc cacccctaaa ggagacaccg ggaatcccag aatcaagact   5460
catccaatgt ccatcatggg tctcaaggtg aacgtctctg ccatattcat ggcagtactg   5520
```

```
ttaactctcc aaacacccac cggtcaaatc cattggggca atctctctaa gataggggtg   5580
gtaggaatag gaagtgcaag ctacaaagtt atgactcgtt ccagccatca atcattagtc   5640
ataaaattaa tgcccaatat aactctcctc aataactgca cgagggtaga gattgcagaa   5700
tacaggagac tactgagaac agttttggaa ccaattagag atgcacttaa tgcagtgacc   5760
cagaatataa gaccggttca gagtgtagct tcaagtagga gacacaagag atttgcggga   5820
gtagtcctgg caggtgcggc cctaggcgtt gccacagctg ctcagataac agccggcatt   5880
gcacttcacc agtccatgct gaactctcaa gccatcgaca atctgagagc gagcctggaa   5940
actactaatc aggcaattga ggcaatcaga caagcagggc aggagatgat attggctgtt   6000
cagggtgtcc aagactacat caataatgag ctgataccgt ctatgaacca actatcttgt   6060
gatttaatcg gccagaagct cgggctcaaa ttgctcagat actatacaga aatcctgtca   6120
ttatttggcc ccagcttacg ggaccccata tctgcggaga tatctatcca ggctttgagc   6180
tatgcgcttg gaggagacat caataaggtg ttagaaaagc tcggatacag tggaggtgat   6240
ttactgggca tcttagagag cagaggaata aaggcccgga taactcacgt cgacacagag   6300
tcctacttca ttgtcctcag tatagcctat ccgacgctgt ccgagattaa gggggtgatt   6360
gtccaccggc tagagggggt ctcgtacaac ataggctctc aagagtggta taccactgtg   6420
cccaagtatg ttgcaaccca agggtacctt atctcgaatt ttgatgagtc atcgtgtact   6480
ttcatgccag aggggactgt gtgcagccaa aatgccttgt acccgatgag tcctctgctc   6540
caagaatgcc tccgggggtc caccaagtcc tgtgctcgta cactcgtatc cgggtctttt   6600
gggaaccggt tcattttatc acaagggaac ctaatagcca attgtgcatc aatcctttgc   6660
aagtgttaca caacaggaac gatcattaat caagaccctg acaagatcct aacatacatt   6720
gctgccgatc actgcccggt agtcgaggtg aacggcgtga ccatccaagt cgggagcagg   6780
aggtatccag acgctgtgta cttgcacaga attgacctcg gtcctcccat atcattggag   6840
aggttggacg tagggacaaa tctggggaat gcaattgcta agttggagga tgccaaggaa   6900
ttgttggagt catcggacca gatattgagg agtatgaaag gtttatcgag cactagcata   6960
gtctacatcc tgattgcagt gtgtcttgga gggttgatag ggatccccgc tttaatatgt   7020
tgctgcaggg ggcgttgtaa caaaaaggga gaacaagttg gtatgtcaag accaggccta   7080
aagcctgatc ttacgggaac atcaaaatcc tatgtaaggt cgctctgatc ctctacaact   7140
cttgaaacac aaatgtccca caagtctcct cttcgtcatc aagcaaccac cgcacccagc   7200
atcaagccca cctgaaatta tctccggttt ccctctggcc gaacaatatc ggtagttaat   7260
taaaacttag ggtgcaagat catccacaat gtcaccacaa cgagaccgga taaatgcctt   7320
ctacaaagat aacccccatc ccaagggaag taggatagtc attaacagag aacatcttat   7380
gattgataga ccttatgttt tgctggctgt tctgtttgtc atgtttctga gcttgatcgg   7440
gttgctagcc attgcaggca ttagacttca tcgggcagcc atctacaccg cagagatcca   7500
taaaagcctc agcaccaatc tagatgtaac taactcaatc gagcatcagg tcaaggacgt   7560
gctgacacca ctcttcaaaa tcatcggtga tgaagtgggc ctgaggacac ctcagagatt   7620
cactgaccta gtgaaattca tctctgacaa gattaaattc cttaatccgg atagggagta   7680
cgacttcaga gatctcactt ggtgtatcaa cccgccagag agaatcaaat tggattatga   7740
tcaatactgt gcagatgtgg ctgctgaaga gctcatgaat gcattggtga actcaactct   7800
actggagacc agaacaacca atcagttcct agctgtctca aagggaaact gctcagggcc   7860
cactacaatc agaggtcaat tctcaaacat gtcgctgtcc ctgttagact tgtatttagg   7920
```

```
tcgaggttac aatgtgtcat ctatagtcac tatgacatcc cagggaatgt atgggggaac   7980
ttacctagtg gaaaagccta atctgagcag caaaaggtca gagttgtcac aactgagcat   8040
gtaccgagtg tttgaagtag gtgttatcag aaatccgggt ttgggggctc cggtgttcca   8100
tatgacaaac tatcttgagc aaccagtcag taatgatctc agcaactgta tggtggcttt   8160
gggggagctc aaactcgcag ccctttgtca cggggaagat tctatcacaa ttccctatca   8220
gggatcaggg aaaggtgtca gcttccagct cgtcaagcta ggtgtctgga aatccccaac   8280
cgacatgcaa tcctgggtcc ccttatcaac ggatgatcca gtgatagaca ggctttacct   8340
ctcatctcac agaggtgtta tcgctgacaa ccaagcaaaa tgggctgtcc cgacaacacg   8400
aacagatgac aagttgcgaa tggagacatg cttccaacag gcgtgtaagg gtaaaatcca   8460
agcactctgc gagaatcccg agtgggcacc attgaaggat aacaggattc cttcatacgg   8520
ggtcttgtct gttgatctga gtctgacagt tgagcttaaa atcaaaattg cttcgggatt   8580
cgggccattg atcacacacg gttcagggat ggacctatac aaatccaacc acaacaatgt   8640
gtattggctg actatcccgc caatgaagaa cctagcctta ggtgtaatca acacattgga   8700
gtggataccg agattcaagg ttagtcccta cctcttcact gtcccaatta aggaagcagg   8760
cggagactgc catgccccaa catacctacc tgcggaggtg gatggtgatg tcaaactcag   8820
ttccaatctg gtgattctac ctggtcaaga tctccaatat gttttggcaa cctacgatac   8880
ttccagggtt gaacatgctg tggtttatta cgtttacagc ccaagccgct cattttctta   8940
cttttatcct tttaggttgc ctataaaggg ggtccccatc gaattacaag tggaatgctt   9000
cacatgggac caaaaactct ggtgccgtca cttctgtgtg cttgcggact cagaatctgg   9060
tggacatatc actcactctg ggatggtggg catgggagtc agctgcacag tcacccggga   9120
agatggaacc aatcgcagat agggctgcta gtgaaccaat cacatgatgt cacccagaca   9180
tcaggcatac ccactagtcc tccatcattg ttataaaaaa cttaggaacc aggtccacac   9240
agctcgagtc gcgcgtgcca ccatggagac agacacactc ctgctatggg tactgctgct   9300
ctgggttcca ggttccactg gtgactatcc atatgatgtt ccagattatg ctgaagtgca   9360
gctcgtggag agcggaggcg gattggtgca accaggcaaa tctctcaaac tgagctgcga   9420
agccagcgga ttcaccttct caggatatgg gatgcactgg gttagacaag ctcctgggag   9480
aggtcttgag tcagtcgcct acatcacctc ctctagcatc aacatcaagt atgcagatgc   9540
cgtgaaaggg cgattcacag ttagccggga caatgccaag aatctcctct ttctgcagat   9600
gaacatactg aagagtgagg atacagcgat gtactattgt gccaggtttg actgggataa   9660
gaactattgg ggacagggca caatggtcac tgtcagctct ggtggcggtg ggtcaggcgg   9720
aggcggttct ggcggcggcg gctctgacat tcagatgact cagtcaccgt catctctgcc   9780
cgcaagtttg ggtgatcgcg tgacaatcaa ttgccaagct agtcaggaca taagcaatta   9840
cctgaactgg taccagcaga agcctggtaa ggcacccaaa ctgctgatct actacacgaa   9900
caaacttgct gatggggtac catcccgttt ctccggcagt ggaagtggga gggacagctc   9960
ctttaccatt agctccctgg aaagcgagga cattgggtcc tactactgtc agcagtatta  10020
caactatccc tggacctttg ggcctggaac taagctggag attaagggag gaggcgggtc  10080
cggcgcccag gtgaaactgc agcagtctgg ggcagaactt gtgaggtcag ggacctcagt  10140
caagttgtcc tgcacagctt ctggcttcaa cattaaagac tcctatatgc actggttgag  10200
gcaggggcct gaacagtgcc tcgagtggat tggatggatt gatcctgaga atggtgatac  10260
```

```
tgaatatgcc ccgaagttcc agggcaaggc cacttttact acagacacat cctccaacac  10320
agcctacctg cagctcagca gcctgacatc tgaggacact gccgtctatt attgtaatga  10380
ggggactccg actgggccgt actactttga ctactggggc caagggacca cggtcaccgt  10440
ctcctcaggt ggaggcggtt caggcggagg tggctctggc ggtggcggat cagaaaatgt  10500
gctcacccag tctccagcaa tcatgtctgc atctccaggg gagaaagtca ccataacctg  10560
cagtgccagc tcaagtgtaa gttacatgca ctggttccag cagaagccag gcacttctcc  10620
caaactctgg atttatagca catccaacct ggcttctgga gtccctgctc gcttcagtgg  10680
cagtggatct gggacctctt actctctcac aatcagccga atggaggctg aagatgctgc  10740
cacttattac tgccagcaaa ggagtagtta cccactcacg ttcggttgtg gcaccaagct  10800
cgagctgaaa cgggcggccg ccagaggctc tcaccaccat catcaccact aggcgcgcgt  10860
tctagtgtga aatagacatc agaattaaga aaaacgtagg gtccaagtgg ttccccgtta  10920
tggactcgct atctgtcaac cagatcttat accctgaagt tcacctagat agcccgatag  10980
ttaccaataa gatagtagcc atcctggagt atgctcgagt ccctcacgct tacagcctgg  11040
aggaccctac actgtgtcag aacatcaagc accgcctaaa aaacggattt tccaaccaaa  11100
tgattataaa caatgtggaa gttgggaatg tcatcaagtc caagcttagg agttatccgg  11160
cccactctca tattccatat ccaaattgta atcaggattt atttaacata gaagacaaag  11220
agtcaacgag gaagatccgt gaactcctca aaaaggggaa ttcgctgtac tccaaagtca  11280
gtgataaggt tttccaatgc ttaagggaca ctaactcacg gcttggccta ggctccgaat  11340
tgagggagga catcaaggag aaagttatta acttgggagt ttacatgcac agctcccagt  11400
ggtttgagcc ctttctgttt tggtttacag tcaagactga gatgaggtca gtgattaaat  11460
cacaaaccca tacttgccat aggaggagac acacacctgt attcttcact ggtagttcag  11520
ttgagttgct aatctctcgt gaccttgttg ctataatcag taaagagtct caacatgtat  11580
attacctgac atttgaactg gttttgatgt attgtgatgt catagagggg aggttaatga  11640
cagagaccgc tatgactatt gatgctaggt atacagagct tctaggaaga gtcagataca  11700
tgtggaaact gatagatggt ttcttccctg cactcgggaa tccaacttat caaattgtag  11760
ccatgctgga gcctctttca cttgcttacc tgcagctgag ggatataaca gtagaactca  11820
gaggtgcttt ccttaaccac tgctttactg aaatacatga tgttcttgac caaaacgggt  11880
tttctgatga aggtacttat catgagttaa ttgaagctct agattacatt ttcataactg  11940
atgacataca tctgacaggg gagattttct catttttcag aagtttcggc caccccagac  12000
ttgaagcagt aacggctgct gaaaatgtta ggaaatacat gaatcagcct aaagtcattg  12060
tgtatgagac tctgatgaaa ggtcatgcca tattttgtgg aatcataatc aacggctatc  12120
gtgacaggca cggaggcagt tggccaccgc tgaccctccc cctgcatgct gcagacacaa  12180
tccggaatgc tcaagcttca ggtgatgggt taacacatga gcagtgcgtt gataactgga  12240
aatcttttgc tggagtgaaa tttggctgct ttatgcctct tagcctggat agtgatctga  12300
caatgtacct aaaggacaag gcacttgctg ctctccaaag ggaatgggat tcagtttacc  12360
cgaaagagtt cctgcgttac gaccctccca agggaaccgg gtcacggagg cttgtagatg  12420
ttttccttaa tgattcgagc tttgacccat atgatgtgat aatgtatgtt gtaagtggag  12480
cttacctcca tgaccctgag ttcaacctgt cttacagcct gaaagaaaag gagatcaagg  12540
aaacaggtag actttttgct aaaatgactt acaaaatgag ggcatgccaa gtgattgctg  12600
aaaatctaat ctcaaacggg attggcaaat attttaagga caatgggatg gccaaggatg  12660
```

```
agcacgattt gactaaggca ctccacactc tagctgtctc aggagtcccc aaagatctca  12720
aagaaagtca cagggggggg ccagtcttaa aaacctactc ccgaagccca gtccacacaa  12780
gtaccaggaa cgtgagagca gcaaaagggt ttatagggtt ccctcaagta attcggcagg  12840
accaagacac tgatcatccg gagaatatgg aagcttacga gacagtcagt gcatttatca  12900
cgactgatct caagaagtac tgccttaatt ggagatatga gaccatcagc ttgtttgcac  12960
agaggctaaa tgagatttac ggattgccct catttttcca gtggctgcat aagaggcttg  13020
agacctctgt cctgtatgta agtgaccctc attgcccccc cgaccttgac gcccatatcc  13080
cgttatataa agtccccaat gatcaaatct tcattaagta ccctatggga ggtatagaag  13140
ggtattgtca gaagctgtgg accatcagca ccattcccta tctatacctg gctgcttatg  13200
agagcggagt aaggattgct tcgttagtgc aaggggacaa tcagaccata gccgtaacaa  13260
aaagggtacc cagcacatgg ccctacaacc ttaagaaacg ggaagctgct agagtaacta  13320
gagattactt tgtaattctt aggcaaaggc tacatgatat tggccatcac ctcaaggcaa  13380
atgagacaat tgtttcatca cattttttttg tctattcaaa aggaatatat tatgatgggc  13440
tacttgtgtc ccaatcactc aagagcatcg caagatgtgt attctggtca gagactatag  13500
ttgatgaaac aagggcagca tgcagtaata ttgctacaac aatggctaaa agcatcgaga  13560
gaggttatga ccgttacctt gcatattccc tgaacgtcct aaaagtgata cagcaaattc  13620
tgatctctct tggcttcaca atcaattcaa ccatgacccg ggatgtagtc atacccctcc  13680
tcacaaacaa cgacctctta ataaggatgg cactgttgcc cgctcctatt ggggggatga  13740
attatctgaa tatgagcagg ctgtttgtca gaaacatcgg tgatccagta acatcatcaa  13800
ttgctgatct caagagaatg attctcgcct cactaatgcc tgaagagacc ctccatcagg  13860
taatgacaca acaaccgggg gactcttcat tcctagactg ggctagcgac ccttactcag  13920
caaatcttgt atgtgtccag agcatcacta gactcctcaa gaacataact gcaaggtttg  13980
tcctgatcca tagtccaaac ccaatgttaa aaggattatt ccatgatgac agtaaagaag  14040
aggacgaggg actggcggca ttcctcatgg acaggcatat tatagtacct agggcagctc  14100
atgaaatcct ggatcatagt gtcacagggg caagagagtc tattgcaggc atgctggata  14160
ccacaaaagg cttgattcga gccagcatga ggaagggggg tttaacctct cgagtgataa  14220
ccagattgtc caattatgac tatgaacaat tcagagcagg gatggtgcta ttgacaggaa  14280
gaaagagaaa tgtcctcatt gacaaagagt catgttcagt gcagctggcg agagctctaa  14340
gaagccatat gtgggcgagg ctagctcgag gacggcctat ttacggcctt gaggtccctg  14400
atgtactaga atctatgcga ggccacctta ttcggcgtca tgagacatgt gtcatctgcg  14460
agtgtggatc agtcaactac ggatggtttt ttgtcccctc gggttgccaa ctggatgata  14520
ttgacaagga aacatcatcc ttgagagtcc catatattgg ttctaccact gatgagagaa  14580
cagacatgaa gcttgccttc gtaagagccc caagtcgatc cttgcgatct gctgttagaa  14640
tagcaacagt gtactcatgg gcttacggtg atgatgatag ctcttggaac gaagcctggt  14700
tgttggctag gcaaagggcc aatgtgagcc tggaggagct aagggtgatc actcccatct  14760
caacttcgac taatttagcg cataggttga gggatcgtag cactcaagtg aaatactcag  14820
gtacatccct tgtccgagtg gcgaggtata ccacaatctc caacgacaat ctctcatttg  14880
tcatatcaga taagaaggtt gatactaact ttatatacca acaaggaatg cttctagggt  14940
tgggtgtttt agaaacattg tttcgactcg agaaagatac cggatcatct aacacggtat  15000
```

```
tacatcttca cgtcgaaaca gattgttgcg tgatcccgat gatagatcat cccaggatac  15060
ccagctcccg caagctagag ctgagggcag agctatgtac caacccattg atatatgata  15120
atgcaccttt aattgacaga gatgcaacaa ggctatacac ccagagccat aggaggcacc  15180
ttgtggaatt tgttacatgg tccacacccc aactatatca cattttagct aagtccacag  15240
cactatctat gattgacctg gtaacaaaat ttgagaagga ccatatgaat gaaatttcag  15300
ctctcatagg ggatgacgat atcaatagtt tcataactga gtttctgctc atagagccaa  15360
gattattcac tatctacttg ggccagtgtg cggccatcaa ttgggcattt gatgtacatt  15420
atcatagacc atcagggaaa tatcagatgg gtgagctgtt gtcatcgttc ctttctagaa  15480
tgagcaaagg agtgtttaag gtgcttgtca atgctctaag ccacccaaag atctacaaga  15540
aattctggca ttgtggtatt atagagccta tccatggtcc ttcacttgat gctcaaaact  15600
tgcacacaac tgtgtgcaac atggtttaca catgctatat gacctacctc gacctgttgt  15660
tgaatgaaga gttagaagag ttcacatttc tcttgtgtga aagcgacgag gatgtagtac  15720
cggacagatt cgacaacatc caggcaaaac acttatgtgt tctggcagat ttgtactgtc  15780
aaccagggac ctgcccacca attcaaggtc taagaccggt agagaaatgt gcagttctaa  15840
ccgaccatat caaggcagag gctatgttat ctccagcagg atcttcgtgg aacataaatc  15900
caattattgt agaccattac tcatgctccc tgacttatct ccggcgagga tcgatcaaac  15960
agataagatt gagagttgat ccaggattca ttttcgacgc cctcgctgag gtaaatgtca  16020
gtcagccaaa gatcggcagc aacaacatct caaatatgag catcaaggct ttcagacccc  16080
cacacgatga tgttgcaaaa ttgctcaaag atatcaacac aagcaagcac aatcttccca  16140
tttcaggggg caatctcgcc aattatgaaa tccatgcttt ccgcagaatc gggttgaact  16200
catctgcttg ctacaaagct gttgagatat caacattaat taggagatgc cttgagccag  16260
gggaggacgg cttgttcttg ggtgagggat cgggttctat gttgatcact tataaggaga  16320
tacttaaact aagcaagtgc ttctataata gtggggtttc cgccaattct agatctggtc  16380
aaagggaatt agcaccctat ccctccgaag ttggccttgt cgaacacaga atgggagtag  16440
gtaatattgt caaagtgctc tttaacggga ggcccgaagt cacgtgggta ggcagtgtag  16500
attgcttcaa tttcatagtt agtaatatcc ctacctctag tgtggggttt atccattcag  16560
atatagagac cttgcctgac aaagatacta tagagaagct agaggaattg gcagccatct  16620
tatcgatggc tctgctcctg ggcaaaatag gatcaatact ggtgattaag cttatgcctt  16680
tcagcgggga ttttgttcag ggatttataa gttatgtagg gtctcattat agagaagtga  16740
accttgtata ccctagatac agcaacttca tctctactga atcttatttg gttatgacag  16800
atctcaaggc taaccggcta atgaatcctg aaaagattaa gcagcagata attgaatcat  16860
ctgtgaggac ttcacctgga cttataggtc acatcctatc cattaagcaa ctaagctgca  16920
tacaagcaat tgtgggagac gcagttagta gaggtgatat caatcctact ctgaaaaaac  16980
ttacacctat agagcaggtg ctgatcaatt gcgggttggc aattaacgga cctaagctgt  17040
gcaaagaatt gatccaccat gatgttgcct cagggcaaga tggattgctt aattctatac  17100
tcatcctcta cagggagttg gcaagattca aagacaacca aagaagtcaa caagggatgt  17160
tccacgctta ccccgtattg gtaagtagca ggcaacgaga acttatatct aggatcaccc  17220
gcaaattctg gggggcacatt cttctttact ccgggaacaa aaagttgata aataagttta  17280
tccagaatct caagtccggc tatctgatac tagacttaca ccagaatatc ttcgttaaga  17340
atctatccaa gtcagagaaa cagattatta tgacgggggg tttgaaacgt gagtgggttt  17400
```

```
ttaaggtaac agtcaaggag accaaagaat ggtataagtt agtcggatac agtgccctga  17460
ttaaggacta attggttgaa ctccggaacc ctaatcctgc cctaggtggt taggcattat  17520
ttgcaatata ttaaagaaaa ctttgaaaat acgaagtttc tattcccagc tttgtctggt  17580
ggccggcatg gtcccagcct cctcgctggc gccggctggg caacattccg aggggaccgt  17640
cccctcggta atggcgaatg ggacgcggcc ggtcgatcga cgatccggct gctaacaaag  17700
cccgaaagga agctgagttg gctgctgcca ccgctgagca ataactagca taaccccttg  17760
gggcctctaa acgggtcttg aggggttttt tgctgaaagg aggaactata tccggatcga  17820
gatcaattct gtgagcgtat ggcaaacgaa ggaaaaatag ttatagtagc cgcactcgat  17880
gggacatttc aacgtaaacc gtttaataat attttgaatc ttattccatt atctgaaatg  17940
gtggtaaaac taactgctgt gtgtatgaaa tgctttaagg aggcttcctt ttctaaacga  18000
ttgggtgagg aaaccgagat agaaataata ggaggtaatg atatgtatca atcggtgtgt  18060
agaaagtgtt acatcgactc ataatattat atttttatc taaaaaacta aaaataaaca  18120
ttgattaaat tttaatataa tacttaaaaa tggatgttgt gtcgttagat aaaccgttta  18180
tgtattttga ggaaattgat aatgagttag attacgaacc agaaagtgca aatgaggtcg  18240
caaaaaaact gccgtatcaa ggacagttaa aactattact aggagaatta tttttttctta  18300
gtaagttaca gcgacacggt atattagatg gtgccaccgt agtgtatata ggatctgctc  18360
ccggtacaca tatacgttat ttgagagatc atttctataa tttaggagtg atcccgaaag  18420
gaagctgagt tggctgctgc caccgctgag caataactag cataacccct tggggcctct  18480
aaacgggtct tgaggggttt tttgctgaaa ggaggaacgc gcctgatgcg gtattttctc  18540
cttacgcatc tgtgcggtat ttcacaccgc atatatggtg cactctcagt acaatctgct  18600
ctgatgccgc atagttaagc cagccccgac acccgccaac acccgctgac gcgccctgac  18660
gggcttgtct gctcccggca tccgcttaca gacaagctgt gaccgtctcc gggagctgca  18720
tgtgtcagag gttttcaccg tcatcaccga aacgcgcgag acgaaagggc ctcgtgatac  18780
gcctattttt ataggttaat gtcatgataa taatggtttc ttagacgtca ggtggcactt  18840
ttcggggaaa tgtgcgcgga acccctattt gtttattttt ctaaatacat tcaaatatgt  18900
atccgctcat gagacaataa ccctgataaa tgcttcaata atattgaaaa aggaagagta  18960
tgagtattca acatttccgt gtcgccctta ttcccttttt tgcggcattt tgccttcctg  19020
tttttgctca cccagaaacg ctggtgaaag taaaagatgc tgaagatcag ttgggtgcac  19080
gagtgggtta catcgaactg gatctcaaca gcggtaagat ccttgagagt tttcgccccg  19140
aagaacgttt tccaatgatg agcactttta aagttctgct atgtggcgcg gtattatccc  19200
gtattgacgc cgggcaagag caactcggtc gccgcataca ctattctcag aatgacttgg  19260
ttgagtactc accagtcaca gaaaagcatc ttacggatgg catgacagta agagaattat  19320
gcagtgctgc cataaccatg agtgataaca ctgcggccaa cttacttctg acaacgatcg  19380
gaggaccgaa ggagctaacc gctttttttgc acaacatggg ggatcatgta actcgccttg  19440
atcgttggga accggagctg aatgaagcca taccaaacga cgagcgtgac accacgatgc  19500
ctgtagcaat ggcaacaacg ttgcgcaaac tattaactgg cgaactactt actctagctt  19560
cccggcaaca attaatagac tggatggagg cggataaagt tgcaggacca cttctgcgct  19620
cggcccttcc ggctggctgg tttattgctg ataaatctgg agccggtgag cgtgggtctc  19680
gcggtatcat tgcagcactg gggccagatg gtaagccctc ccgtatcgta gttatctaca  19740
```

```
cgacggggag tcaggcaact atggatgaac gaaatagaca gatcgctgag ataggtgcct  19800
cactgattaa gcattggtaa ctgtcagacc aagtttactc atatatactt tagattgatt  19860
taaaacttca tttttaattt aaaaggatct aggtgaagat cctttttgat aatctcatga  19920
ccaaaatccc ttaacgtgag ttttcgttcc actgagcgtc agaccccgta gaaaagatca  19980
aaggatcttc ttgagatcct ttttttctgc gcgtaatctg ctgcttgcaa acaaaaaaac  20040
caccgctacc agcggtggtt tgtttgccgg atcaagagct accaactctt tttccgaagg  20100
taactggctt cagcagagcg cagataccaa atactgtcct tctagtgtag ccgtagttag  20160
gccaccactt caagaactct gtagcaccgc ctacatacct cgctctgcta atcctgttac  20220
cagtggctgc tgccagtggc gataagtcgt gtcttaccgg gttggactca agacgatagt  20280
taccggataa ggcgcagcgg tcgggctgaa cggggggttc gtgcacacag cccagcttgg  20340
agcgaacgac ctacaccgaa ctgagatacc tacagcgtga gcattgagaa agcgccacgc  20400
ttcccgaagg gagaaaggcg gacaggtatc cggtaagcgg cagggtcgga acaggagagc  20460
gcacgaggga gcttccaggg ggaaacgcct ggtatcttta tagtcctgtc gggtttcgcc  20520
acctctgact tgagcgtcga tttttgtgat gctcgtcagg ggggcggagc ctatggaaaa  20580
acgccagcaa cgcggccttt ttacggttcc tggccttttg ctggcctttt gctcacatgt  20640
tctttcctgc gttatcccct gattctgtgg ataaccgtat taccgccttt gagtgagctg  20700
ataccgctcg ccgcagccga acgaccgagc gcagcgagtc agtgagcgag gaagcggaag  20760
agcgcccaat acgcaaaccg cctctccccg cgcgttggcc gattcattaa tgcagctggc  20820
acgacaggtt tcccgactgg aaagcgggca gtgagcgcaa cgcaattaat gtgagttagc  20880
tcactcatta ggcaccccag gctttacact ttatgcttcc ggctcgtatg ttgtgtggaa  20940
ttgtgagcgg ataacaattt cacacaggaa acagctatga ccatgattac gccaagctta  21000
cgcgtcctgg cattatgccc agtacatgac cttatgggac tttcctactt ggcagtacat  21060
ctacgtatta gtcatcgcta ttaccatggt gatgcggttt tggcagtaca tcaatgggcg  21120
tggatagcgg tttgactcac ggggatttcc aagtctccac cccattgacg tcaatgggag  21180
tttgttttgg caccaaaatc aacgggactt tccaaaatgt cgtaacaact ccgccccatt  21240
gacgcaaatg ggcggtaggc gtgtacggtg ggaggtctat ataagcagag ctcgtttagt  21300
gaaccgtgg                                                         21309
```

<210> SEQ ID NO 8
<211> LENGTH: 21333
<212> TYPE: DNA
<213> ORGANISM: Artificial
<220> FEATURE:
<223> OTHER INFORMATION: artificial construct

<400> SEQUENCE: 8

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
```

```
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggacatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagcagatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggctacag tgtcattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc ttcattgaca ggtggtgcaa cccaatgtgc tcgaaagtca   2580
ccctcggaac catcagggcc aggtgcacct gcggggaacg tccccgagtg tgtgagcaat   2640
gccgcactga tacaggagtg gacacccgaa tctggcacca caatctcccc gagatcccag   2700
aataatgaag aagggggaga ccattatgat gatgagctgt tctctgatgt ccaagatatt   2760
aaaacagcct tggccaaaat acacgaggat aatcagaaga taatctccaa gctagaatca   2820
```

```
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctgg tgaagataat aatgaagtag ctacagctca acttacctgc caaccccatg   3360
ccagtcgacc caactagcgt acgatgacgt cctagtacaa cctaaatcca ttataaaaaa   3420
cttaggagca aagtgattgc ctcccaagtt ccacaatgac agagatctac gacttcgaca   3480
agtcggcatg ggacatcaaa gggtcgatcg ctccgataca acccaccacc tacagtgatg   3540
gcaggctggt gccccaggtc agagtcatag atcctggtct aggcgacagg aaggatgaat   3600
gctttatgta catgtttctg ctgggggttg ttgaggacag cgattcccta gggcctccaa   3660
tcgggcgagc atttgggtcc ctgcccttag gtgttggcag atccacagca aagcccgaaa   3720
aactcctcaa agaggccact gagcttgaca tagttgttag acgtacagca gggctcaatg   3780
aaaaactggt gttctacaac aacaccccac taactctcct cacaccttgg agaaaggtcc   3840
taacaacagg gagtgtcttc aacgcaaacc aagtgtgcaa tgcggttaat ctgataccgc   3900
tcgatacccc gcagaggttc cgtgttgttt atatgagcat cacccgtctt tcggataacg   3960
ggtattacac cgttcctgga agaatgctgg aattcagatc ggtcaatgca gtggccttca   4020
acctgctggt gacccttagg attgacaagg cgataggccc tgggaagatc atcgacaata   4080
cagagcaact tcctgaggca acatttatgg tccacatcgg gaacttcagg agaaagaaga   4140
gtgaagtcta ctctgccgat tattgcaaaa tgaaaatcga aaagatgggc ctggtttttg   4200
cacttggtgg gatagggggc accagtcttc acattagaag cacaggcaaa atgagcaaga   4260
ctctccatgc acaactcggg ttcaagaaga ccttatgtta cccgctgatg gatatcaatg   4320
aagaccttaa tcgattactc tggaggagca gatgcaagat agtaagaatc caggcagttt   4380
tgcagccatc agttcctcaa gaattccgca tttacgacga cgtgatcata aatgatgacc   4440
aaggactatt caaagttctg tagaccgtag tgcccagcaa tgcccgaaaa cgaccccccct  4500
cacaatgaca gccagaaggc ccggacaaaa aagcccccctc cgaaagactc cacggaccaa  4560
gcgagaggcc agccagcagc cgacggcaag cgcgaacacc aggcggcccc agcacagaac   4620
agccctgaca caaggccacc accagccacc ccaatctgca tcctcctcgt gggacccccg   4680
aggaccaacc cccaaggctg cccccgatcc aaaccaccaa ccgcatcccc accaccccccg  4740
ggaaagaaac ccccagcaat tggaaggccc ctccccctct tcctcaacac aagaactcca   4800
caaccgaacc gcacaagcga ccgaggtgac ccaaccgcag gcatccgact ccctagacag   4860
atcctctctc cccggcaaac taaacaaaac ttagggccaa ggaacataca cacccaacag   4920
aacccagacc ccggcccacg gcgccgcgcc cccaaccccc gacaaccaga gggagccccc   4980
aaccaatccc gccggctccc ccggtgccca caggcaggga caccaacccc cgaacagacc   5040
cagcacccaa ccatcgacaa tccaagacgg gggggccccc ccaaaaaaag gcccccaggg   5100
gccgacagcc agcaccgcga ggaagcccac ccaccccaca cacgaccacg gcaaccaaac   5160
cagaacccag accaccctgg gccaccagct cccagactcg gccatcaccc cgcagaaagg   5220
```

```
aaaggccaca acccgcgcac cccagccccg atccggcggg gagccaccca acccgaacca   5280
gcacccaaga gcgatccccg aaggaccccc gaaccgcaaa ggacatcagt atcccacagc   5340
ctctccaagt cccccggtct cctcctcttc tcgaagggac caaaagatca atccaccaca   5400
cccgacgaca ctcaactccc cacccctaaa ggagacaccg ggaatcccag aatcaagact   5460
catccaatgt ccatcatggg tctcaaggtg aacgtctctg ccatattcat ggcagtactg   5520
ttaactctcc aaacacccac cggtcaaatc cattggggca atctctctaa gatagggtg    5580
gtaggaatag gaagtgcaag ctacaaagtt atgactcgtt ccagccatca atcattagtc   5640
ataaaattaa tgcccaatat aactctcctc aataactgca cgagggtaga gattgcagaa   5700
tacaggagac tactgagaac agttttggaa ccaattagag atgcacttaa tgcagtgacc   5760
cagaatataa gaccggttca gagtgtagct tcaagtagga gacacaagag atttgcggga   5820
gtagtcctgg caggtgcggc cctaggcgtt gccacagctg ctcagataac agccggcatt   5880
gcacttcacc agtccatgct gaactctcaa gccatcgaca atctgagagc gagcctggaa   5940
actactaatc aggcaattga ggcaatcaga caagcagggc aggagatgat attggctgtt   6000
cagggtgtcc aagactacat caataatgag ctgataccgt ctatgaacca actatcttgt   6060
gatttaatcg gccagaagct cgggctcaaa ttgctcagat actatacaga aatcctgtca   6120
ttatttggcc ccagcttacg ggaccccata tctgcggaga tatctatcca ggctttgagc   6180
tatgcgcttg gaggagacat caataaggtg ttagaaaagc tcggatacag tggaggtgat   6240
ttactgggca tcttagagag cagaggaata aaggcccgga taactcacgt cgacacagag   6300
tcctacttca ttgtcctcag tatagcctat ccgacgctgt ccgagattaa gggggtgatt   6360
gtccaccggc tagagggggt ctcgtacaac ataggctctc aagagtggta taccactgtg   6420
cccaagtatg ttgcaaccca agggtacctt atctcgaatt ttgatgagtc atcgtgtact   6480
ttcatgccag aggggactgt gtgcagccaa aatgccttgt acccgatgag tcctctgctc   6540
caagaatgcc tccgggggtc caccaagtcc tgtgctcgta cactcgtatc cgggtctttt   6600
gggaaccggt tcattttatc acaagggaac ctaatagcca attgtgcatc aatcctttgc   6660
aagtgttaca caacaggaac gatcattaat caagaccctg acaagatcct aacatacatt   6720
gctgccgatc actgcccggt agtcgaggtg aacggcgtga ccatccaagt cgggagcagg   6780
aggtatccag acgctgtgta cttgcacaga attgacctcg gtcctcccat atcattggag   6840
aggttggacg tagggacaaa tctggggaat gcaattgcta agttggagga tgccaaggaa   6900
ttgttggagt catcggacca gatattgagg agtatgaaag gtttatcgag cactagcata   6960
gtctacatcc tgattgcagt gtgtcttgga gggttgatag ggatccccgc tttaatatgt   7020
tgctgcaggg ggcgttgtaa caaaaaggga gaacaagttg gtatgtcaag accaggccta   7080
aagcctgatc ttacgggaac atcaaaatcc tatgtaaggt cgctctgatc ctctacaact   7140
cttgaaacac aaatgtccca caagtctcct cttcgtcatc aagcaaccac cgcacccagc   7200
atcaagccca cctgaaatta tctccggttt ccctctggcc gaacaatatc ggtagttaat   7260
taaaacttag ggtgcaagat catccacaat gtcaccacaa cgagaccgga taaatgcctt   7320
ctacaaagat aacccccatc ccaagggaag taggatagtc attaacagag aacatcttat   7380
gattgataga ccttatgttt tgctggctgt tctgtttgtc atgtttctga gcttgatcgg   7440
gttgctagcc attgcaggca ttagacttca tcgggcagcc atctacaccg cagagatcca   7500
taaaagcctc agcaccaatc tagatgtaac taactcaatc gagcatcagg tcaaggacgt   7560
```

```
gctgacacca ctcttcaaaa tcatcggtga tgaagtgggc ctgaggacac ctcagagatt   7620
cactgaccta gtgaaattca tctctgacaa gattaaattc cttaatccgg atagggagta   7680
cgacttcaga gatctcactt ggtgtatcaa cccgccagag agaatcaaat tggattatga   7740
tcaatactgt gcagatgtgg ctgctgaaga gctcatgaat gcattggtga actcaactct   7800
actggagacc agaacaacca atcagttcct agctgtctca aagggaaact gctcagggcc   7860
cactacaatc agaggtcaat tctcaaacat gtcgctgtcc ctgttagact tgtatttagg   7920
tcgaggttac aatgtgtcat ctatagtcac tatgacatcc cagggaatgt atgggggaac   7980
ttacctagtg gaaaagccta atctgagcag caaaaggtca gagttgtcac aactgagcat   8040
gtaccgagtg tttgaagtag gtgttatcag aaatccgggt ttgggggctc cggtgttcca   8100
tatgacaaac tatcttgagc aaccagtcag taatgatctc agcaactgta tggtggcttt   8160
gggggagctc aaactcgcag ccctttgtca cggggaagat tctatcacaa ttccctatca   8220
gggatcaggg aaaggtgtca gcttccagct cgtcaagcta ggtgtctgga aatccccaac   8280
cgacatgcaa tcctgggtcc ccttatcaac ggatgatcca gtgatagaca ggctttacct   8340
ctcatctcac agaggtgtta tcgctgacaa ccaagcaaaa tgggctgtcc cgacaacacg   8400
aacagatgac aagttgcgaa tggagacatg cttccaacag gcgtgtaagg gtaaaatcca   8460
agcactctgc gagaatcccg agtgggcacc attgaaggat aacaggattc cttcatacgg   8520
ggtcttgtct gttgatctga gtctgacagt tgagcttaaa atcaaaattg cttcgggatt   8580
cgggccattg atcacacacg gttcagggat ggacctatac aaatccaacc acaacaatgt   8640
gtattggctg actatcccgc caatgaagaa cctagcctta ggtgtaatca acacattgga   8700
gtggataccg agattcaagg ttagtcccta cctcttcact gtcccaatta aggaagcagg   8760
cggagactgc catgccccaa catacctacc tgcggaggtg gatggtgatg tcaaactcag   8820
ttccaatctg gtgattctac ctggtcaaga tctccaatat gttttggcaa cctacgatac   8880
ttccagggtt gaacatgctg tggtttatta cgtttacagc ccaagccgct cattttctta   8940
cttttatcct tttaggttgc ctataaaggg ggtccccatc gaattacaag tggaatgctt   9000
cacatgggac caaaaactct ggtgccgtca cttctgtgtg cttgcggact cagaatctgg   9060
tggacatatc actcactctg ggatggtggg catgggagtc agctgcacag tcacccggga   9120
agatggaacc aatcgcagat agggctgcta gtgaaccaat cacatgatgt cacccagaca   9180
tcaggcatac ccactagtcc tccatcattg ttataaaaaa cttaggaacc aggtccacac   9240
agctcgagtc gcgcgtgcca ccatggagac agacacactc ctgctatggg tactgctgct   9300
ctgggttcca ggttccactg gtgactatcc atatgatgtt ccagattatg ctcaggtgca   9360
gcttcagcaa tccggggcag aactggctag acctggggct agcgtcaaga tgtcctgcaa   9420
agcctccgga tatactttca cacgctatac catgcattgg gtcaaacaac gaccaggtca   9480
aggcctcgaa tggatcggct atatcaatcc gagtagggga tacaccaact acaaccagaa   9540
gttcaaggat aaggctacac tgacaaccga caagtcatct tcaacggcct atatgcagct   9600
ttccagcctg acaagcgagg attctgccgt ttactactgt gcgcggtact atgacgatca   9660
ctactgcttg gactattggg gccaaggtac cactttgacc gtatctagcg gaggcggcgg   9720
gagtggcgga ggtgggagtg gcggtggtgg gagccagatt gtgctcactc agtcccctgc   9780
aatcatgtca gcaagtcctg gggagaaagt gactatgact tgttccgcta gcagcagtgt   9840
gagctacatg aactggtacc agcagaagtc tggaacctca cccaaacggt ggatctacga   9900
cacatcaaaa ctggccagtg ggttccagc gcattttcgt gggtctggca gcggaacaag   9960
```

```
ctattccctg acgatttccg ggatggaagc cgaggatgca gccacctatt actgccagca  10020
gtggagctca aatcccttta ccttcggatc tggcactaag ctggagataa atggtggcgg  10080
aggctctggc gcccaggttc agctggtcca gtcaggggct gagctggtga agcctggggc  10140
ctcagtgaag atgtcctgca aggcttctgg ctacacattt accagttaca atatgcactg  10200
ggtaaagcag acacctggac agggcctgga atggattgga gctatttatc caggaaatgg  10260
tgatacttcc tacaatcaga agttcaaagg caaggccaca ttgactgcag acaaatcctc  10320
cagcacagcc tacatgcagc tcagcagcct gacatctgag gactctgcgg tctattactg  10380
tgcaagagcg caattacgac ctaactactg gtacttcgat gtctggggcg cagggaccac  10440
ggtcaccgtg agcaagatct ctggtggcgg tggctcgggc ggtggtgggt cgggtggcgg  10500
aggctcgggt ggctcgagcg acatcgtgct gtcgcagtct ccagcaatcc tgtctgcatc  10560
tccaggggag aaggtcacaa tgacttgcag ggccagctca agtgtaagtt acatgcactg  10620
gtaccagcag aagccaggat cctcccccaa accctggatt tatgccacat ccaacctggc  10680
ttctggagtc cctgctcgct tcagtggcag tgggtctggg acctcttact ctctcacaat  10740
cagcagagtg gaggctgaag atgctgccac ttattactgc cagcagtgga ttagtaaccc  10800
acccacgttc ggtgctggga ccaagctgga gctgaaggcg gccgccagag gctctcacca  10860
ccatcatcac cactaggcgc gcgttctagt gtgaaataga catcagaatt aagaaaaacg  10920
tagggtccaa gtggttcccc gttatggact cgctatctgt caaccagatc ttataccctg  10980
aagttcacct agatagcccg atagttacca ataagatagt agccatcctg gagtatgctc  11040
gagtccctca cgcttacagc ctggaggacc ctacactgtg tcagaacatc aagcaccgcc  11100
taaaaaacgg attttccaac caaatgatta taaacaatgt ggaagttggg aatgtcatca  11160
agtccaagct taggagttat ccggcccact ctcatattcc atatccaaat tgtaatcagg  11220
atttatttaa catagaagac aaagagtcaa cgaggaagat ccgtgaactc ctcaaaaagg  11280
ggaattcgct gtactccaaa gtcagtgata aggttttcca atgcttaagg gacactaact  11340
cacggcttgg cctaggctcc gaattgaggg aggacatcaa ggagaaagtt attaacttgg  11400
gagtttacat gcacagctcc cagtggtttg agccctttct gttttggttt acagtcaaga  11460
ctgagatgag gtcagtgatt aaatcacaaa cccatacttg ccataggagg agacacacac  11520
ctgtattctt cactggtagt tcagttgagt tgctaatctc tcgtgacctt gttgctataa  11580
tcagtaaaga gtctcaacat gtatattacc tgacatttga actggttttg atgtattgtg  11640
atgtcataga ggggaggtta atgacagaga ccgctatgac tattgatgct aggtatacag  11700
agcttctagg aagagtcaga tacatgtgga aactgataga tggtttcttc cctgcactcg  11760
ggaatccaac ttatcaaatt gtagccatgc tggagcctct ttcacttgct tacctgcagc  11820
tgagggatat aacagtagaa ctcagaggtg ctttccttaa ccactgcttt actgaaatac  11880
atgatgttct tgaccaaaac gggttttctg atgaaggtac ttatcatgag ttaattgaag  11940
ctctagatta cattttcata actgatgaca tacatctgac aggggagatt ttctcatttt  12000
tcagaagttt cggccacccc agacttgaag cagtaacggc tgctgaaaat gttaggaaat  12060
acatgaatca gcctaaagtc attgtgtatg agactctgat gaaaggtcat gccatatttt  12120
gtggaatcat aatcaacggc tatcgtgaca ggcacggagg cagttggcca ccgctgaccc  12180
tcccccctgca tgctgcagac acaatccgga atgctcaagc ttcaggtgat gggttaacac  12240
atgagcagtg cgttgataac tggaaatctt ttgctggagt gaaatttggc tgctttatgc  12300
```

```
ctcttagcct ggatagtgat ctgacaatgt acctaaagga caaggcactt gctgctctcc  12360
aaagggaatg ggattcagtt tacccgaaag agttcctgcg ttacgaccct cccaagggaa  12420
ccgggtcacg gaggcttgta gatgttttcc ttaatgattc gagctttgac ccatatgatg  12480
tgataatgta tgttgtaagt ggagcttacc tccatgaccc tgagttcaac ctgtcttaca  12540
gcctgaaaga aaaggagatc aaggaaacag gtagactttt tgctaaaatg acttacaaaa  12600
tgagggcatg ccaagtgatt gctgaaaatc taatctcaaa cgggattggc aaatatttta  12660
aggacaatgg gatggccaag gatgagcacg atttgactaa ggcactccac actctagctg  12720
tctcaggagt ccccaaagat ctcaaagaaa gtcacagggg ggggccagtc ttaaaaacct  12780
actcccgaag cccagtccac acaagtacca ggaacgtgag agcagcaaaa gggtttatag  12840
ggttccctca agtaattcgg caggaccaag acactgatca tccggagaat atggaagctt  12900
acgagacagt cagtgcattt atcacgactg atctcaagaa gtactgcctt aattggagat  12960
atgagaccat cagcttgttt gcacagaggc taaatgagat ttacggattg ccctcatttt  13020
tccagtggct gcataagagg cttgagacct ctgtcctgta tgtaagtgac cctcattgcc  13080
cccccgacct tgacgcccat atcccgttat ataaagtccc caatgatcaa atcttcatta  13140
agtaccctat gggaggtata gaagggtatt gtcagaagct gtggaccatc agcaccattc  13200
cctatctata cctggctgct tatgagagcg gagtaaggat tgcttcgtta gtgcaagggg  13260
acaatcagac catagccgta acaaaaaggg tacccagcac atggccctac aaccttaaga  13320
aacgggaagc tgctagagta actagagatt actttgtaat tcttaggcaa aggctacatg  13380
atattggcca tcacctcaag gcaaatgaga caattgtttc atcacatttt tttgtctatt  13440
caaaaggaat atattatgat gggctacttg tgtcccaatc actcaagagc atcgcaagat  13500
gtgtattctg gtcagagact atagttgatg aaacaagggc agcatgcagt aatattgcta  13560
caacaatggc taaaagcatc gagagaggtt atgaccgtta ccttgcatat tccctgaacg  13620
tcctaaaagt gatacagcaa attctgatct ctcttggctt cacaatcaat tcaaccatga  13680
cccgggatgt agtcataccc ctcctcacaa acaacgacct cttaataagg atggcactgt  13740
tgcccgctcc tattgggggg atgaattatc tgaatatgag caggctgttt gtcagaaaca  13800
tcggtgatcc agtaacatca tcaattgctg atctcaagag aatgattctc gcctcactaa  13860
tgcctgaaga gaccctccat caggtaatga cacaacaacc gggggactct tcattcctag  13920
actgggctag cgacccttac tcagcaaatc ttgtatgtgt ccagagcatc actagactcc  13980
tcaagaacat aactgcaagg tttgtcctga tccatagtcc aaacccaatg ttaaaaggat  14040
tattccatga tgacagtaaa gaagaggacg agggactggc ggcattcctc atggacaggc  14100
atattatagt acctagggca gctcatgaaa tcctggatca tagtgtcaca ggggcaagag  14160
agtctattgc aggcatgctg gataccacaa aaggcttgat tcgagccagc atgaggaagg  14220
ggggtttaac ctctcgagtg ataaccagat tgtccaatta tgactatgaa caattcagag  14280
cagggatggt gctattgaca ggaagaaaga gaaatgtcct cattgacaaa gagtcatgtt  14340
cagtgcagct ggcgagagct ctaagaagcc atatgtgggc gaggctagct cgaggacggc  14400
ctatttacgg ccttgaggtc cctgatgtac tagaatctat gcgaggccac cttattcggc  14460
gtcatgagac atgtgtcatc tgcgagtgtg gatcagtcaa ctacggatgg ttttttgtcc  14520
cctcgggttg ccaactggat gatattgaca aggaaacatc atccttgaga gtcccatata  14580
ttggttctac cactgatgag agaacagaca tgaagcttgc cttcgtaaga gccccaagtc  14640
gatccttgcg atctgctgtt agaatagcaa cagtgtactc atgggcttac ggtgatgatg  14700
```

```
atagctcttg gaacgaagcc tggttgttgg ctaggcaaag ggccaatgtg agcctggagg  14760
agctaagggt gatcactccc atctcaactt cgactaattt agcgcatagg ttgagggatc  14820
gtagcactca agtgaaatac tcaggtacat cccttgtccg agtggcgagg tataccacaa  14880
tctccaacga caatctctca tttgtcatat cagataagaa ggttgatact aactttatat  14940
accaacaagg aatgcttcta gggttgggtg ttttagaaac attgtttcga ctcgagaaag  15000
ataccggatc atctaacacg gtattacatc ttcacgtcga aacagattgt tgcgtgatcc  15060
cgatgataga tcatcccagg atacccagct cccgcaagct agagctgagg gcagagctat  15120
gtaccaaccc attgatatat gataatgcac ctttaattga cagagatgca acaaggctat  15180
acacccagag ccataggagg caccttgtgg aatttgttac atggtccaca ccccaactat  15240
atcacatttt agctaagtcc acagcactat ctatgattga cctggtaaca aaatttgaga  15300
aggaccatat gaatgaaatt tcagctctca taggggatga cgatatcaat agtttcataa  15360
ctgagtttct gctcatagag ccaagattat tcactatcta cttgggccag tgtgcggcca  15420
tcaattgggc atttgatgta cattatcata gaccatcagg gaaatatcag atgggtgagc  15480
tgttgtcatc gttcctttct agaatgagca aaggagtgtt taaggtgctt gtcaatgctc  15540
taagccaccc aaagatctac aagaaattct ggcattgtgg tattatagag cctatccatg  15600
gtccttcact tgatgctcaa aacttgcaca caactgtgtg caacatggtt tacacatgct  15660
atatgaccta cctcgacctg ttgttgaatg aagagttaga agagttcaca tttctcttgt  15720
gtgaaagcga cgaggatgta gtaccggaca gattcgacaa catccaggca aaacacttat  15780
gtgttctggc agatttgtac tgtcaaccag ggacctgccc accaattcaa ggtctaagac  15840
cggtagagaa atgtgcagtt ctaaccgacc atatcaaggc agaggctatg ttatctccag  15900
caggatcttc gtggaacata aatccaatta ttgtagacca ttactcatgc tccctgactt  15960
atctccggcg aggatcgatc aaacagataa gattgagagt tgatccagga ttcattttcg  16020
acgccctcgc tgaggtaaat gtcagtcagc caaagatcgg cagcaacaac atctcaaata  16080
tgagcatcaa ggctttcaga cccccacacg atgatgttgc aaaattgctc aaagatatca  16140
acacaagcaa gcacaatctt cccatttcag ggggcaatct cgccaattat gaaatccatg  16200
ctttccgcag aatcgggttg aactcatctg cttgctacaa agctgttgag atatcaacat  16260
taattaggag atgccttgag ccaggggagg acggcttgtt cttgggtgag ggatcgggtt  16320
ctatgttgat cacttataag gagatactta aactaagcaa gtgcttctat aatagtgggg  16380
tttccgccaa ttctagatct ggtcaaaggg aattagcacc ctatccctcc gaagttggcc  16440
ttgtcgaaca cagaatggga gtaggtaata ttgtcaaagt gctctttaac gggaggcccg  16500
aagtcacgtg ggtaggcagt gtagattgct tcaatttcat agttagtaat atccctacct  16560
ctagtgtggg gtttatccat tcagatatag agaccttgcc tgacaaagat actatagaga  16620
agctagagga attggcagcc atcttatcga tggctctgct cctgggcaaa ataggatcaa  16680
tactggtgat taagcttatg cctttcagcg gggattttgt tcagggattt ataagttatg  16740
tagggtctca ttatagagaa gtgaaccttg tataccctag atacagcaac ttcatctcta  16800
ctgaatctta tttggttatg acagatctca aggctaaccg gctaatgaat cctgaaaaga  16860
ttaagcagca gataattgaa tcatctgtga ggacttcacc tggacttata ggtcacatcc  16920
tatccattaa gcaactaagc tgcatacaag caattgtggg agacgcagtt agtagaggtg  16980
atatcaatcc tactctgaaa aaacttacac ctatagagca ggtgctgatc aattgcgggt  17040
```

-continued

```
tggcaattaa cggacctaag ctgtgcaaag aattgatcca ccatgatgtt gcctcagggc  17100
aagatggatt gcttaattct atactcatcc tctacaggga gttggcaaga ttcaaagaca  17160
accaaagaag tcaacaaggg atgttccacg cttaccccgt attggtaagt agcaggcaac  17220
gagaacttat atctaggatc acccgcaaat tctgggggca cattcttctt tactccggga  17280
acaaaaagtt gataaataag tttatccaga atctcaagtc cggctatctg atactagact  17340
tacaccagaa tatcttcgtt aagaatctat ccaagtcaga gaaacagatt attatgacgg  17400
ggggtttgaa acgtgagtgg gtttttaagg taacagtcaa ggagaccaaa gaatggtata  17460
agttagtcgg atacagtgcc ctgattaagg actaattggt tgaactccgg aaccctaatc  17520
ctgccctagg tggttaggca ttatttgcaa tatattaaag aaaactttga aaatacgaag  17580
tttctattcc cagctttgtc tggtggccgg catggtccca gcctcctcgc tggcgccggc  17640
tgggcaacat tccgagggga ccgtcccctc ggtaatggcg aatgggacgc ggccggtcga  17700
tcgacgatcc ggctgctaac aaagcccgaa aggaagctga gttggctgct gccaccgctg  17760
agcaataact agcataaccc cttggggcct ctaaacgggt cttgaggggt tttttgctga  17820
aaggaggaac tatatccgga tcgagatcaa ttctgtgagc gtatggcaaa cgaaggaaaa  17880
atagttatag tagccgcact cgatgggaca tttcaacgta aaccgtttaa taatattttg  17940
aatcttattc cattatctga aatggtggta aaactaactg ctgtgtgtat gaaatgcttt  18000
aaggaggctt ccttttctaa acgattgggt gaggaaaccg agatagaaat aataggaggt  18060
aatgatatgt atcaatcggt gtgtagaaag tgttacatcg actcataata ttatattttt  18120
tatctaaaaa actaaaaata aacattgatt aaattttaat ataatactta aaaatggatg  18180
ttgtgtcgtt agataaaccg tttatgtatt ttgaggaaat tgataatgag ttagattacg  18240
aaccagaaag tgcaaatgag gtcgcaaaaa aactgccgta tcaaggacag ttaaaactat  18300
tactaggaga attatttttt cttagtaagt tacagcgaca cggtatatta gatggtgcca  18360
ccgtagtgta tataggatct gctcccggta cacatatacg ttatttgaga gatcatttct  18420
ataatttagg agtgatcccg aaaggaagct gagttggctg ctgccaccgc tgagcaataa  18480
ctagcataac cccttggggc ctctaaacgg gtcttgaggg gttttttgct gaaaggagga  18540
acgcgcctga tgcggtattt tctccttacg catctgtgcg gtatttcaca ccgcatatat  18600
ggtgcactct cagtacaatc tgctctgatg ccgcatagtt aagccagccc cgacacccgc  18660
caacacccgc tgacgcgccc tgacgggctt gtctgctccc ggcatccgct tacagacaag  18720
ctgtgaccgt ctccgggagc tgcatgtgtc agaggttttc accgtcatca ccgaaacgcg  18780
cgagacgaaa gggcctcgtg atacgcctat ttttataggt taatgtcatg ataataatgg  18840
tttcttagac gtcaggtggc acttttcggg gaaatgtgcg cggaacccct atttgtttat  18900
ttttctaaat acattcaaat atgtatccgc tcatgagaca ataaccctga taaatgcttc  18960
aataatattg aaaaaggaag agtatgagta ttcaacattt ccgtgtcgcc cttattccct  19020
tttttgcggc attttgcctt cctgtttttg ctcacccaga aacgctggtg aaagtaaaag  19080
atgctgaaga tcagttgggt gcacgagtgg gttacatcga actggatctc aacagcggta  19140
agatccttga gagttttcgc cccgaagaac gttttccaat gatgagcact tttaaagttc  19200
tgctatgtgg cgcggtatta tcccgtattg acgccgggca agagcaactc ggtcgccgca  19260
tacactattc tcagaatgac ttggttgagt actcaccagt cacagaaaag catcttacgg  19320
atggcatgac agtaagagaa ttatgcagtg ctgccataac catgagtgat aacactgcgg  19380
ccaacttact tctgacaacg atcggaggac cgaaggagct aaccgctttt ttgcacaaca  19440
```

```
tgggggatca tgtaactcgc cttgatcgtt gggaaccgga gctgaatgaa gccataccaa  19500

acgacgagcg tgacaccacg atgcctgtag caatggcaac aacgttgcgc aaactattaa  19560

ctggcgaact acttactcta gcttcccggc aacaattaat agactggatg gaggcggata  19620

aagttgcagg accacttctg cgctcggccc ttccggctgg ctggtttatt gctgataaat  19680

ctggagccgg tgagcgtggg tctcgcggta tcattgcagc actggggcca gatggtaagc  19740

cctcccgtat cgtagttatc tacacgacgg ggagtcaggc aactatggat gaacgaaata  19800

gacagatcgc tgagataggt gcctcactga ttaagcattg gtaactgtca gaccaagttt  19860

actcatatat actttagatt gatttaaaac ttcattttta atttaaaagg atctaggtga  19920

agatcctttt tgataatctc atgaccaaaa tcccttaacg tgagttttcg ttccactgag  19980

cgtcagaccc cgtagaaaag atcaaaggat cttcttgaga tccttttttt ctgcgcgtaa  20040

tctgctgctt gcaaacaaaa aaaccaccgc taccagcggt ggtttgtttg ccggatcaag  20100

agctaccaac tctttttccg aaggtaactg gcttcagcag agcgcagata ccaaatactg  20160

tccttctagt gtagccgtag ttaggccacc acttcaagaa ctctgtagca ccgcctacat  20220

acctcgctct gctaatcctg ttaccagtgg ctgctgccag tggcgataag tcgtgtctta  20280

ccgggttgga ctcaagacga tagttaccgg ataaggcgca gcggtcgggc tgaacggggg  20340

gttcgtgcac acagcccagc ttggagcgaa cgacctacac cgaactgaga tacctacagc  20400

gtgagcattg agaaagcgcc acgcttcccg aagggagaaa ggcggacagg tatccggtaa  20460

gcggcagggt cggaacagga gagcgcacga gggagcttcc agggggaaac gcctggtatc  20520

tttatagtcc tgtcgggttt cgccacctct gacttgagcg tcgatttttg tgatgctcgt  20580

caggggggcg gagcctatgg aaaaacgcca gcaacgcggc ctttttacgg ttcctggcct  20640

tttgctggcc ttttgctcac atgttctttc ctgcgttatc ccctgattct gtggataacc  20700

gtattaccgc ctttgagtga gctgataccg ctcgccgcag ccgaacgacc gagcgcagcg  20760

agtcagtgag cgaggaagcg gaagagcgcc caatacgcaa accgcctctc cccgcgcgtt  20820

ggccgattca ttaatgcagc tggcacgaca ggtttcccga ctggaaagcg ggcagtgagc  20880

gcaacgcaat taatgtgagt tagctcactc attaggcacc ccaggcttta cactttatgc  20940

ttccggctcg tatgttgtgt ggaattgtga gcggataaca atttcacaca ggaaacagct  21000

atgaccatga ttacgccaag cttacgcgtc ctggcattat gcccagtaca tgaccttatg  21060

ggactttcct acttggcagt acatctacgt attagtcatc gctattacca tggtgatgcg  21120

gttttggcag tacatcaatg ggcgtggata gcggtttgac tcacggggat ttccaagtct  21180

ccaccccatt gacgtcaatg ggagtttgtt ttggcaccaa aatcaacggg actttccaaa  21240

atgtcgtaac aactccgccc cattgacgca aatgggcggt aggcgtgtac ggtgggaggt  21300

ctatataagc agagctcgtt tagtgaaccg tgg                               21333
```

<210> SEQ ID NO 9
<211> LENGTH: 21327
<212> TYPE: DNA
<213> ORGANISM: Artificial
<220> FEATURE:
<223> OTHER INFORMATION: artificial construct

<400> SEQUENCE: 9

```
accaaacaaa gttgggtaag gatagttcaa tcaatgatca tcttctagtg cacttaggat     60

tcaagatcct attatcaggg acaagagcag gattagggat atccgagatg gccacacttt    120
```

```
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggacatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatgggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagcagatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggctacag tgtcattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
```

```
tttggaacgg agatcgcgtc ttcattgaca ggtggtgcaa cccaatgtgc tcgaaagtca   2580
ccctcggaac catcagggcc aggtgcacct gcggggaacg tccccgagtg tgtgagcaat   2640
gccgcactga tacaggagtg gacacccgaa tctggcacca caatctcccc gagatcccag   2700
aataatgaag aagggggaga ccattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctgg tgaagataat aatgaagtag ctacagctca acttacctgc caaccccatg   3360
ccagtcgacc caactagcgt acgatgacgt cctagtacaa cctaaatcca ttataaaaaa   3420
cttaggagca aagtgattgc ctcccaagtt ccacaatgac agagatctac gacttcgaca   3480
agtcggcatg ggacatcaaa gggtcgatcg ctccgataca acccaccacc tacagtgatg   3540
gcaggctggt gccccaggtc agagtcatag atcctggtct aggcgacagg aaggatgaat   3600
gctttatgta catgtttctg ctgggggttg ttgaggacag cgattcccta gggcctccaa   3660
tcgggcgagc atttgggtcc ctgcccttag gtgttggcag atccacagca aagcccgaaa   3720
aactcctcaa agaggccact gagcttgaca tagttgttag acgtacagca gggctcaatg   3780
aaaaactggt gttctacaac aacaccccac taactctcct cacaccttgg agaaaggtcc   3840
taacaacagg gagtgtcttc aacgcaaacc aagtgtgcaa tgcggttaat ctgataccgc   3900
tcgatacccc gcagaggttc cgtgttgttt atatgagcat cacccgtctt tcggataacg   3960
ggtattacac cgttcctgga agaatgctgg aattcagatc ggtcaatgca gtggccttca   4020
acctgctggt gaccettagg attgacaagg cgataggccc tgggaagatc atcgacaata   4080
cagagcaact tcctgaggca acatttatgg tccacatcgg gaacttcagg agaaagaaga   4140
gtgaagtcta ctctgccgat tattgcaaaa tgaaaatcga aaagatgggc ctggtttttg   4200
cacttggtgg gatagggggc accagtcttc acattagaag cacaggcaaa atgagcaaga   4260
ctctccatgc acaactcggg ttcaagaaga ccttatgtta cccgctgatg gatatcaatg   4320
aagaccttaa tcgattactc tggaggagca gatgcaagat agtaagaatc caggcagttt   4380
tgcagccatc agttcctcaa gaattccgca tttacgacga cgtgatcata aatgatgacc   4440
aaggactatt caaagttctg tagaccgtag tgcccagcaa tgcccgaaaa cgaccccct   4500
cacaatgaca gccagaaggc ccggacaaaa aagcccctc cgaaagactc cacggaccaa   4560
gcgagaggcc agccagcagc cgacggcaag cgcgaacacc aggcggcccc agcacagaac   4620
agccctgaca caaggccacc accagccacc ccaatctgca tcctcctcgt gggacccccg   4680
aggaccaacc cccaaggctg cccccgatcc aaaccaccaa ccgcatcccc accacccccg   4740
ggaaagaaac ccccagcaat tggaaggccc ctccccctct tcctcaacac aagaactcca   4800
caaccgaacc gcacaagcga ccgaggtgac ccaaccgcag gcatccgact ccctagacag   4860
```

```
atcctctctc cccggcaaac taaacaaaac ttagggccaa ggaacataca cacccaacag   4920
aacccagacc ccggcccacg gcgccgcgcc cccaaccccc gacaaccaga gggagccccc   4980
aaccaatccc gccggctccc ccggtgccca caggcaggga caccaacccc cgaacagacc   5040
cagcacccaa ccatcgacaa tccaagacgg gggggccccc ccaaaaaaag gcccccaggg   5100
gccgacagcc agcaccgcga ggaagcccac ccacccccaca cacgaccacg gcaaccaaac   5160
cagaacccag accaccctgg gccaccagct cccagactcg gccatcaccc cgcagaaagg   5220
aaaggccaca acccgcgcac cccagccccg atccggcggg gagccaccca acccgaacca   5280
gcacccaaga gcgatccccg aaggaccccc gaaccgcaaa ggacatcagt atcccacagc   5340
ctctccaagt cccccggtct cctcctcttc tcgaagggac caaaagatca atccaccaca   5400
cccgacgaca ctcaactccc cacccctaaa ggagacaccg ggaatcccag aatcaagact   5460
catccaatgt ccatcatggg tctcaaggtg aacgtctctg ccatattcat ggcagtactg   5520
ttaactctcc aaacacccac cggtcaaatc cattggggca atctctctaa gataggggtg   5580
gtaggaatag gaagtgcaag ctacaaagtt atgactcgtt ccagccatca atcattagtc   5640
ataaaattaa tgcccaatat aactctcctc aataactgca cgagggtaga gattgcagaa   5700
tacaggagac tactgagaac agttttggaa ccaattagag atgcacttaa tgcagtgacc   5760
cagaatataa gaccggttca gagtgtagct tcaagtagga gacacaagag atttgcggga   5820
gtagtcctgg caggtgcggc cctaggcgtt gccacagctg ctcagataac agccggcatt   5880
gcacttcacc agtccatgct gaactctcaa gccatcgaca atctgagagc gagcctggaa   5940
actactaatc aggcaattga ggcaatcaga caagcagggc aggagatgat attggctgtt   6000
cagggtgtcc aagactacat caataatgag ctgataccgt ctatgaacca actatcttgt   6060
gatttaatcg gccagaagct cgggctcaaa ttgctcagat actatacaga aatcctgtca   6120
ttatttggcc ccagcttacg ggaccccata tctgcggaga tatctatcca ggctttgagc   6180
tatgcgcttg gaggagacat caataaggtg ttagaaaagc tcggatacag tggaggtgat   6240
ttactgggca tcttagagag cagaggaata aaggcccgga taactcacgt cgacacagag   6300
tcctacttca ttgtcctcag tatagcctat ccgacgctgt ccgagattaa gggggtgatt   6360
gtccaccggc tagagggggt ctcgtacaac ataggctctc aagagtggta taccactgtg   6420
cccaagtatg ttgcaaccca agggtacctt atctcgaatt ttgatgagtc atcgtgtact   6480
ttcatgccag aggggactgt gtgcagccaa aatgccttgt acccgatgag tcctctgctc   6540
caagaatgcc tccgggggtc caccaagtcc tgtgctcgta cactcgtatc cgggtctttt   6600
gggaaccggt tcattttatc acaagggaac ctaatagcca attgtgcatc aatcctttgc   6660
aagtgttaca caacaggaac gatcattaat caagaccctg acaagatcct aacatacatt   6720
gctgccgatc actgcccggt agtcgaggtg aacggcgtga ccatccaagt cgggagcagg   6780
aggtatccag acgctgtgta cttgcacaga attgacctcg gtcctcccat atcattggag   6840
aggttggacg tagggacaaa tctggggaat gcaattgcta agttggagga tgccaaggaa   6900
ttgttggagt catcggacca gatattgagg agtatgaaag gtttatcgag cactagcata   6960
gtctacatcc tgattgcagt gtgtcttgga gggttgatag ggatccccgc tttaatatgt   7020
tgctgcaggg ggcgttgtaa caaaaaggga gaacaagttg gtatgtcaag accaggccta   7080
aagcctgatc ttacgggaac atcaaaatcc tatgtaaggt cgctctgatc ctctacaact   7140
cttgaaacac aaatgtccca caagtctcct cttcgtcatc aagcaaccac cgcacccagc   7200
atcaagccca cctgaaatta tctccggttt ccctctggcc gaacaatatc ggtagttaat   7260
```

```
taaaacttag ggtgcaagat catccacaat gtcaccacaa cgagaccgga taaatgcctt   7320
ctacaaagat aacccccatc ccaagggaag taggatagtc attaacagag aacatcttat   7380
gattgataga ccttatgttt tgctggctgt tctgtttgtc atgtttctga gcttgatcgg   7440
gttgctagcc attgcaggca ttagacttca tcgggcagcc atctacaccg cagagatcca   7500
taaaagcctc agcaccaatc tagatgtaac taactcaatc gagcatcagg tcaaggacgt   7560
gctgacacca ctcttcaaaa tcatcggtga tgaagtgggc ctgaggacac ctcagagatt   7620
cactgaccta gtgaaattca tctctgacaa gattaaattc cttaatccgg atagggagta   7680
cgacttcaga gatctcactt ggtgtatcaa cccgccagag agaatcaaat tggattatga   7740
tcaatactgt gcagatgtgg ctgctgaaga gctcatgaat gcattggtga actcaactct   7800
actggagacc agaacaacca atcagttcct agctgtctca aagggaaact gctcagggcc   7860
cactacaatc agaggtcaat tctcaaacat gtcgctgtcc ctgttagact tgtatttagg   7920
tcgaggttac aatgtgtcat ctatagtcac tatgacatcc cagggaatgt atgggggaac   7980
ttacctagtg gaaaagccta atctgagcag caaaaggtca gagttgtcac aactgagcat   8040
gtaccgagtg tttgaagtag gtgttatcag aaatccgggt ttgggggctc cggtgttcca   8100
tatgacaaac tatcttgagc aaccagtcag taatgatctc agcaactgta tggtggcttt   8160
gggggagctc aaactcgcag ccctttgtca cggggaagat tctatcacaa ttccctatca   8220
gggatcaggg aaaggtgtca gcttccagct cgtcaagcta ggtgtctgga aatccccaac   8280
cgacatgcaa tcctgggtcc ccttatcaac ggatgatcca gtgatagaca ggctttacct   8340
ctcatctcac agaggtgtta tcgctgacaa ccaagcaaaa tgggctgtcc cgacaacacg   8400
aacagatgac aagttgcgaa tggagacatg cttccaacag gcgtgtaagg gtaaaatcca   8460
agcactctgc gagaatcccg agtgggcacc attgaaggat aacaggattc cttcatacgg   8520
ggtcttgtct gttgatctga gtctgacagt tgagcttaaa atcaaaattg cttcgggatt   8580
cgggccattg atcacacacg gttcagggat ggacctatac aaatccaacc acaacaatgt   8640
gtattggctg actatcccgc caatgaagaa cctagcctta ggtgtaatca acacattgga   8700
gtggataccg agattcaagg ttagtcccta cctcttcact gtcccaatta aggaagcagg   8760
cggagactgc catgccccaa catacctacc tgcggaggtg gatggtgatg tcaaactcag   8820
ttccaatctg gtgattctac ctggtcaaga tctccaatat gttttggcaa cctacgatac   8880
ttccagggtt gaacatgctg tggtttatta cgtttacagc ccaagccgct cattttctta   8940
cttttatcct tttaggttgc ctataaaggg ggtccccatc gaattacaag tggaatgctt   9000
cacatgggac caaaaactct ggtgccgtca cttctgtgtg cttgcggact cagaatctgg   9060
tggacatatc actcactctg ggatggtggg catgggagtc agctgcacag tcacccggga   9120
agatggaacc aatcgcagat agggctgcta gtgaaccaat cacatgatgt cacccagaca   9180
tcaggcatac ccactagtcc tccatcattg ttataaaaaa cttaggaacc aggtccacac   9240
agctcgagtc gcgcgtgcca ccatggagac agacacactc ctgctatggg tactgctgct   9300
ctgggttcca ggttccactg gtgactatcc atatgatgtt ccagattatg ctgaagtgca   9360
gctcgtggag agcggaggcg gattggtgca accaggcaaa tctctcaaac tgagctgcga   9420
agccagcgga ttcaccttct caggatatgg gatgcactgg gttagacaag ctcctgggag   9480
aggtcttgag tcagtcgcct acatcacctc ctctagcatc aacatcaagt atgcagatgc   9540
cgtgaaaggg cgattcacag ttagccggga caatgccaag aatctcctct ttctgcagat   9600
```

```
gaacatactg aagagtgagg atacagcgat gtactattgt gccaggtttg actgggataa   9660
gaactattgg ggacagggca caatggtcac tgtcagctct ggtggcggtg ggtcaggcgg   9720
aggcggttct ggcggcggcg gctctgacat tcagatgact cagtcaccgt catctctgcc   9780
cgcaagtttg ggtgatcgcg tgacaatcaa ttgccaagct agtcaggaca taagcaatta   9840
cctgaactgg taccagcaga agcctggtaa ggcacccaaa ctgctgatct actacacgaa   9900
caaacttgct gatggggtac catcccgttt ctccggcagt ggaagtggga gggacagctc   9960
ctttaccatt agctccctgg aaagcgagga cattgggtcc tactactgtc agcagtatta  10020
caactatccc tggacctttg ggcctggaac taagctggag attaagggag gaggcgggtc  10080
cggcgcccag gttcagctgg tccagtcagg ggctgagctg gtgaagcctg ggcctcagt   10140
gaagatgtcc tgcaaggctt ctggctacac atttaccagt tacaatatgc actgggtaaa  10200
gcagacacct ggacagggcc tggaatggat tggagctatt tatccaggaa atggtgatac  10260
ttcctacaat cagaagttca aaggcaaggc cacattgact gcagacaaat cctccagcac  10320
agcctacatg cagctcagca gcctgacatc tgaggactct gcggtctatt actgtgcaag  10380
agcgcaatta cgacctaact actggtactt cgatgtctgg ggcgcaggga ccacggtcac  10440
cgtgagcaag atctctggtg gcggtggctc gggcggtggt gggtcgggtg gcggaggctc  10500
gggtggctcg agcgacatcg tgctgtcgca gtctccagca atcctgtctg catctccagg  10560
ggagaaggtc acaatgactt gcagggccag ctcaagtgta agttacatgc actggtacca  10620
gcagaagcca ggatcctccc ccaaaccctg gatttatgcc acatccaacc tggcttctgg  10680
agtccctgct cgcttcagtg gcagtgggtc tgggacctct tactctctca caatcagcag  10740
agtggaggct gaagatgctg ccacttatta ctgccagcag tggattagta acccacccac  10800
gttcggtgct gggaccaagc tggagctgaa ggcggccgcc agaggctctc accaccatca  10860
tcaccactag gcgcgcgttc tagtgtgaaa tagacatcag aattaagaaa aacgtagggt  10920
ccaagtggtt ccccgttatg gactcgctat ctgtcaacca gatcttatac cctgaagttc  10980
acctagatag cccgatagtt accaataaga tagtagccat cctggagtat gctcgagtcc  11040
ctcacgctta cagcctggag gaccctacac tgtgtcagaa catcaagcac cgcctaaaaa  11100
acggattttc caaccaaatg attataaaca atgtggaagt tgggaatgtc atcaagtcca  11160
agcttaggag ttatccggcc cactctcata ttccatatcc aaattgtaat caggatttat  11220
ttaacataga agacaaagag tcaacgagga agatccgtga actcctcaaa aaggggaatt  11280
cgctgtactc caaagtcagt gataaggttt tccaatgctt aagggacact aactcacggc  11340
ttggcctagg ctccgaattg agggaggaca tcaaggagaa agttattaac ttgggagttt  11400
acatgcacag ctcccagtgg tttgagccct ttctgttttg gtttacagtc aagactgaga  11460
tgaggtcagt gattaaatca caaacccata cttgccatag gaggagacac acacctgtat  11520
tcttcactgg tagttcagtt gagttgctaa tctctcgtga ccttgttgct ataatcagta  11580
aagagtctca acatgtatat tacctgacat ttgaactggt tttgatgtat tgtgatgtca  11640
tagaggggag gttaatgaca gagaccgcta tgactattga tgctaggtat acagagcttc  11700
taggaagagt cagatacatg tggaaactga tagatggttt cttccctgca ctcgggaatc  11760
caacttatca aattgtagcc atgctggagc ctctttcact tgcttacctg cagctgaggg  11820
atataacagt agaactcaga ggtgctttcc ttaaccactg ctttactgaa atacatgatg  11880
ttcttgacca aaacgggttt tctgatgaag gtacttatca tgagttaatt gaagctctag  11940
attacatttt cataactgat gacatacatc tgacagggga gatttctcca tttttcagaa  12000
```

```
gtttcggcca ccccagactt gaagcagtaa cggctgctga aaatgttagg aaatacatga  12060
atcagcctaa agtcattgtg tatgagactc tgatgaaagg tcatgccata ttttgtggaa  12120
tcataatcaa cggctatcgt gacaggcacg gaggcagttg gccaccgctg accctccccc  12180
tgcatgctgc agacacaatc cggaatgctc aagcttcagg tgatgggtta acacatgagc  12240
agtgcgttga taactggaaa tcttttgctg gagtgaaatt tggctgcttt atgcctctta  12300
gcctggatag tgatctgaca atgtacctaa aggacaaggc acttgctgct ctccaaaggg  12360
aatgggattc agtttacccg aaagagttcc tgcgttacga ccctcccaag ggaaccgggt  12420
cacggaggct tgtagatgtt ttccttaatg attcgagctt tgacccatat gatgtgataa  12480
tgtatgttgt aagtggagct tacctccatg accctgagtt caacctgtct tacagcctga  12540
aagaaaagga gatcaaggaa acaggtagac tttttgctaa aatgacttac aaaatgaggg  12600
catgccaagt gattgctgaa aatctaatct caaacgggat tggcaaatat tttaaggaca  12660
atgggatggc caaggatgag cacgatttga ctaaggcact ccacactcta gctgtctcag  12720
gagtccccaa agatctcaaa gaaagtcaca ggggggggcc agtcttaaaa acctactccc  12780
gaagcccagt ccacacaagt accaggaacg tgagagcagc aaaagggttt atagggttcc  12840
ctcaagtaat tcggcaggac caagacactg atcatccgga gaatatggaa gcttacgaga  12900
cagtcagtgc atttatcacg actgatctca agaagtactg ccttaattgg agatatgaga  12960
ccatcagctt gtttgcacag aggctaaatg agatttacgg attgccctca tttttccagt  13020
ggctgcataa gaggcttgag acctctgtcc tgtatgtaag tgaccctcat tgcccccccg  13080
accttgacgc ccatatcccg ttatataaag tccccaatga tcaaatcttc attaagtacc  13140
ctatgggagg tatagaaggg tattgtcaga agctgtggac catcagcacc attccctatc  13200
tatacctggc tgcttatgag agcggagtaa ggattgcttc gttagtgcaa ggggacaatc  13260
agaccatagc cgtaacaaaa agggtaccca gcacatggcc ctacaacctt aagaaacggg  13320
aagctgctag agtaactaga gattactttg taattcttag gcaaaggcta catgatattg  13380
gccatcacct caaggcaaat gagacaattg tttcatcaca tttttttgtc tattcaaaag  13440
gaatatatta tgatgggcta cttgtgtccc aatcactcaa gagcatcgca agatgtgtat  13500
tctggtcaga gactatagtt gatgaaacaa gggcagcatg cagtaatatt gctacaacaa  13560
tggctaaaag catcgagaga ggttatgacc gttaccttgc atattccctg aacgtcctaa  13620
aagtgataca gcaaattctg atctctcttg gcttcacaat caattcaacc atgacccggg  13680
atgtagtcat acccctcctc acaaacaacg acctcttaat aaggatggca ctgttgcccg  13740
ctcctattgg ggggatgaat tatctgaata tgagcaggct gtttgtcaga aacatcggtg  13800
atccagtaac atcatcaatt gctgatctca agagaatgat tctcgcctca ctaatgcctg  13860
aagagaccct ccatcaggta atgacacaac aaccggggga ctcttcattc ctagactggg  13920
ctagcgaccc ttactcagca aatcttgtat gtgtccagag catcactaga ctcctcaaga  13980
acataactgc aaggtttgtc ctgatccata gtccaaaccc aatgttaaaa ggattattcc  14040
atgatgacag taaagaagag gacgagggac tggcggcatt cctcatggac aggcatatta  14100
tagtacctag ggcagctcat gaaatcctgg atcatagtgt cacaggggca agagagtcta  14160
ttgcaggcat gctggatacc acaaaaggct tgattcgagc cagcatgagg aagggggtt   14220
taacctctcg agtgataacc agattgtcca attatgacta tgaacaattc agagcaggga  14280
tggtgctatt gacaggaaga aagagaaatg tcctcattga caaagagtca tgttcagtgc  14340
```

```
agctggcgag agctctaaga agccatatgt gggcgaggct agctcgagga cggcctattt  14400
acggccttga ggtccctgat gtactagaat ctatgcgagg ccaccttatt cggcgtcatg  14460
agacatgtgt catctgcgag tgtggatcag tcaactacgg atggtttttt gtcccctcgg  14520
gttgccaact ggatgatatt gacaaggaaa catcatcctt gagagtccca tatattggtt  14580
ctaccactga tgagagaaca gacatgaagc ttgccttcgt aagagcccca agtcgatcct  14640
tgcgatctgc tgttagaata gcaacagtgt actcatgggc ttacggtgat gatgatagct  14700
cttggaacga agcctggttg ttggctaggc aaagggccaa tgtgagcctg gaggagctaa  14760
gggtgatcac tcccatctca acttcgacta atttagcgca taggttgagg gatcgtagca  14820
ctcaagtgaa atactcaggt acatcccttg tccgagtggc gaggtatacc acaatctcca  14880
acgacaatct ctcatttgtc atatcagata agaaggttga tactaacttt atataccaac  14940
aaggaatgct tctagggttg ggtgttttag aaacattgtt tcgactcgag aaagataccg  15000
gatcatctaa cacggtatta catcttcacg tcgaaacaga ttgttgcgtg atcccgatga  15060
tagatcatcc caggataccc agctcccgca agctagagct gagggcagag ctatgtacca  15120
acccattgat atatgataat gcacctttaa ttgacagaga tgcaacaagg ctatacaccc  15180
agagccatag gaggcacctt gtggaatttg ttacatggtc cacaccccaa ctatatcaca  15240
ttttagctaa gtccacagca ctatctatga ttgacctggt aacaaaattt gagaaggacc  15300
atatgaatga aatttcagct ctcatagggg atgacgatat caatagtttc ataactgagt  15360
ttctgctcat agagccaaga ttattcacta tctacttggg ccagtgtgcg gccatcaatt  15420
gggcatttga tgtacattat catagaccat cagggaaata tcagatgggt gagctgttgt  15480
catcgttcct ttctagaatg agcaaaggag tgtttaaggt gcttgtcaat gctctaagcc  15540
acccaaagat ctacaagaaa ttctggcatt gtggtattat agagcctatc catggtcctt  15600
cacttgatgc tcaaaacttg cacacaactg tgtgcaacat ggtttacaca tgctatatga  15660
cctacctcga cctgttgttg aatgaagagt tagaagagtt cacatttctc ttgtgtgaaa  15720
gcgacgagga tgtagtaccg gacagattcg acaacatcca ggcaaaacac ttatgtgttc  15780
tggcagattt gtactgtcaa ccagggacct gcccaccaat tcaaggtcta agaccggtag  15840
agaaatgtgc agttctaacc gaccatatca aggcagaggc tatgttatct ccagcaggat  15900
cttcgtggaa cataaatcca attattgtag accattactc atgctccctg acttatctcc  15960
ggcgaggatc gatcaaacag ataagattga gagttgatcc aggattcatt ttcgacgccc  16020
tcgctgaggt aaatgtcagt cagccaaaga tcggcagcaa caacatctca aatatgagca  16080
tcaaggcttt cagaccccca cacgatgatg ttgcaaaatt gctcaaagat atcaacacaa  16140
gcaagcacaa tcttcccatt tcagggggca atctcgccaa ttatgaaatc catgctttcc  16200
gcagaatcgg gttgaactca tctgcttgct acaaagctgt tgagatatca acattaatta  16260
ggagatgcct tgagccaggg gaggacggct tgttcttggg tgagggatcg ggttctatgt  16320
tgatcactta taaggagata cttaaactaa gcaagtgctt ctataatagt ggggtttccg  16380
ccaattctag atctggtcaa agggaattag caccctatcc ctccgaagtt ggccttgtcg  16440
aacacagaat gggagtaggt aatattgtca aagtgctctt taacgggagg cccgaagtca  16500
cgtgggtagg cagtgtagat tgcttcaatt tcatagttag taatatccct acctctagtg  16560
tggggtttat ccattcagat atagagacct tgcctgacaa agatactata gagaagctag  16620
aggaattggc agccatctta tcgatggctc tgctcctggg caaaatagga tcaatactgg  16680
tgattaagct tatgcctttc agcggggatt ttgttcaggg atttataagt tatgtagggt  16740
```

```
ctcattatag agaagtgaac cttgtatacc ctagatacag caacttcatc tctactgaat  16800
cttatttggt tatgacagat ctcaaggcta accggctaat gaatcctgaa aagattaagc  16860
agcagataat tgaatcatct gtgaggactt cacctggact tataggtcac atcctatcca  16920
ttaagcaact aagctgcata caagcaattg tgggagacgc agttagtaga ggtgatatca  16980
atcctactct gaaaaaactt acacctatag agcaggtgct gatcaattgc gggttggcaa  17040
ttaacggacc taagctgtgc aaagaattga tccaccatga tgttgcctca gggcaagatg  17100
gattgcttaa ttctatactc atcctctaca gggagttggc aagattcaaa gacaaccaaa  17160
gaagtcaaca agggatgttc cacgcttacc ccgtattggt aagtagcagg caacgagaac  17220
ttatatctag gatcacccgc aaattctggg ggcacattct tctttactcc gggaacaaaa  17280
agttgataaa taagtttatc cagaatctca agtccggcta tctgatacta gacttacacc  17340
agaatatctt cgttaagaat ctatccaagt cagagaaaca gattattatg acggggggtt  17400
tgaaacgtga gtgggttttt aaggtaacag tcaaggagac caaagaatgg tataagttag  17460
tcggatacag tgccctgatt aaggactaat tggttgaact ccggaaccct aatcctgccc  17520
taggtggtta ggcattattt gcaatatatt aaagaaaact ttgaaaatac gaagtttcta  17580
ttcccagctt tgtctggtgg ccggcatggt cccagcctcc tcgctggcgc cggctgggca  17640
acattccgag gggaccgtcc cctcggtaat ggcgaatggg acgcggccgg tcgatcgacg  17700
atccggctgc taacaaagcc cgaaaggaag ctgagttggc tgctgccacc gctgagcaat  17760
aactagcata accccttggg gcctctaaac gggtcttgag gggttttttg ctgaaaggag  17820
gaactatatc cggatcgaga tcaattctgt gagcgtatgg caaacgaagg aaaaatagtt  17880
atagtagccg cactcgatgg gacatttcaa cgtaaaccgt ttaataatat tttgaatctt  17940
attccattat ctgaaatggt ggtaaaacta actgctgtgt gtatgaaatg ctttaaggag  18000
gcttcctttt ctaaacgatt gggtgaggaa accgagatag aaataatagg aggtaatgat  18060
atgtatcaat cggtgtgtag aaagtgttac atcgactcat aatattatat tttttatcta  18120
aaaaactaaa aataaacatt gattaaattt taatataata cttaaaaatg gatgttgtgt  18180
cgttagataa accgtttatg tattttgagg aaattgataa tgagttagat tacgaaccag  18240
aaagtgcaaa tgaggtcgca aaaaaactgc cgtatcaagg acagttaaaa ctattactag  18300
gagaattatt ttttcttagt aagttacagc gacacggtat attagatggt gccaccgtag  18360
tgtatatagg atctgctccc ggtacacata tacgttattt gagagatcat ttctataatt  18420
taggagtgat cccgaaagga agctgagttg gctgctgcca ccgctgagca ataactagca  18480
taaccccttg gggcctctaa acgggtcttg aggggttttt tgctgaaagg aggaacgcgc  18540
ctgatgcggt attttctcct tacgcatctg tgcggtattt cacaccgcat atatggtgca  18600
ctctcagtac aatctgctct gatgccgcat agttaagcca gccccgacac ccgccaacac  18660
ccgctgacgc gccctgacgg gcttgtctgc tcccggcatc cgcttacaga caagctgtga  18720
ccgtctccgg gagctgcatg tgtcagaggt tttcaccgtc atcaccgaaa cgcgcgagac  18780
gaaagggcct cgtgatacgc ctatttttat aggttaatgt catgataata atggtttctt  18840
agacgtcagg tggcactttt cggggaaatg tgcgcggaac ccctatttgt ttatttttct  18900
aaatacattc aaatatgtat ccgctcatga gacaataacc ctgataaatg cttcaataat  18960
attgaaaaag gaagagtatg agtattcaac atttccgtgt cgcccttatt cccttttttg  19020
cggcattttg ccttcctgtt tttgctcacc cagaaacgct ggtgaaagta aaagatgctg  19080
```

```
aagatcagtt gggtgcacga gtgggttaca tcgaactgga tctcaacagc ggtaagatcc  19140
ttgagagttt tcgccccgaa gaacgttttc caatgatgag cacttttaaa gttctgctat  19200
gtggcgcggt attatcccgt attgacgccg ggcaagagca actcggtcgc cgcatacact  19260
attctcagaa tgacttggtt gagtactcac cagtcacaga aaagcatctt acggatggca  19320
tgacagtaag agaattatgc agtgctgcca taaccatgag tgataacact gcggccaact  19380
tacttctgac aacgatcgga ggaccgaagg agctaaccgc ttttttgcac aacatggggg  19440
atcatgtaac tcgccttgat cgttgggaac cggagctgaa tgaagccata ccaaacgacg  19500
agcgtgacac cacgatgcct gtagcaatgg caacaacgtt gcgcaaacta ttaactggcg  19560
aactacttac tctagcttcc cggcaacaat taatagactg gatggaggcg gataaagttg  19620
caggaccact tctgcgctcg gcccttccgg ctggctggtt tattgctgat aaatctggag  19680
ccggtgagcg tgggtctcgc ggtatcattg cagcactggg gccagatggt aagccctccc  19740
gtatcgtagt tatctacacg acggggagtc aggcaactat ggatgaacga aatagacaga  19800
tcgctgagat aggtgcctca ctgattaagc attggtaact gtcagaccaa gtttactcat  19860
atatacttta gattgattta aaacttcatt tttaatttaa aaggatctag gtgaagatcc  19920
tttttgataa tctcatgacc aaaatccctt aacgtgagtt ttcgttccac tgagcgtcag  19980
accccgtaga aaagatcaaa ggatcttctt gagatccttt ttttctgcgc gtaatctgct  20040
gcttgcaaac aaaaaaacca ccgctaccag cggtggtttg tttgccggat caagagctac  20100
caactctttt tccgaaggta actggcttca gcagagcgca gataccaaat actgtccttc  20160
tagtgtagcc gtagttaggc caccacttca agaactctgt agcaccgcct acatacctcg  20220
ctctgctaat cctgttacca gtggctgctg ccagtggcga taagtcgtgt cttaccgggt  20280
tggactcaag acgatagtta ccggataagg cgcagcggtc gggctgaacg gggggttcgt  20340
gcacacagcc cagcttggag cgaacgacct acaccgaact gagataccta cagcgtgagc  20400
attgagaaag cgccacgctt cccgaaggga gaaaggcgga caggtatccg gtaagcggca  20460
gggtcggaac aggagagcgc acgagggagc ttccaggggg aaacgcctgg tatctttata  20520
gtcctgtcgg gtttcgccac ctctgacttg agcgtcgatt tttgtgatgc tcgtcagggg  20580
ggcggagcct atggaaaaac gccagcaacg cggccttttt acggttcctg gccttttgct  20640
ggccttttgc tcacatgttc tttcctgcgt tatcccctga ttctgtggat aaccgtatta  20700
ccgcctttga gtgagctgat accgctcgcc gcagccgaac gaccgagcgc agcgagtcag  20760
tgagcgagga agcggaagag cgcccaatac gcaaaccgcc tctccccgcg cgttggccga  20820
ttcattaatg cagctggcac gacaggtttc ccgactggaa agcgggcagt gagcgcaacg  20880
caattaatgt gagttagctc actcattagg caccccaggc tttacacttt atgcttccgg  20940
ctcgtatgtt gtgtggaatt gtgagcggat aacaatttca cacaggaaac agctatgacc  21000
atgattacgc caagcttacg cgtcctggca ttatgcccag tacatgacct tatgggactt  21060
tcctacttgg cagtacatct acgtattagt catcgctatt accatggtga tgcggttttg  21120
gcagtacatc aatgggcgtg gatagcggtt tgactcacgg ggatttccaa gtctccaccc  21180
cattgacgtc aatgggagtt tgttttggca ccaaaatcaa cgggactttc caaaatgtcg  21240
taacaactcc gccccattga cgcaaatggg cggtaggcgt gtacggtggg aggtctatat  21300
aagcagagct cgtttagtga accgtgg                                       21327
```